US010338037B2

(12) United States Patent
Hof et al.

(10) Patent No.: US 10,338,037 B2
(45) Date of Patent: Jul. 2, 2019

(54) COMPOUNDS AND CONJUGATES FOR IDENTIFYING AND SEPARATING POST-TRANSLATIONALLY MODIFIED ANALYTES

(71) Applicant: UVic Industry Partnerships Inc., Victoria (CA)

(72) Inventors: Fraser Hof, Victoria (CA); Graham A. E. Garnett, Vancouver (CA)

(73) Assignee: UVic Industry Partnerships Inc., Victoria, BC (CA)

( * ) Notice: Subject to any disclaimer, the term of this patent is extended or adjusted under 35 U.S.C. 154(b) by 86 days.

(21) Appl. No.: 15/239,544

(22) Filed: Aug. 17, 2016

(65) Prior Publication Data

US 2017/0052154 A1    Feb. 23, 2017

Related U.S. Application Data

(60) Provisional application No. 62/206,711, filed on Aug. 18, 2015.

(51) Int. Cl.
| | |
|---|---|
| *G01N 30/00* | (2006.01) |
| *G01N 30/06* | (2006.01) |
| *C08B 37/00* | (2006.01) |
| *C08B 15/00* | (2006.01) |
| *C08F 257/02* | (2006.01) |
| *B01J 20/281* | (2006.01) |
| *C08B 37/02* | (2006.01) |

(52) U.S. Cl.
CPC .......... *G01N 30/482* (2013.01); *C08B 15/00* (2013.01); *C08B 37/0021* (2013.01); *C08F 257/02* (2013.01); *G01N 30/06* (2013.01); *G01N 2030/067* (2013.01)

(58) Field of Classification Search
CPC .... C08F 257/02; G01N 30/482; G01N 30/06; C08B 37/0021; C08B 37/0012; C08B 15/00; C07C 2601/16
See application file for complete search history.

(56) References Cited

U.S. PATENT DOCUMENTS

| | | | |
|---|---|---|---|
| 5,952,526 | A | 9/1999 | Lamartine |
| 2006/0019311 | A1 | 1/2006 | Moussa et al. |
| 2010/0062540 | A1 | 3/2010 | Cecillon et al. |
| 2014/0357503 | A1 | 12/2014 | Hof et al. |

FOREIGN PATENT DOCUMENTS

WO    WO 2013/091074    6/2013

OTHER PUBLICATIONS

Heterocyclic Chemistry, Heterocyclic Compounds, recovered from https://www2.chemistry.msu. edu/faculty/reusch/virttxtjml/heterocy. htm on Apr. 3, 2017, pp. 1-14. (Year: 2017).*
Wikipedia, Aliphatic Compound, pp. 1-3, recovered from https://en.wikipedia.org/ wiki/Aliphatic_compound Apr. 3, 2017 (Year: 2017).*
Zaragoza Dorwald, Side Reactions in Organic Synthesis, 2005, Wiley-VCH Verlag GmbH & Co. KGaA, Weinheim, Preface. p. IX. (Year: 2005).*
Yoshida et al, Chemistry Letters, Calix[4]arene-5,11,17,23-tetrasulfonate as an Analytical Reagent for Cerium(III) Ion, 1991, pp. 2105-2108. (Year: 1991).*
Daze et al, Organic Letters, Synthesis of New Trisulfonated Calix[4]arenes Functionalized at the Upper Rim, and Their Complexation with the Trimethyllysine Epigenetic Mark, 2012, 14(6), pp. 1512-15-15 with supporting information pp. 1-58. (Year: 2012).*
Korbakov et al (Langmuir, Acetylcholine Detection at Micromolar Concentrations with the Use of an Artificial Receptor-Based Fluorescence Switch, 2008, 24, pp. 2580-2587. (Year: 2008).*
Allen et al., "Inhibition of histone binding by supramolecular hosts," *Biochem. J.*, 459(3): 505-512, May 1, 2014.
Beshara et al., "A Simple Calixarene Recognizes Post-translationally Methylated Lysine," *ChemBioChem*, 11(1): 63-66, Nov. 20, 2009.
Daze et al., "Determining the effects of salt, buffer, and temperature on the complexation of methylated ammonium ions and methyllysines by sulfonated calixarenes," *Can. J. Chem.*, 91(11): 1072-1076, Jul. 4, 2013.
Daze et al., "Supramolecular hosts that recognize methyllysines and disrupt the interaction between a modified histone tail and its epigenetic reader protein," *Chemical Science*, vol. 3, pp. 2695-2699, Jun. 21, 2012.
Daze et al., "Synthesis of New Trisulfonated Calix[4]arenes Functionalized at the Upper Rim, and Their Complexation with the Trimethyllysine Epigenetic Mark," *Organic Letters*, 14(6): 1512-1515, Mar. 7, 2012.
Daze et al., "The Cation-π Interaction at Protein-Protein Interaction Interfaces: Developing and Learning from Synthetic Mimics of Proteins That Bind Methylated Lysines," *Accounts of Chemical Research*, 46(4): 937-945, Jun. 22, 2012.
Daze, "Synthesis and evaluation of supramolecular chemical tools to study and disrupt epigenetic pathways," Thesis Dissertation submitted at Simon Fraser University, Apr. 28, 2014.

(Continued)

*Primary Examiner* — Paul A Zucker
(74) *Attorney, Agent, or Firm* — Klarquist Sparkman, LLP

(57) ABSTRACT

Disclosed herein are embodiments of compounds, conjugates, and devices, such as columns comprising such compounds and/or conjugates, that can be used to identify, separate, and quantify post-translationally modified analytes. The disclosed compounds and conjugates can be used to discriminate between analytes, such as peptides, having different post-translation modifications, such as methylations, phosphorylations, acetylations, citrullinations, hydroxylations, nitrosylations, ADP-ribosylations, glycosylations, propionylations, butyrylations, crotonylations, 2-hydroxyisobutyrylations, malonylations, succinylations, formylations, ubiquitinations, neddylations, proline cis-trans isomerizations. In particular disclosed embodiments, the compounds and conjugates can be used to separate peptides having different degrees of methylation.

22 Claims, 14 Drawing Sheets

(56) References Cited

OTHER PUBLICATIONS

Florea et al., "A Fluorescence-Based Supramolecular Tandem Assay for Monitoring Lysine Methyltransferase Activity in Homogeneous Solution," *Chem. Eur. J.*, 18(12): 3521-3528, Feb. 24, 2012.

Garnett, "Substitutions of sulfonatocalix[4]arenes that lead to applications in biomolecular recognition and give rise to novel self-association phenomena," Thesis Abstract submitted at University of Victoria, circa Dec. 23, 2014.

McGovern et al., "Structural study of a small molecule receptor bound to dimethyllysine in lysosome," *Chem. Sci.*, 6(1): 442-449, Jan. 1, 2015.

Minaker et al., "Antibody-Free Reading of the Histone Code Using a Simple Chemical Sensor Array," *Journal of the American Chemical Society*, 134(28): 11674-11680, Jun. 14, 2012.

Tabet et al., "Synthetic trimethyllysine receptors that bind histone 3, trimethyllysine 27 (H3K27me3) and disrupt its interaction with the epigenetic reader protein CBX7," *Bioorganic & Medicinal Chemistry*, 21(22): 6857-7230, Sep. 19, 2013.

Tabet, "Development of fluorescence-based supramolecular tools for studying histone post-translational modifications," Thesis Dissertation submitted at Department of Chemistry, University of Victoria, circa Apr. 29, 2014.

Coleman et al., "Enhanced detection of the pathogenic prion protein by its supramolecular associate with para-sulfonato-calix[n]arene derivatives," *New Journal of Chemistry*, vol. 31, pp. 711-717, 2007.

International Search Report and Written Opinion issued for International Application No. PCT/CA2012/001174, dated Mar. 8, 2013.

Lee et al., "Supramolecular fishing for plasma membrane proteins using an ultrastable synthetic host-guest binding pair," *Nature Chemistry*, vol. 3, pp. 154-159, 2011.

\* cited by examiner

COMPOUNDS AND CONJUGATES FOR IDENTIFYING AND SEPARATING POST-TRANSLATIONALLY MODIFIED ANALYTES

CROSS REFERENCE TO RELATED APPLICATION

This application claims priority to and the benefit of the earlier filing date of U.S. Provisional Patent Application No. 62/206,711, filed on Aug. 18, 2015, which is incorporated by reference herein in its entirety.

FIELD

The present disclosure concerns embodiments of compounds and conjugates that can be used to identify and separate post-translationally modified analytes.

BACKGROUND

Post-translational protein modification is a component of many cellular pathways. Prominent examples include methylation, phosphorylation, acetylation, and ubiquitylation. Post-translationally methylated lysine and arginine residues are central players in epigenetic pathways and are the subject of intense research into their roles in healthy development, stem cell pathways, and disease. DNA-packaging histones were the first proteins whose methylation was intensely studied, but it is increasingly clear that all plant and animal proteomes have many hundreds of methylated proteins.

Methylation stands apart from other modifications in multiple ways. It is the smallest group that can be added to a biomolecule. While many post-translational modifications (or "PTMs") create dramatic changes in a protein's physicochemical properties by installing charge on a neutral site (phosphorylation) or rendering a charged residue neutral (acetylation, citrullination), methylation does not significantly change the charge or $pK_a$'s of lysine or arginine side chains. Unlike all other PTMs, methyl groups are installed and removed by enzymes that must control the number of resulting methyl groups installed with high specificity. For example, lysine can be mono-, di-, or trimethylated, and arginine can be monomethylated or dimethylated (with dimethylarginine existing as two isomeric marks). Even when they occur at the same site, each kind of methyl mark encodes distinct epigenetic signaling outcomes. "Methylation" therefore defines an entire class of PTMs that generate enormous diversity in biochemical structure and function, without generating a large change in physico-chemical or stereoelectronic properties.

Analysis of methyl marks and other PTMs, however, remains difficult using conventional techniques. There exists a need in the art for sensitive chemical affinity based methods that can identify and separate post-translationally modified analytes.

SUMMARY

Disclosed herein are embodiments of conjugates, comprising a compound having a structure satisfying Formula I as described below, and a support component coupled to at least one of the variables A, E, G, J, L, M, N, or Q. In some embodiments, Formula I is

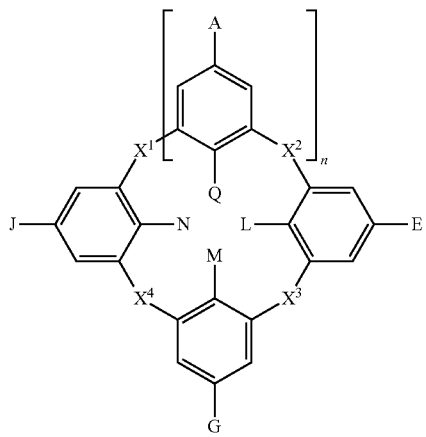

wherein each of A, E, G, and J independently is —N(R$^b$)$_2$; halogen; —SO$_3^-$, —CO$_2^-$; aryl; heteroaryl; -linker-aryl; or -linker-heteroaryl; each of L, M, N, and Q independently is —OR$_b$; —O$^-$; —SH; —S$^-$; —N(R$^b$)$_2$, -linker-aryl; or -linker-heteroaryl; each of X$^1$, X$^2$, X$^3$, and X$^4$ independently is CH$_2$, O, S, or NR$^b$; n is an integer selected from 1 to 3; and each R$^b$ independently is hydrogen, aliphatic, heteroaliphatic, aryl, or heteroaryl.

In particular disclosed embodiments, one or more of A, E, G, J, L, M, N, and Q is —N(R$^b$)$_2$ (wherein R$^b$ independently is hydrogen, aliphatic, hetero aliphatic, aryl, or heteroaryl), aryl, heteroaryl, —NR$^b$C(O)-aryl (wherein R$^b$ independently is hydrogen, aliphatic, heteroaliphatic, aryl, or heteroaryl), —NR$^b$C(O)-heteroaryl (wherein R$^b$ independently is hydrogen, aliphatic, heteroaliphatic, aryl, or heteroaryl), —NR$^b$SO$_2$-aryl (wherein R$^b$ independently is hydrogen, aliphatic, heteroaliphatic, aryl, or heteroaryl), —NR$^b$SO$_2$heteroaryl (wherein R$^b$ independently is hydrogen, aliphatic, heteroaliphatic, aryl, or heteroaryl), —OC(O)-aryl, —OC(O)-heteroaryl, —OC(O)O-aryl, —OC(O)O-heteroaryl, —OSO$_2$-aryl, —OSO$_2$-heteroaryl, —SC(O)-aryl, or —SC(O)-heteroaryl; and the remaining of A, E, G, J, L, M, N, and Q are independently —SO$_3^-$, —CO$_2^-$, —OH, or —O$^-$. In such embodiments, the aryl group can be phenyl or phenyl substituted with an aliphatic moiety, a heteroaliphatic moiety, a halogen, a heteroatom-containing moiety, or a combination thereof. Also in such embodiments, the aliphatic moiety can be alkyl, alkenyl, or alkynyl; the heteroaliphatic moiety can be alkoxy, ether, thioether, amine (—NHR$^b$, —NR$^b$R$^c$, or —(CH$_2$)$_p$NHR$^b$, wherein R$^b$ and R$^c$ independently are hydrogen, aliphatic, heteroaliphatic, aryl, or heteroaryl; and p is an integer selected from 0 to 10); the halogen can be chloro, iodo, bromo, or fluoro; and the heteroatom-containing moiety can be aldehyde (—(CH$_2$)$_p$C(O)H), acyl halide (—(CH$_2$)$_p$C(O)X, wherein X is selected from fluorine, chlorine, bromine, and iodine), carbonate (—(CH$_2$)$_p$C(O)OR$^b$, wherein R$^b$ is hydrogen, aliphatic, heteroaliphatic, aryl, or heteroaryl), carboxyl (—(CH$_2$)$_p$C(O)OH), carboxylate (—(CH$_2$)$_p$COO$^-$), ester (—(CH$_2$)$_p$C(O)OR$^b$), hydroxyl (—(CH$_2$)$_p$OH), ketone (—(CH$_2$)$_p$C(O)R$^b$), peroxy (—(CH$_2$)$_p$OOR$^b$, wherein R$^b$ is hydrogen, aliphatic, heteroaliphatic, aryl, or heteroaryl), hydroperoxy (—(CH$_2$)$_p$OOH), phosphate (—(CH$_2$)$_p$OP(O)OH$_2$), phosphoryl (—(CH$_2$)$_p$P(O)(OH)$_2$), phosphodiester [—(CH$_2$)$_p$(O)P(OH)OR$^b$], wherein R$^b$ is hydrogen, aliphatic, heteroaliphatic, aryl, or heteroaryl], thiol (—(CH$_2$)$_p$SH), disulfide (—(CH$_2$)$_p$SSR$^b$, wherein R$^b$ is hydrogen, aliphatic, heteroaliphatic, aryl, or heteroaryl), sulfinyl (—(CH$_2$)$_p$S(O)R$^b$, wherein R$^b$ is hydrogen, aliphatic, heteroaliphatic, aryl, or heteroaryl), sulfonate ester (—$(CH_2)_pSO_2OR^b$, wherein $R^b$ is hydrogen, aliphatic, heteroaliphatic, aryl, or heteroaryl), sulfonyl (—$(CH_2)_pSO_2R^b$, wherein $R^b$ is hydrogen, aliphatic, heteroaliphatic, aryl, or heteroaryl), carbonothioyl (—$(CH_2)_pC(S)R^b$ or —$(CH_2)_pC(S)H$, wherein $R^b$ is hydrogen, aliphatic, heteroaliphatic, aryl, or heteroaryl), sulfino (—$(CH_2)_pS(O)OH$), sulfo (—$(CH_2)_pSO_3H$), thiocyanate (—$(CH_2)_pSCN$), isothiocyanate (—$(CH_2)_pNCS$), oxazole, oxadiazole, imidazole, triazole, tetrazole, amide (—$(CH_2)_pC(O)NR^bR^C$, wherein $R^b$ and $R^C$ independently are hydrogen, aliphatic, heteroaliphatic, aryl, or heteroaryl), azide (—$(CH_2)_pN_3$), azo (—$(CH_2)_pNNR^b$, wherein $R^b$ is hydrogen, aliphatic, heteroaliphatic, aryl, or heteroaryl), isocyanate (—$(CH_2)_pNCO$), imide (—$(CH_2)_pC(O)NR^bC(O)R^c$, wherein $R^b$ and $R^c$ independently are hydrogen, aliphatic, heteroaliphatic, aryl, or heteroaryl), nitrile (—$(CH_2)_pCN$), isonitrile (—$(CH_2)_pN^+\equiv C^-$), nitro (—$(CH_2)_pNO_2$), nitroso (—$(CH_2)_p NO$), nitromethyl (—$(CH_2)_pCH_2NO_2$), or —$(CH_2)_pNH_2$, wherein each p independently is an integer selected from 0 to 10.

In some embodiments, each of A, E, G, and J independently is —$NH_2$, —$N(C_1$-$C_{10}alkyl)_2$, Cl, F, Br, or I, —$SO_3^-$, —$CO_2^-$, —$(CH_2)_pPh(CH_2)_p(Y)_m$, —$NHC(O)Ph(CH_2)_p(Y)_m$, —$NHSO_2Ph(CH_2)_p(Y)_m$, —$OC(O)Ph(CH_2)_p(Y)_m$, or —$OSO_2Ph(CH_2)_p(Y)_m$, wherein each Y independently is positioned ortho, meta, or para on the Ph group and is aliphatic, aryl, halogen, heteroaliphatic, heteroaryl, a heteroatom-containing function group, or a combination thereof, each m is an integer selected from 0 to 4, and each p independently is an integer selected from 0 to 10; each L, M, N, and Q independently is —OH, —O—OC(O)Ph $(CH_2)_p$ $(Y)_m$, —$O(CH_2)_pY$, or —$OSO_2Ph(CH_2)_p(Y)_m$, wherein each Y independently is positioned ortho, meta, or para on the Ph ring and is aliphatic, aryl, halogen, heteroaliphatic, heteroaryl, a heteroatom-containing function group, or a combination thereof, and m is an integer selected from 0 to 4; each of $X^1$, $X^2$, $X^3$, and $X^4$ independently can be $CH_2$ or S; and n is 1. Additional exemplary compounds and compound formulas are described herein.

In particular disclosed embodiments, the support component comprises a resin, a bead, a polymeric matrix, a metal oxide, a powder, a crystalline compound, an amorphous compound, or a combination thereof. In yet additional embodiments, the support component comprises agarose, sepharose, cellulose, modified cellulose, dextran, polyacrylamide, polystyrene, latex, bonded silica gel, silica based solid, activated alumina, a polysaccharide polymer, a resinous polymer, or a combination thereof.

In some embodiments, the conjugate has a structure satisfying Formula II

Formula II

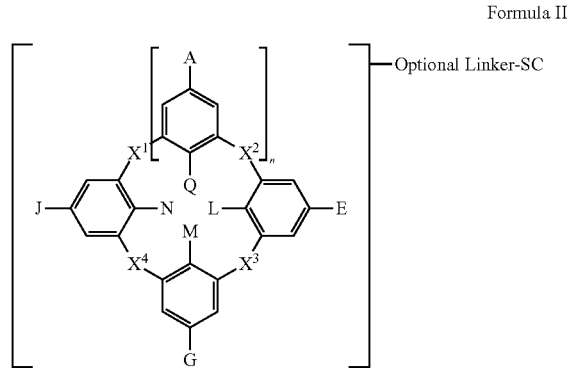

wherein the optional linker, if present, is selected from aliphatic, heteroaliphatic, aryl, heteroaryl, or a heteroatom-containing functional group; and SC is the support component. Other exemplary conjugate structures and formulas are described herein.

Also disclosed herein are compounds having a structure satisfying Formula I and provided that the compound is not

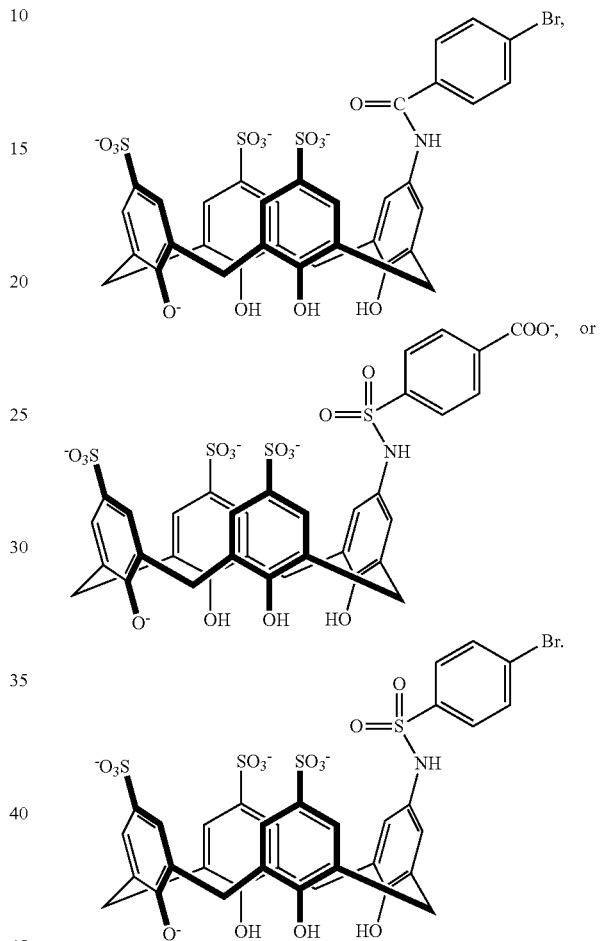

Also disclosed herein are embodiments of a chromatography column comprising one or more of the conjugates or compounds disclosed herein.

Also disclosed herein are embodiments of methods for using the compounds. Such methods can comprise introducing a fluid sample comprising one or more analytes into a solid-phase column packed with one or more conjugates comprising a compound having a structure satisfying Formula I as described herein and a support component coupled to at least one of A, E, G, J, L, M, N, or Q. The methods can further comprise applying a first buffer of a first concentration to the solid-phase column and applying a second buffer of a second concentration to elute one or more post-translationally modified analytes present in the sample. In some embodiments, the first buffer is a low ionic strength phosphate buffer and the second buffer is a chloride salt buffer or other salt buffer. In additional embodiments, the method can further comprise adjusting flow rates of the first buffer and the second buffer through the column so as to control elution times of the analytes present in the sample and wherein the analytes elute at different times depending on whether or not they are associated with the compound of the conjugate. In some embodiments, the method is used to separate one or more post-translationally modified analytes from unmodified analytes.

The foregoing and other objects, features, and advantages of the present disclosure will become more apparent from the following detailed description, which proceeds with reference to the accompanying figures.

BRIEF DESCRIPTION OF THE DRAWINGS

FIG. 17A is an overlay of 20 µL and 40 µL injections of a solution of AARKSAPY K; FIG. 17B is an overlay of 20 µL and 40 µL injections of a solution of AARKSAPY KMe3; FIG. 17C is an overlay of 40 µL injections from of AARKSAPY K and KMe3 variants; FIG. 17D is shows results for a 40 µL injection of solution consisting of AARKSAPY K and KMe3 variants, both at 1 mM; FIG. 17E is an overlay of separate 20 µL injections of ARTKQTARKSTGY K, K4Me3 and K9Me3 variants; and FIG. 17F shows results from a 20 µL injection of a solution consisting of ARTKQTARKSTGY K and K9Me3 variants, both at 1.0 mM.

DETAILED DESCRIPTION

I. Explanation of Terms

Figure 1A:
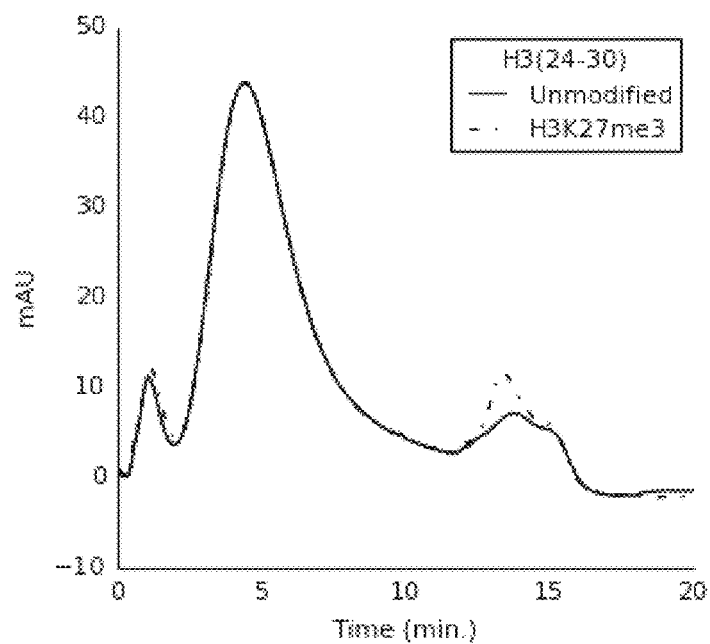
FIGS. 1A and 1B are chromatograms of peptide 7-mers (FIG. 1A) or 12-mers (FIG. 1B) run on a control sulfonate-based commercial strong cation-exchange column that does not comprise a compound or conjugate disclosed herein; the chromatograms illustrate that the control column cannot resolve peptides on the basis of methylation.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a "—," which is provided to depict the atom of the functional group that is bound to the compound or conjugate.

Aliphatic: A hydrocarbon, or a radical thereof, having at least one carbon atom to 50 carbon atoms, such as one to 25 carbon atoms, or one to ten carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkyl: A saturated monovalent hydrocarbon having at least one carbon atom to 50 carbon atoms, such as one to 25 carbon atoms, or one to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms to 50 carbon atoms, such as two to 25 carbon atoms, or two to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: $-(CH_2)_pO$-alkyl, wherein p is an integer selected from 0 to 10, with exemplary embodiments including, but not limited to, methoxy, ethoxy, n-propoxy, isopropoxy, n-butoxy, t-butoxy, sec-butoxy, n-pentoxy.

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

Heteroatom-Containing Functional Group: A functional group present in a compound or conjugate that contains at least one atom that is not carbon or hydrogen. Examples include, but are not limited to, aldehyde ($-(CH_2)_pC(O)H$), acyl halide ($-(CH_2)_pC(O)X$, wherein X is selected from fluorine, chlorine, bromine, and iodine), carbonate ($-(CH_2)_p\,OC(O)OR^b$, wherein $R^b$ is hydrogen, aliphatic, heteroaliphatic, aryl, or heteroaryl), carboxyl ($-(CH_2)_pC(O)OH$), carboxylate ($-(CH_2)_pCOO^-$), ester ($-(CH_2)_pC(O)OR^b$), hydroxyl ($-(CH_2)_pOH$), ketone ($-(CH_2)_pC(O)R^b$), peroxy ($-(CH_2)_pOOR^b$, wherein $R^b$ is hydrogen, aliphatic, heteroaliphatic, aryl, or heteroaryl), hydroperoxy ($-(CH_2)_p\,OOH$), phosphate ($-(CH_2)_pOP(O)OH_2$), phosphoryl ($-(CH_2)_pP(O)(OH)_2$), phosphodiester [$-(CH_2)_p(O)_p(OH)OR^b$), wherein $R^b$ is hydrogen, aliphatic, heteroaliphatic, aryl, or heteroaryl], thiol ($-(CH_2)_pSH$), disulfide ($-(CH_2)_p\,SSR^b$, wherein $R^b$ is hydrogen, aliphatic, heteroaliphatic, aryl, or heteroaryl), sulfinyl ($-(CH_2)_pS(O)R^b$, wherein $R^b$ is hydrogen, aliphatic, heteroaliphatic, aryl, or heteroaryl), sulfonate ($-(CH_2)_pSO_3^-$), sulfonate ester ($-(CH_2)_p\,SO_2OR^b$, wherein $R^b$ is hydrogen, aliphatic, heteroaliphatic, aryl, or heteroaryl), sulfonyl ($-(CH_2)_pSO_2R^b$, wherein $R^b$ is hydrogen, aliphatic, heteroaliphatic, aryl, or heteroaryl), carbonothioyl ($-(CH_2)_pC(S)R^b$ or $-(CH_2)_pC(S)H$, wherein $R^b$ is hydrogen, aliphatic, heteroaliphatic, aryl, or heteroaryl), sulfino ($-(CH_2)_pS(O)OH$), sulfo ($-(CH_2)_pSO_3H$), thiocyanate ($-(CH_2)_pSCN$), isothiocyanate ($-(CH_2)_pNCS$), oxazole, oxadiazole, imidazole, triazole, tetrazole, amide ($-(CH_2)_pC(O)NR^bR^c$, wherein $R^b$ and $R^c$ independently are hydrogen, aliphatic, heteroaliphatic, aryl, or heteroaryl), azide ($-(CH_2)_pN_3$), azo ($-(CH_2)_pN\text{-}NR^b$, wherein $R^b$ is hydrogen, aliphatic, heteroaliphatic, aryl, or heteroaryl), isocyanate ($-(CH_2)_pNCO$), imide ($-(CH_2)_pC(O)NR^bC(O)R^c$, wherein $R^b$ and $R^c$ independently are hydrogen, aliphatic, heteroaliphatic, aryl, or heteroaryl), nitrile ($-(CH_2)_pCN$), isonitrile ($-(CH_2)_pN^+\!\!=\!\!C^-$), nitro ($-(CH_2)_pNO_2$), nitroso ($-(CH_2)_pNO$), nitromethyl ($-(CH_2)_pCH_2NO_2$), or $-(CH_2)_pNH_2$, wherein each p independently is an integer selected from 0 to 10.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated herein. Additionally, particular functional groups of the disclosed compounds and conjugates are ionizable under certain conditions (e.g., acidic or basic conditions); thus, while a certain form of the functional group is illustrated herein, the corresponding ionized or neutral functional group also can be contemplated by the present disclosure.

II. Introduction

Analysis of post-translational modifications remains difficult with currently existing technologies, particularly analysis of methyl marks. For example, standard proteomics analysis, such as digestion followed by LC-MS/MS, allows one to identify methylated residues, but competition for ionization in complex samples suppresses signals for low abundance analytes. Pre-enrichment must be used for methylation proteomics. A variety of antibodies and engineered proteins have been developed that achieve pre-enrichment of analytes bearing a single kind of methylation mark; however, modifications representing relatively small changes in size and charge, such as lysine PTMs, can be difficult to target specifically with antibodies. Further complications exist when applying antibodies to the recognition of histone PTMs present on the N-terminal tail. The N-terminal tails of histones H3 and H4 are perhaps the densest regions of PTMs known. Lysine residues present on the histone tails can be signaling residues and frequently are methylated or acetylated; modifications that antibodies have trouble distinguishing. Additionally, histones have areas of high sequence similarity between which it can be difficult for antibodies to differentiate. An antibody raised to detect a PTM at one site may cross react when the modification is deposited on a different site with a similar surrounding sequence. It can be difficult to predict how antibodies will react when presented with multiple PTMs on a short sequence, such as the N-terminal region of histone H3, necessitating stringent cross-reactivity screening during antibody development and diligence.

Pan-specific reagents—that is reagents that bind to a certain modification only without regard for its surrounding peptide sequence—are of particular value for proteome-wide experiments of many kinds. Antibodies raised against a single methylated hapten can produce high specificity on the basis of both methylation state (mono-methylated, di-methylated, tri-methylated, and the like) and a specific methylation site. Polyclonal and monoclonal antibodies for many high-value methylation marks exist and antibodies can also be produced with somewhat more generic haptens, bearing a certain PTM in a structural context that aims not to be recognized by the host animal's immune system. These efforts can give rise to "pan-specific" antibodies; however, few monoclonal, pan-specific methyllysine antibodies exist. Cross-reactivity rates are known to be especially high for anti-PTM antibodies in general, and possibly more so for pan-specific antibodies. One pan-specific anti-Kme1Kme2 antibody, Abcam Ab23366, has been used, but only three of its top 20 targets from the tested array of PTM peptides bear Kme2 residues, and zero have Kme1 residues. Other pan-specific antibodies have not yet been tested in rigorous peptide array methods. Cell-lysate enrichments have been performed with pan-specific antibody mixtures developed for each of mono-, di-, trimethyllysine, monomethylarginine, and/or asymmetric dimethylarginine prior to proteomics analysis. Where direct comparisons have been made between enrichments done with different examples of the currently available pan-specific antibodies, the results from different antibodies have been very different from each other.

A few other biomolecule-driven methods for PTM enrichment have been developed. In a 'chemical proteomics' variation on antibody-driven approaches, cell lysates were chemically treated with propionic anhydride prior to digestion and enrichment with an antibody specific for propionylated Kme1. Other efforts have eliminated the need for antibodies altogether by using methyl reader proteins as a basis for engineering affinity reagents. However, these biomolecule-driven methods do not provide PTM enrichment based on chemical affinity. There remains a need for chemical affinity reagents for PTM enrichment, such as methyl enrichment, which offer advantages over biomolecule-driven methods, such as high chemical stability and high reproducibility. In particular, no chemical affinity-based enrichment of methylated analytes is currently possible.

The present inventors have discovered unique chemical compounds (or "scaffolds") that can be used in chemical affinity-based PTM enrichment. The disclosed compounds can be used to bind a variety of PTMs, with certain embodiments binding methylated amino acids, methylated peptides, and methylated proteins. Some embodiments bind such methylated compounds in solution. The disclosed compounds can bind strongly enough to out-compete the native protein-protein interactions. The presently disclosed compounds serve as affinity agents that are different from polyclonal and monoclonal antibodies or MBT domains. The small binding pockets of the presently disclosed compounds imparts a reactivity that allows the compounds to interact with their targets in a limited manner as compared to the extensive binding surfaces present on antibodies or engineered proteins. This reactivity makes them useful in pan-specific recognition of PTMs. The disclosed compounds also act as affinity reagents without the drawback of exhibiting single high-value analyte recognition with high, antibody-like specificity. Also, the disclosed compounds can be made with high batch-to-batch reproducibility and exhibit good stability.

III. Compounds and Conjugates

Disclosed herein are embodiments of compounds and conjugates comprising such compounds in combination with support components. The compounds and conjugates can be used as chemical affinity reagents for separating and isolating post-translationally modified compounds. In some embodiments, the compounds disclosed herein comprise a macrocyclic skeleton (e.g., a calixarene skeleton) that can bind an analyte. In some embodiments, the compounds bind an analyte non-covalently and/or covalently. In particular disclosed embodiments, non-covalent interactions between the analyte and the compound occur. The compounds disclosed herein can have structures satisfying Formula I below:

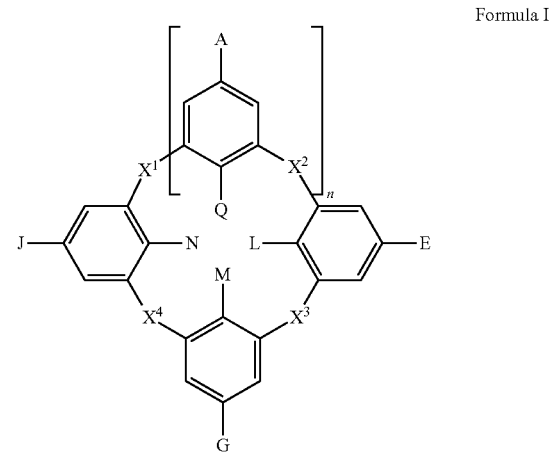

Formula I wherein
each of A, E, G, and J independently can be —N(R$^b$)$_2$; halogen, such as Cl, F, Br, or I; —SO$_3^-$, —CO$_2^-$; aryl; heteroaryl; -linker-aryl; or -linker-heteroaryl;
each of L, M, N, and Q independently can be —OR$^b$; —O$^-$; —SH; —S$^-$; —N(R$^b$)$_2$, -linker-aryl; or -linker-heteroaryl;

each of $X^1$, $X^2$, $X^3$, and $X^4$ independently can be $CH_2$, O, S, or $NR^b$;

n can be an integer selected from 1 to 3, such as 1, 2, or 3; and each $R^b$ independently can be hydrogen, aliphatic, heteroaliphatic, aryl, or heteroaryl.

In particular disclosed embodiments, the linker groups described above can be a heteroatom-containing functional group, an aliphatic group, an aryl group, a heteroaryl group, or a heteroaliphatic group. In some embodiments, the linker can be a nitrogen-containing functional group (e.g., amide, imine, or the like), an oxygen-containing functional group (e.g., ketone, ester, carbonate, or the like), a sulfur-containing functional group (e.g., sulfonamide [—NH—SO$_2$—], sulfonyl, sulfonate ester [—SO$_2$OR$^b$], thioester, or the like); an alkyl, alkenyl, or alkynyl group; or an ether, a thioether, or an amine.

In some embodiments, each of A, E, G, J, L, M, N, and Q independently can be —NR$^b$C(O)-aryl, —NR$^b$C(O)-heteroaryl, —NR$^b$SO$_2$-aryl, —NR$^b$SO$_2$heteroaryl, —OC(O)-aryl, —OC(O)-heteroaryl, —OC(O)O-aryl, —OC(O)O-heteroaryl, —OSO$_2$-aryl, —OSO$_2$-heteroaryl, —SC(O)-aryl, or —SC(O)-heteroaryl;

In some embodiments where A, E, G, J, L, M, N, or Q independently are —NR$^b$C(O)-aryl, —NR$^b$C(O)-heteroaryl, —NR$^b$SO$_2$-aryl, —NR$^b$SO$_2$heteroaryl, —OC(O)-aryl, —OC(O)-heteroaryl, —OC(O)O-aryl, —OC(O)O-heteroaryl, —OSO$_2$-aryl, —OSO$_2$-heteroaryl, —SC(O)-aryl, or —SC(O)-heteroaryl, the aryl or heteroaryl group can be substituted with one or more substituents, such as (but not limited to) aliphatic, heteroaliphatic, halogen, or a heteroatom-containing functional group, such as aldehyde (—(CH$_2$)$_p$C(O)H), acyl halide (—(CH$_2$)$_p$C(O)X, wherein X is selected from fluorine, chlorine, bromine, and iodine), carbonate (—(CH$_2$)$_p$OC(O)OR$^b$, wherein R$^b$ is hydrogen, aliphatic, heteroaliphatic, aryl, or heteroaryl), carboxyl (—(CH$_2$)$_p$C(O)OH), carboxylate (—(CH$_2$)$_p$COO$^-$), ester (—(CH$_2$)$_p$C(O)OR$^b$), hydroxyl (—(CH$_2$)$_p$OH), ketone (—(CH$_2$)$_p$C(O)R$^b$), peroxy (—(CH$_2$)$_p$OOR$^b$, wherein R$^b$ is hydrogen, aliphatic, heteroaliphatic, aryl, or heteroaryl), hydroperoxy (—(CH$_2$)$_p$OOH), phosphate (—(CH$_2$)$_p$OP(O)OH$_2$), phosphoryl (—(CH$_2$)$_p$P(O)(OH)$_2$), phosphodiester [—(CH$_2$)$_p$(O)$_p$(OH)OR$^b$), wherein R$^b$ is hydrogen, aliphatic, heteroaliphatic, aryl, or heteroaryl], thiol (—(CH$_2$)$_p$SH), disulfide (—(CH$_2$)$_p$SSR$^b$, wherein R$^b$ is hydrogen, aliphatic, heteroaliphatic, aryl, or heteroaryl), sulfonate (—(CH$_2$)$_p$SO$_3^-$), sulfinyl (—(CH$_2$)$_p$S(O)R$^b$, wherein R$^b$ is hydrogen, aliphatic, heteroaliphatic, aryl, or heteroaryl), sulfonate ester (—(CH$_2$)$_p$SO$_2$OR$^b$, wherein R$^b$ is hydrogen, aliphatic, heteroaliphatic, aryl, or heteroaryl), sulfonyl (—(CH$_2$)$_p$SO$_2$R$^b$, wherein R$^b$ is hydrogen, aliphatic, heteroaliphatic, aryl, or heteroaryl), carbonothioyl (—(CH$_2$)$_p$C(S)R$^b$ or —(CH$_2$)$_p$C(S)H, wherein R$^b$ is hydrogen, aliphatic, heteroaliphatic, aryl, or heteroaryl), sulfino (—(CH$_2$)$_p$S(O)OH), sulfo (—(CH$_2$)$_p$SO$_3$H), thiocyanate (—(CH$_2$)$_p$SCN), isothiocyanate (—(CH$_2$)$_p$NCS), oxazole, oxadiazole, imidazole, triazole, tetrazole, amide (—(CH$_2$)$_p$C(O)NR$^b$R$^c$, wherein R$^b$ and R$^c$ independently are hydrogen, aliphatic, heteroaliphatic, aryl, or heteroaryl), azide (—(CH$_2$)$_p$N$_3$), azo (—(CH$_2$)$_p$NNR$^b$, wherein R$^b$ is hydrogen, aliphatic, heteroaliphatic, aryl, or heteroaryl), isocyanate (—(CH$_2$)$_p$NCO), imide (—(CH$_2$)$_p$C(O)NR$^b$C(O)R$^c$, wherein R$^b$ and R$^c$ independently are hydrogen, aliphatic, heteroaliphatic, aryl, or heteroaryl), nitrile (—(CH$_2$)$_p$CN), isonitrile (—(CH$_2$)$_p$N$^+$≡C$^-$), nitro (—(CH$_2$)$_p$NO$_2$), nitroso (—(CH$_2$)$_p$NO), nitromethyl (—(CH$_2$)$_p$CH$_2$NO$_2$), or —(CH$_2$)$_p$NH$_2$, wherein each p independently is an integer selected from 0 to 10. In particular disclosed embodiments, one or more of the substituents can be used to append a support component as described herein.

In some embodiments, the variables of Formula I can be as recited below:

each of A, E, G, and J independently can be —NH$_2$, —N(C$_1$-C$_{10}$alkyl)$_2$, Cl, F, Br, or I, —SO$_3^-$, —CO$_2^-$, —(CH$_2$)$_p$Ph(CH$_2$)$_p$(Y)$_m$, —NHC(O)Ph(CH$_2$)$_p$(Y)$_m$, —NHSO$_2$Ph(CH$_2$)$_p$(Y)$_m$, —OC(O)Ph(CH$_2$)$_p$(Y)$_m$, or —OSO$_2$Ph(CH$_2$)$_p$(Y)$_m$; wherein each Y independently can be positioned ortho, meta, or para on the phenyl group and can be selected from aliphatic, aryl, halogen, heteroaliphatic, heteroaryl, or a heteroatom-containing function group, or a combination thereof, m can be an integer selected from 0 to 4, and p can be an integer selected from 0 to 10;

each L, M, N, and Q independently can be —OH, —O(CH$_2$)$_p$Ph(CH$_2$)$_p$(Y)$_m$, —O$^-$, —OC(O)Ph(CH$_2$)$_p$(Y)$_m$, —O(CH$_2$)$_p$Y, or —OSO$_2$Ph(CH$_2$)$_p$(Y)$_m$; wherein each Y independently can be positioned ortho, meta, or para on the phenyl ring and can be selected from aliphatic, aryl, halogen, heteroaliphatic, heteroaryl, or a heteroatom-containing function group, or a combination thereof, and m can be an integer selected from 0 to 4; and each of $X^1$, $X^2$, $X^3$, and $X^4$ independently can be $CH_2$ or S.

In particular disclosed embodiments, Y can be alkyl, alkoxy, amide, thiol, thioether, aldehyde, carboxyl, ester, —(CH$_2$)$_p$CO$_2$H (wherein p is an integer selected from 0 to 10), —(CH$_2$)$_p$NH$_2$ (wherein p is an integer selected from 0 to 10), —(CH$_2$)$_p$NH$_3^+$ (wherein p is an integer selected from 0 to 10), Br, Cl, F, or I.

In particular disclosed embodiments, the compounds can have a structure satisfying any one or more of the formulas illustrated below.

TABLE 1

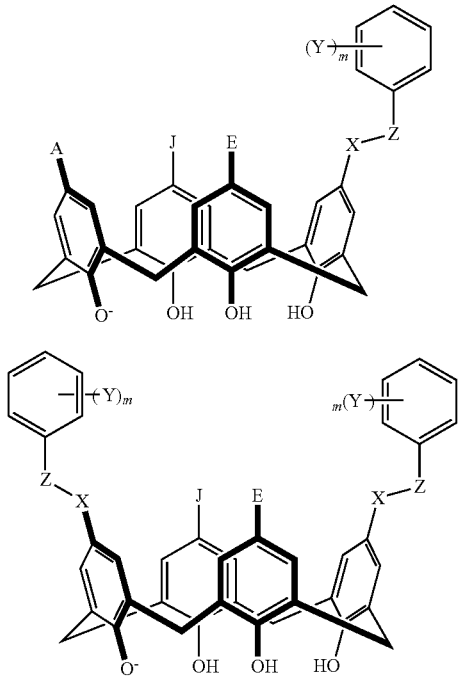

TABLE 1-continued
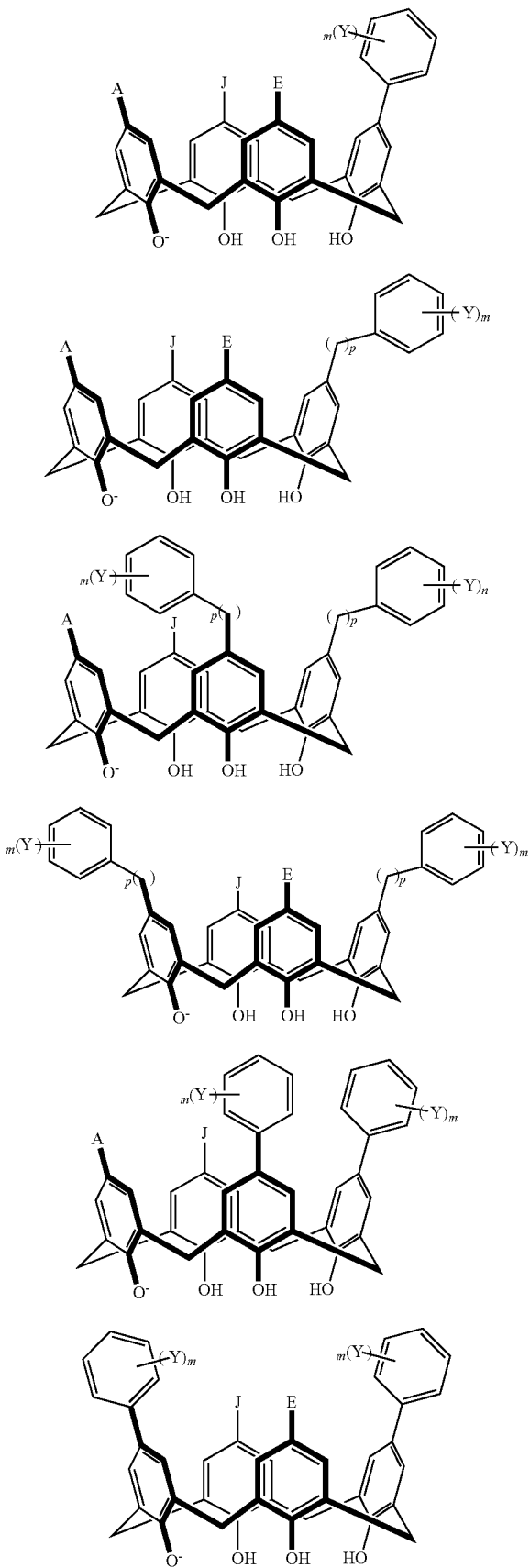
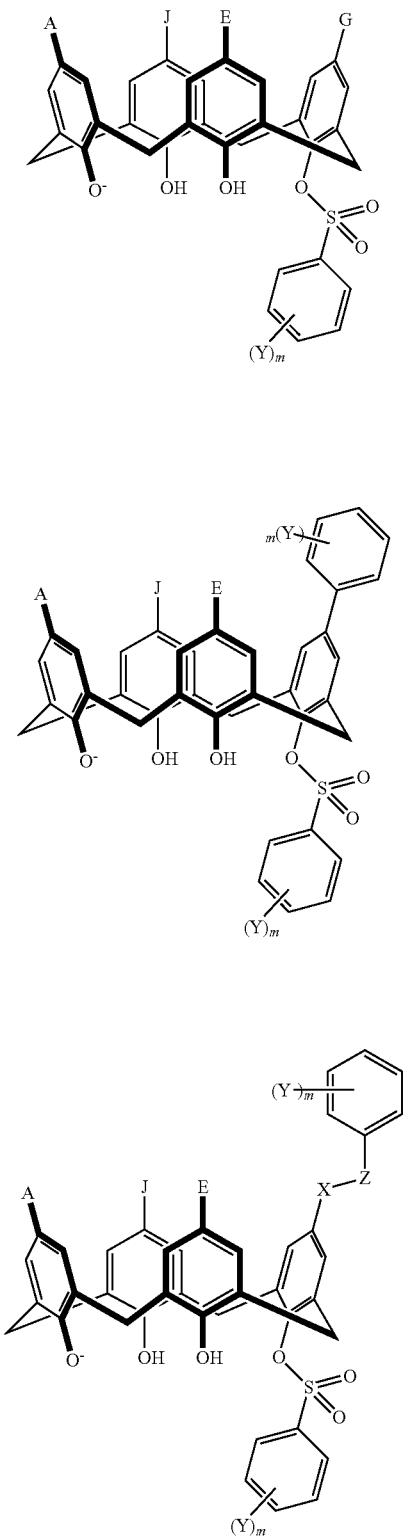

TABLE 1-continued
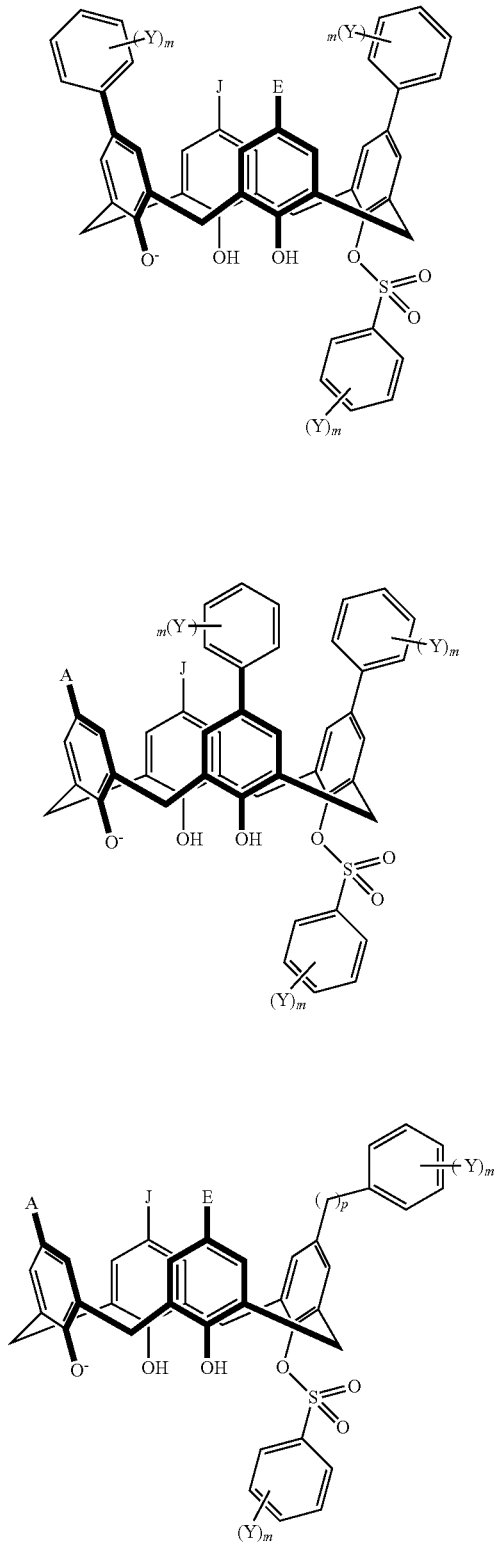
TABLE 1-continued
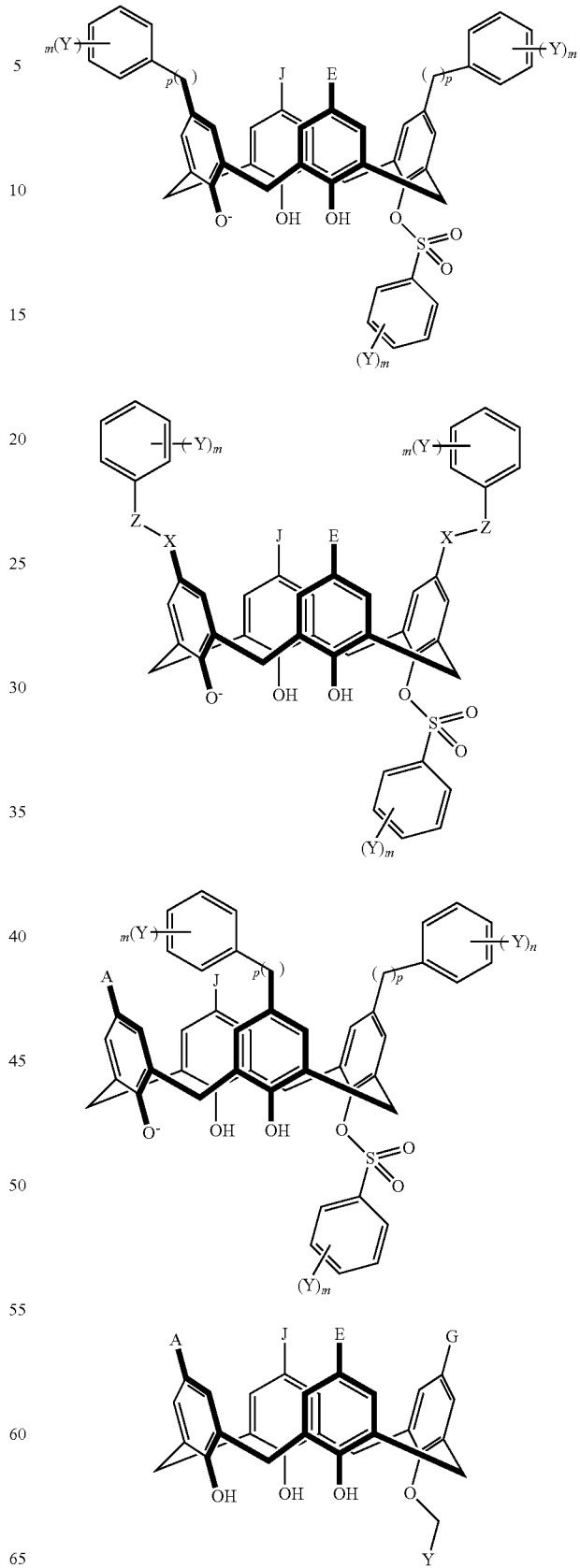

TABLE 1-continued

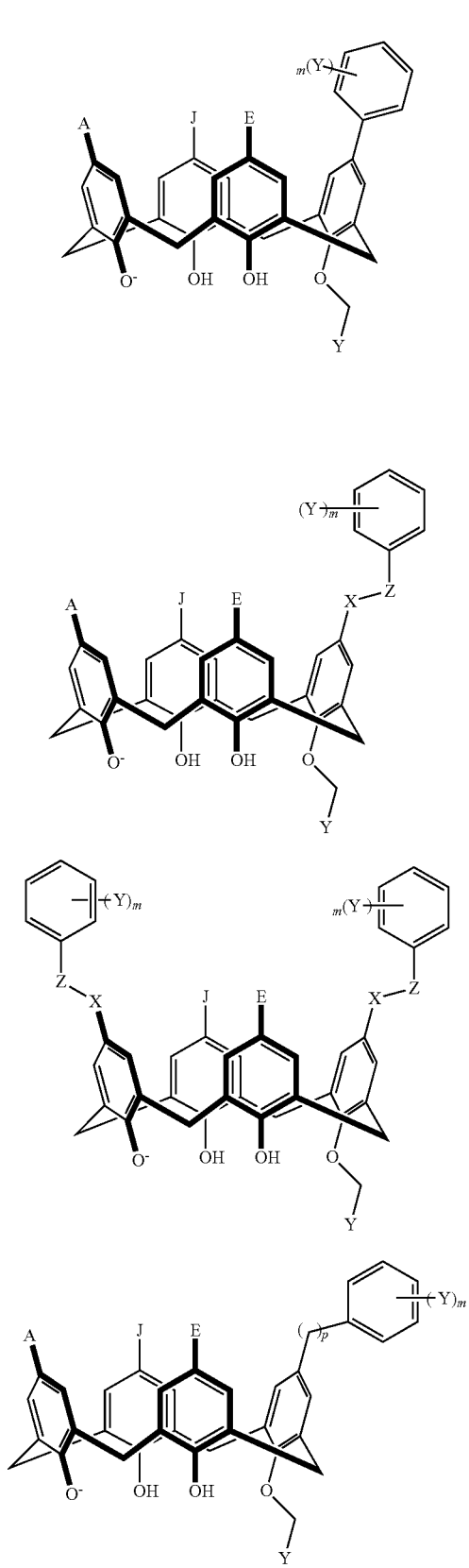

TABLE 1-continued

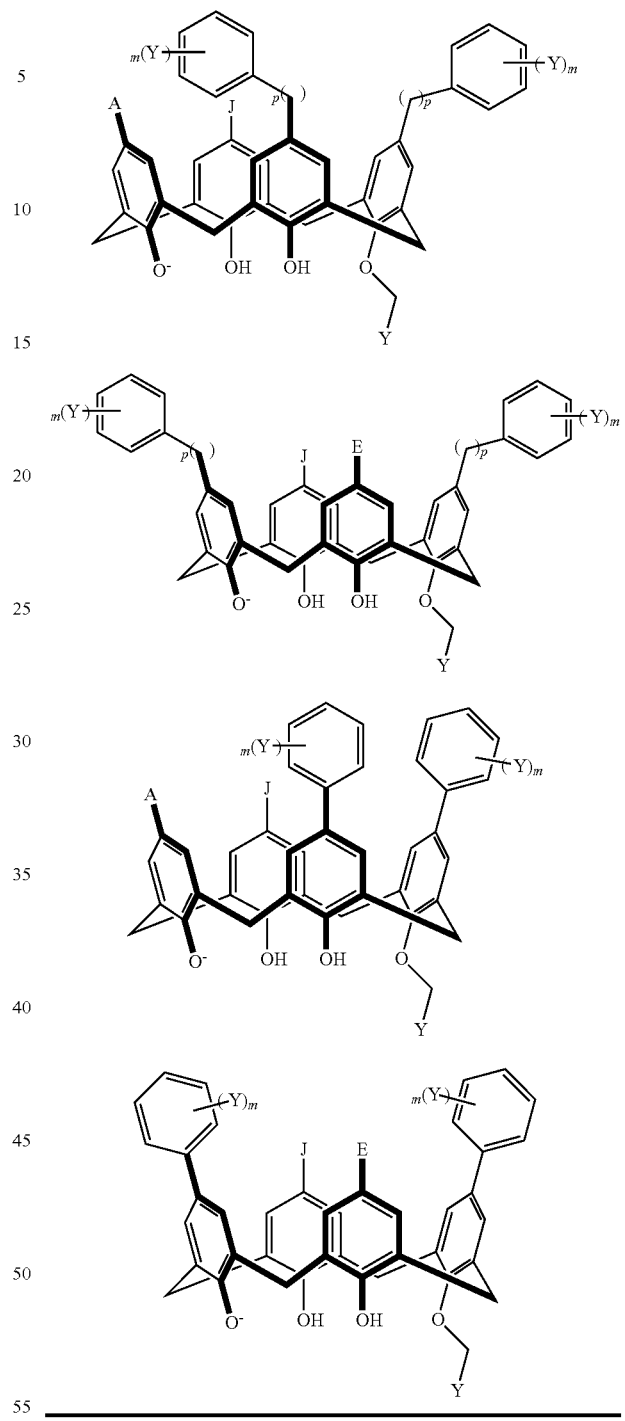

With reference to the formulas of Table 1, each X independently can be nitrogen, oxygen, carbon, or sulfur; each Z independently can be —$SO_2$—, —CO—, or —C(O)O—; each Y independently can be as described above; each m independently can be an integer selected from 0 to 5; each p independently can be an integer selected from 0 to 10; and each of A, J, and G are as recited above.

In yet additional embodiments, the compounds can have structures satisfying any one or more of the formulas illustrated below in Table 2.

TABLE 2
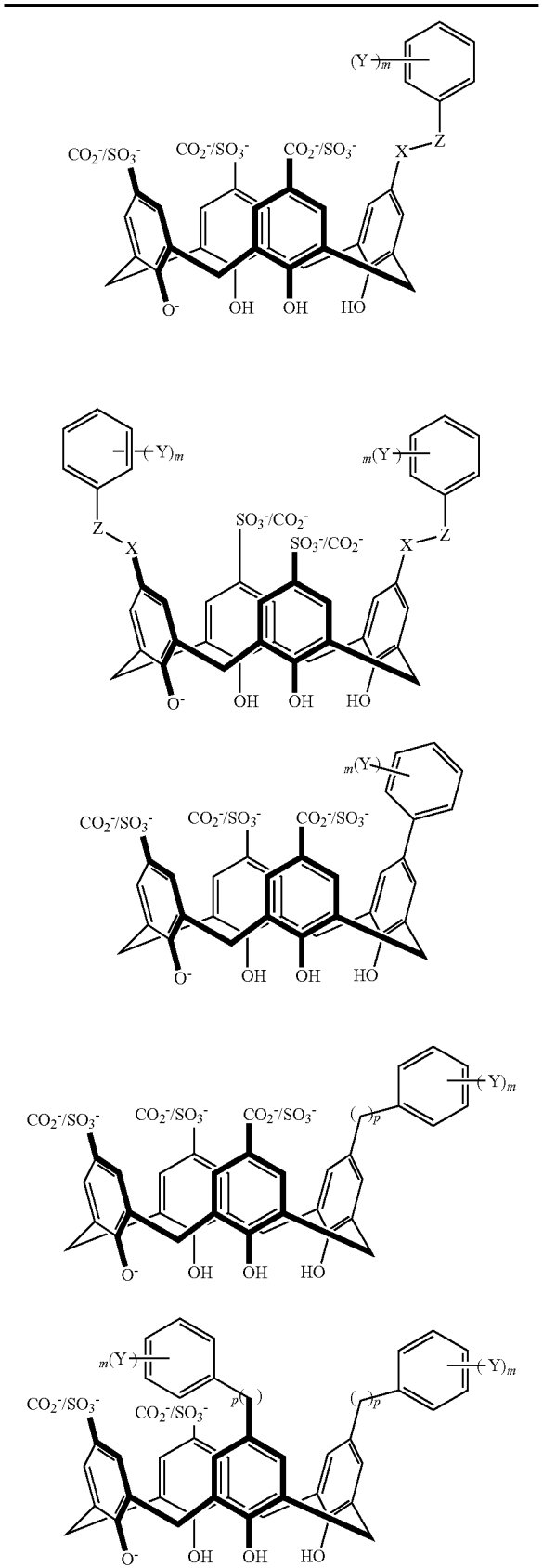
TABLE 2-continued
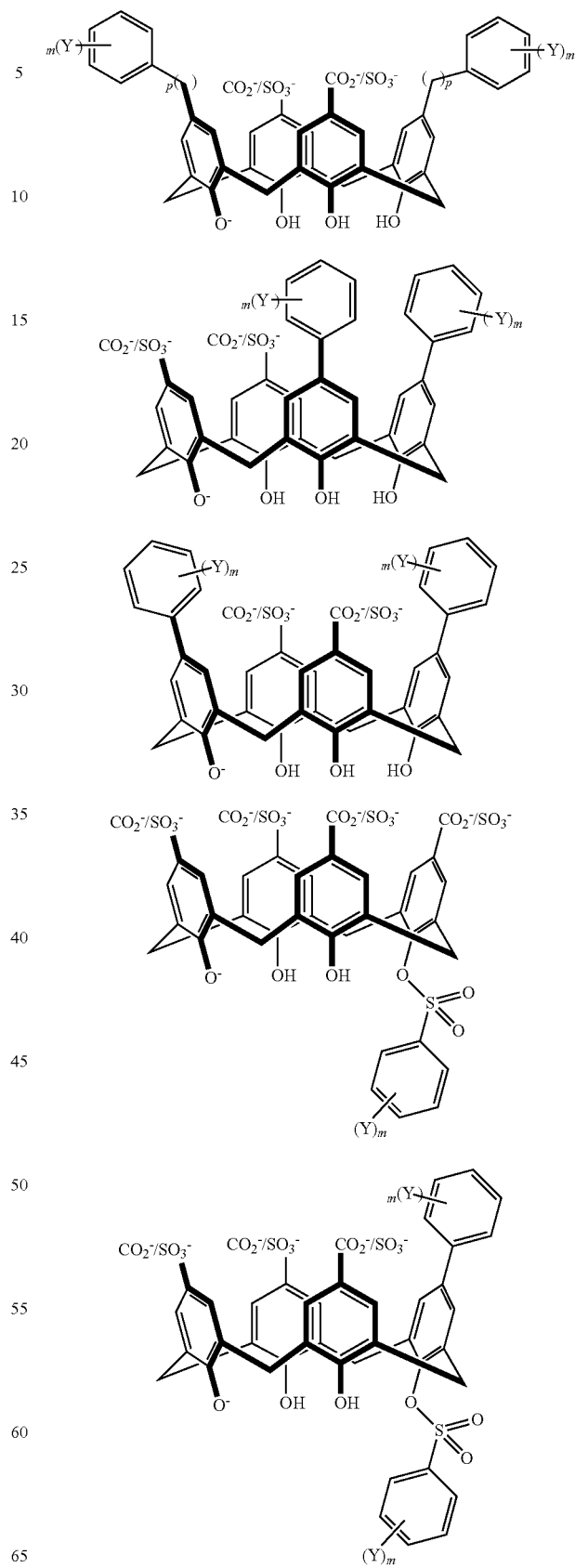

TABLE 2-continued
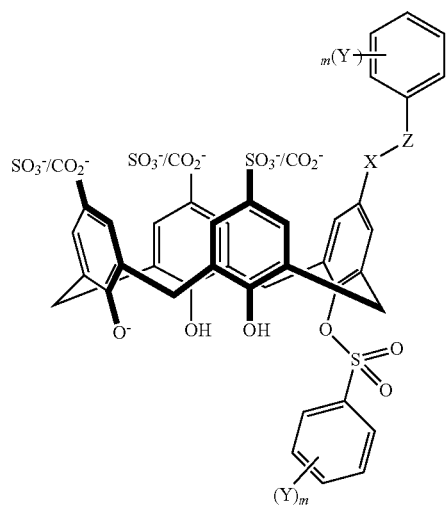
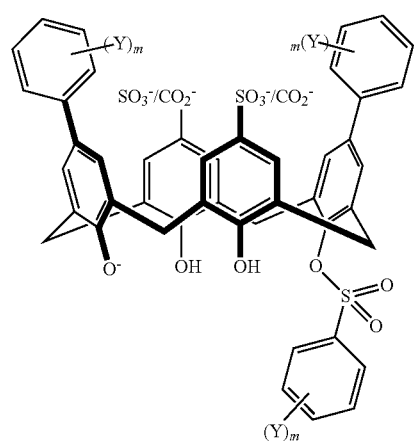
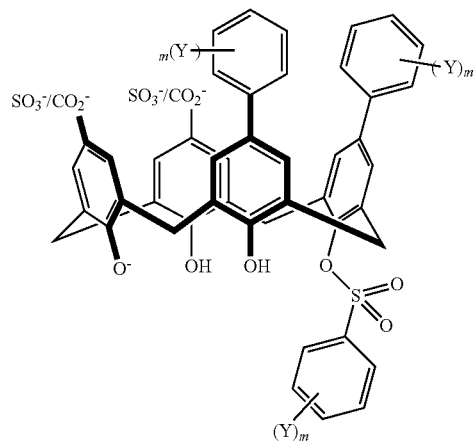
TABLE 2-continued
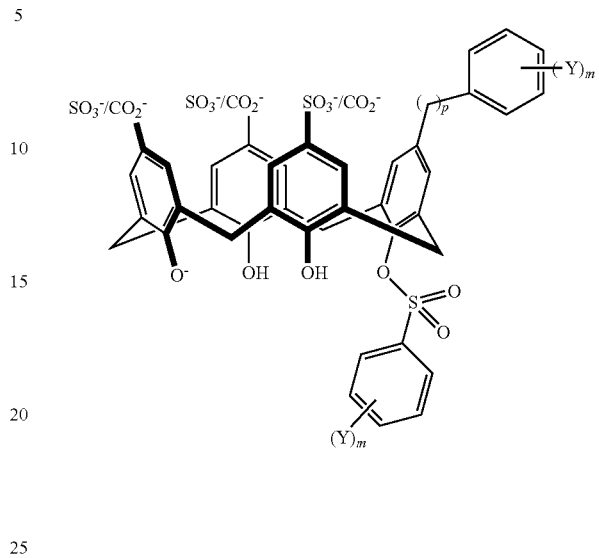
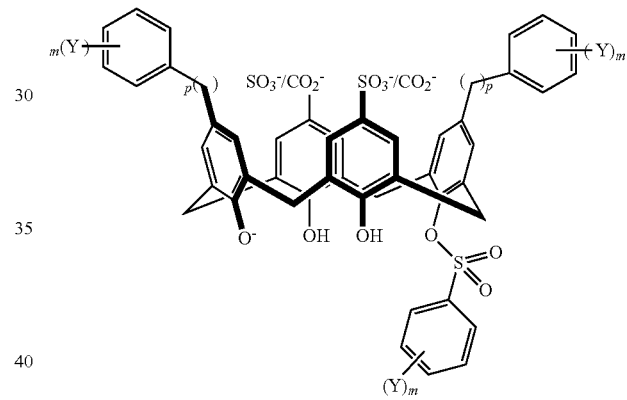
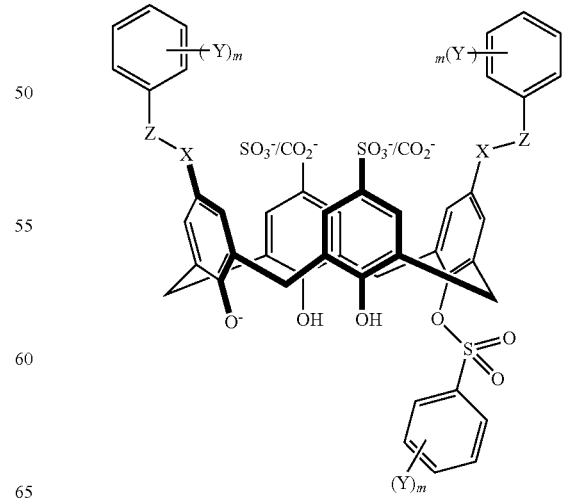

TABLE 2-continued

TABLE 2-continued
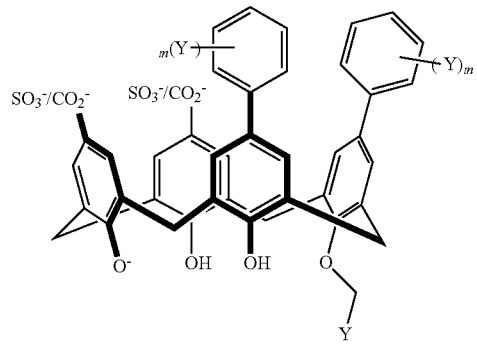
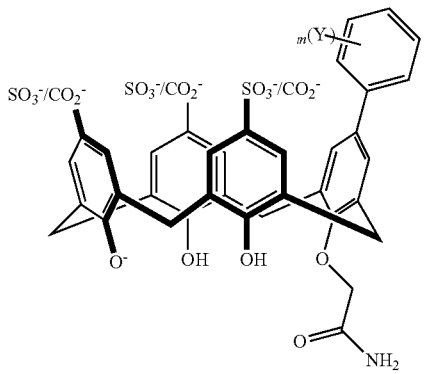
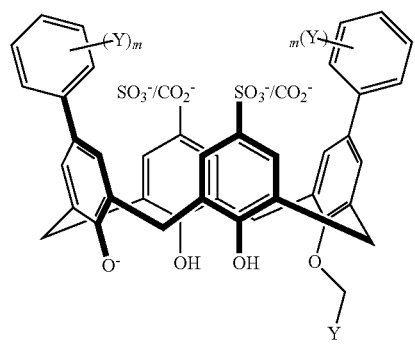
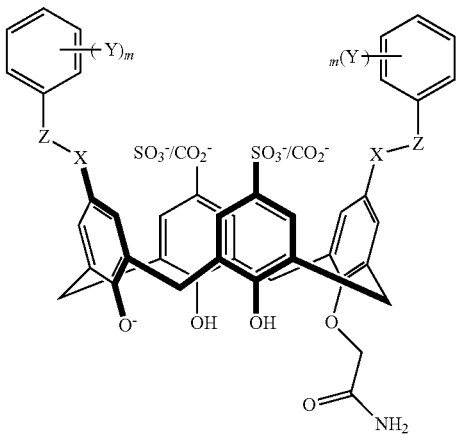
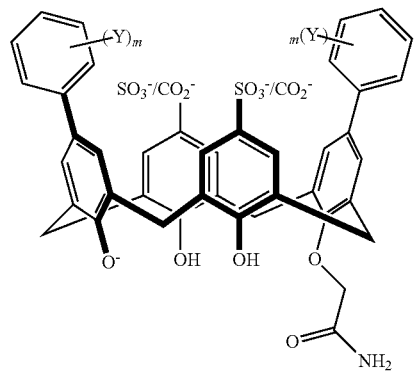
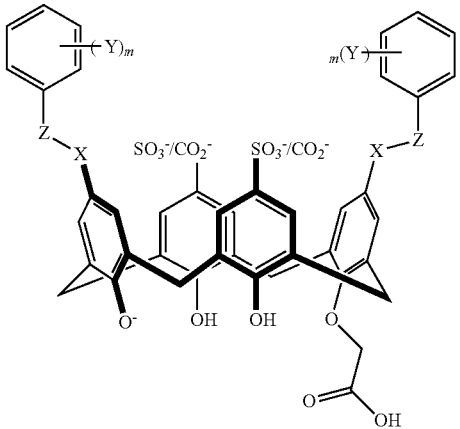
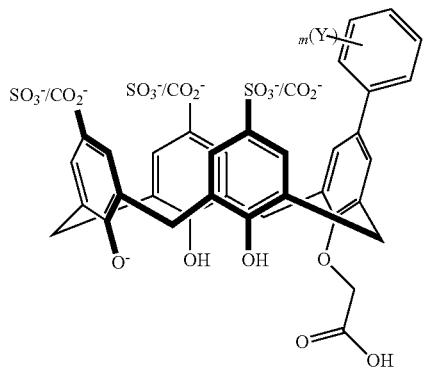
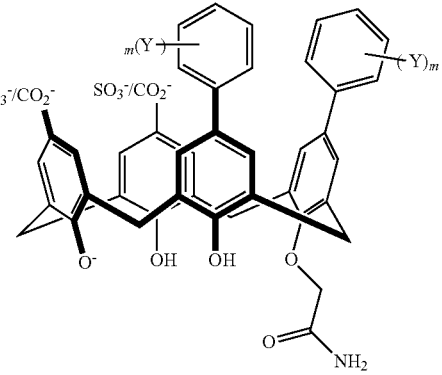

TABLE 2-continued
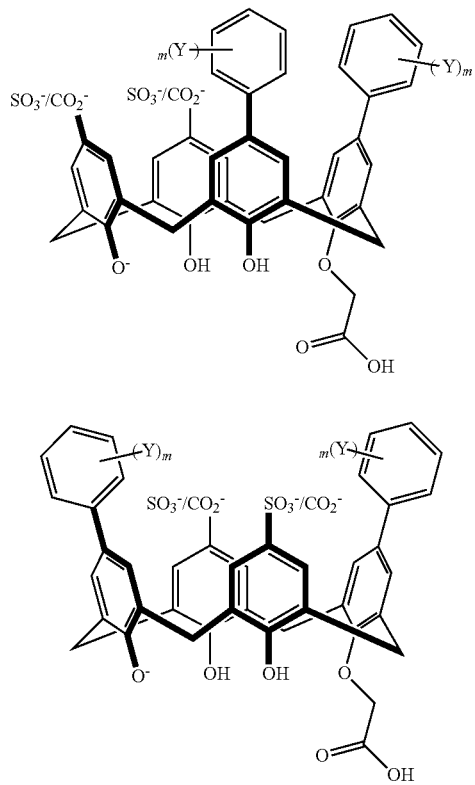
With reference to the formulas of Table 2, each of X, Y, Z, m, and p can be as recited above in Table 1 and "$CO_2^-$/$SO_3^-$" indicates that either a $CO_2^-$ or a $SO_3^-$ group is attached at the indicated position.
Representative compounds that can be used in conjugates and methods described herein are illustrated in Table 3.
TABLE 3
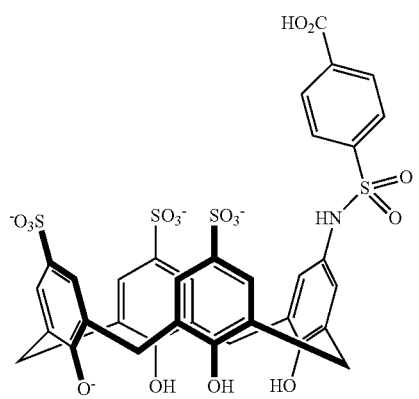
TABLE 3-continued
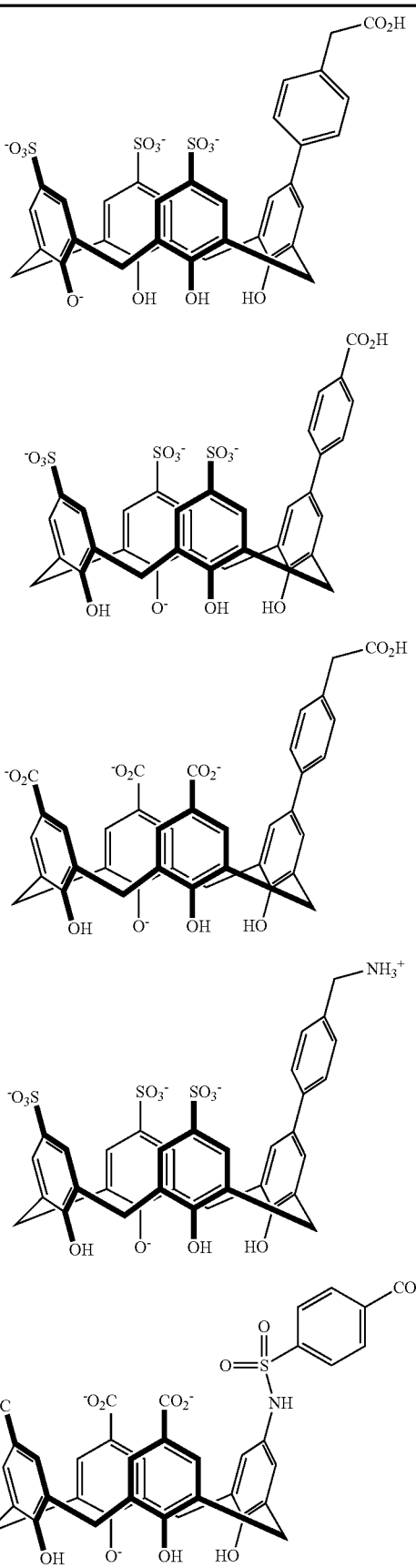

TABLE 3-continued
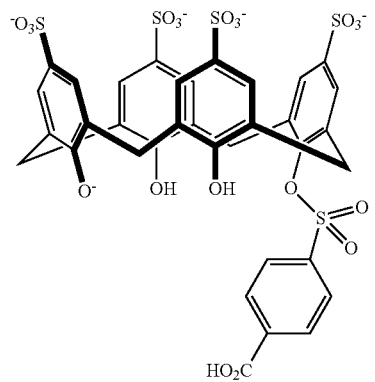
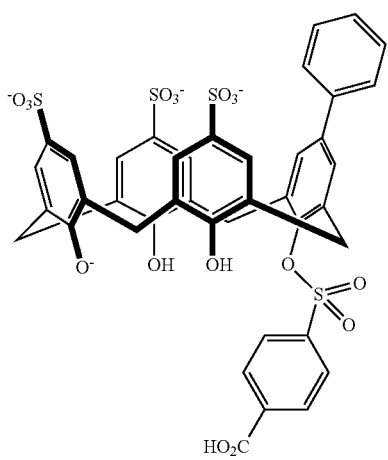
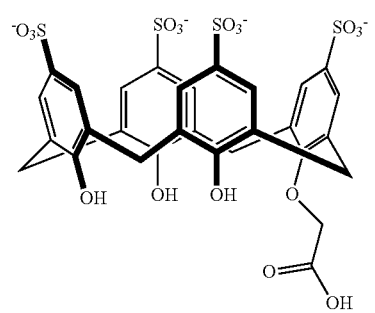
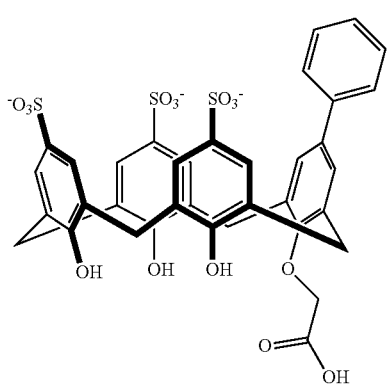
TABLE 3-continued
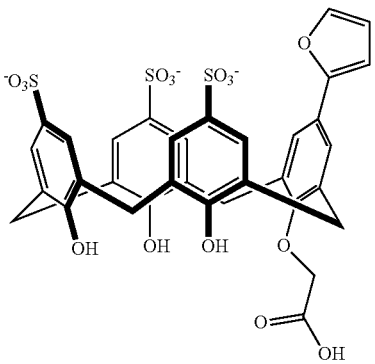
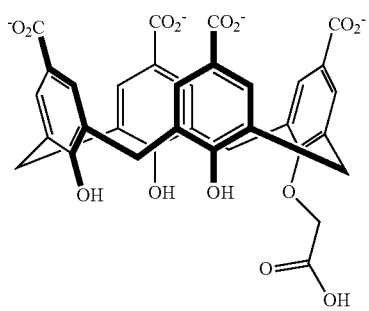
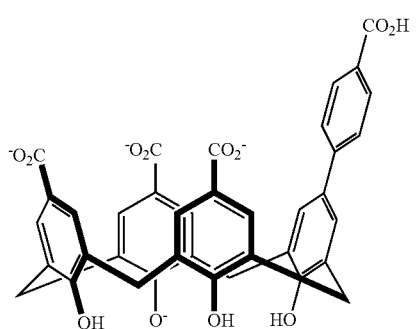
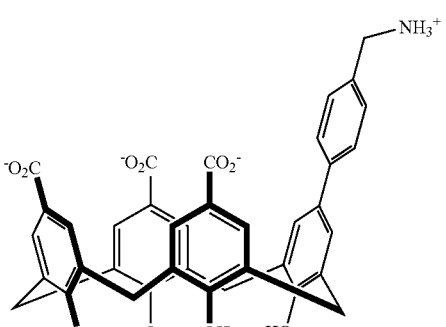

In an independent embodiment, the compound is not or is other than:

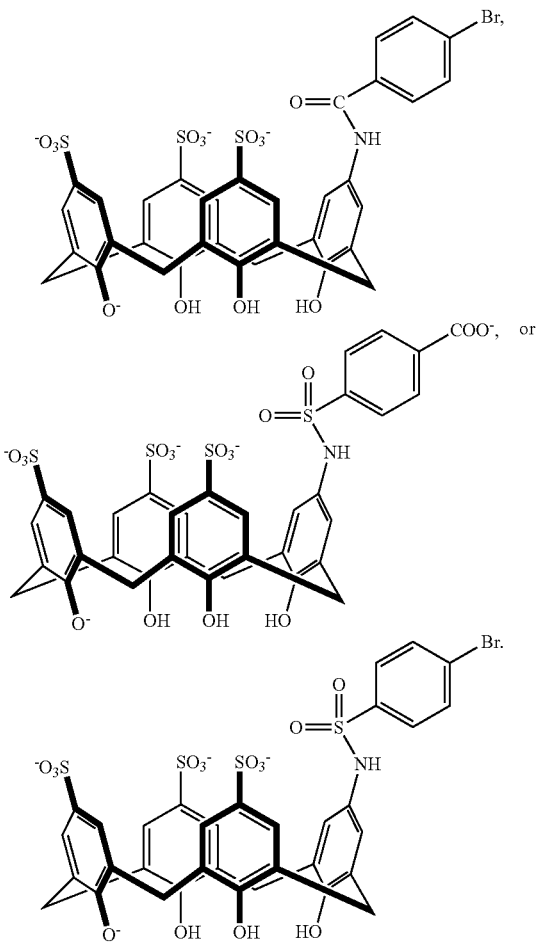

In particular disclosed embodiments, any of the compounds disclosed herein can used to form conjugates. The conjugates can comprise any one or more of the compounds disclosed herein and a support component. In some embodiments, the support component can be a solid support. Representative support components include, but are not limited to, resins, beads, polymeric matrices, metal oxide supports, powders, crystalline solids, amorphous solids, gels, and the like. In particular disclosed embodiments, the support component can be (but is not limited to) agarose, sepharose, cellulose, modified cellulose, dextran, polyacrylamide, polystyrene, latex, bonded silica gel, silica based solid, activated alumina, polysaccharide polymers or resinous polymers. The compound(s) and support component can be coupled together covalently or non-covalently. In particular disclosed embodiments, the compound(s) and the support component are coupled covalently. The support component can be coupled directly to a functional group of the compound, or it can be coupled indirectly, such as through a linker compound. Suitable linkers include, but are not limited to, aliphatic linkers, heteroaliphatic linkers, heteroatom-containing functional group linkers, aryl linkers, or heteroaryl linkers.

In particular disclosed embodiments, the conjugate can have a structure satisfying Formula II:

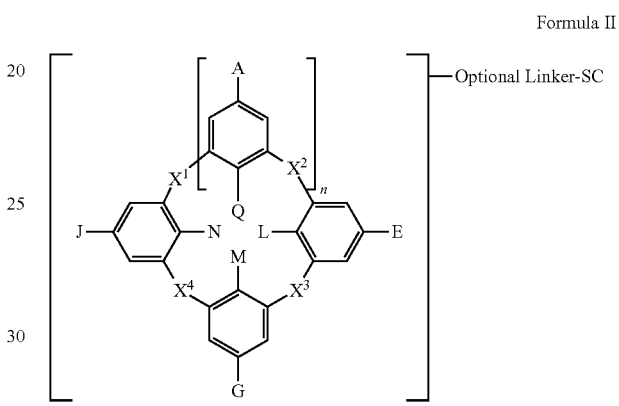

Formula II wherein each of A, E, G, J, L, M, N, Q, $X^1$, $X^2$, $X^3$, $X^4$, and n can be as recited herein; the optional linker, if present, can be an aliphatic linker, a heteroaliphatic linker, a heteroatom-containing functional group linker, an aryl linker, or a heteroaryl linker; and SC is a support component as described above. As represented by brackets of Formula II, the support component can be coupled at any suitable position of the compound and can be coupled directly to the compound (such that the optional linker is not present) or can be coupled indirectly to the compound through the optional linker. In some embodiments, the support component can be coupled to one or more of A, E, G, J, L, M, N, or Q. In particular disclosed embodiments, the support component is coupled to one or more of A, E, G, or J.

In some embodiments, the conjugate can have a structure satisfying any one or more of the following formulas illustrated below in Table 4.

TABLE 4

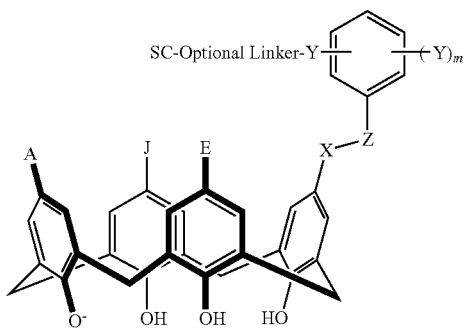

TABLE 4-continued
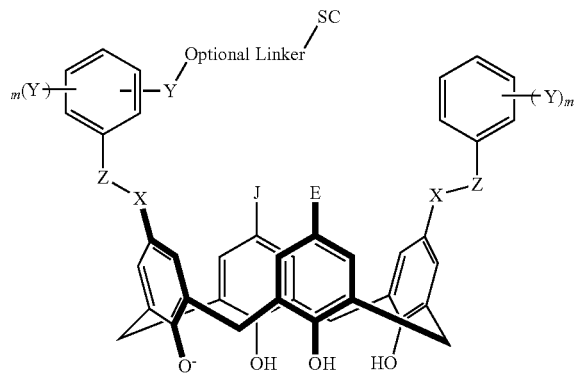
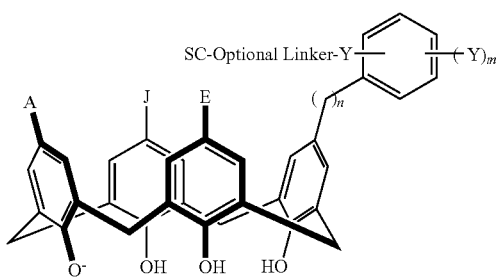
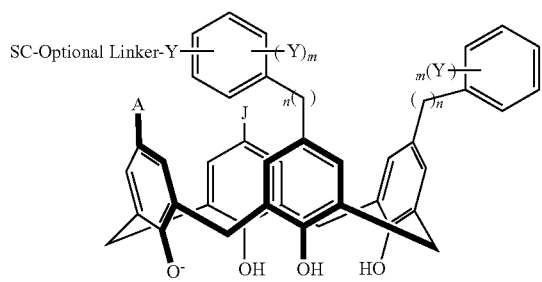
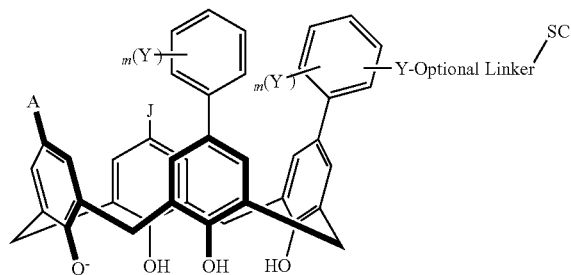
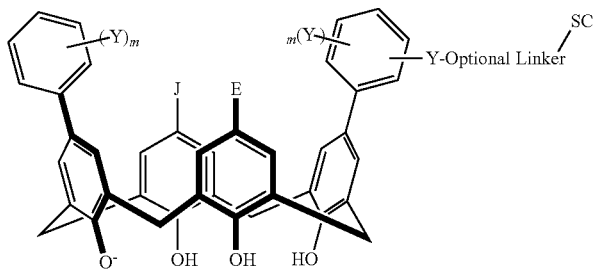

TABLE 4-continued
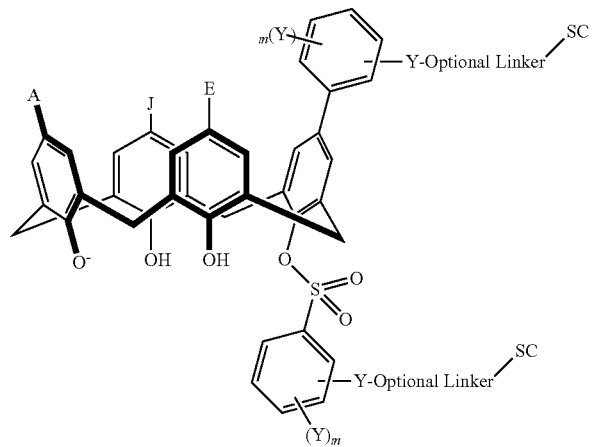
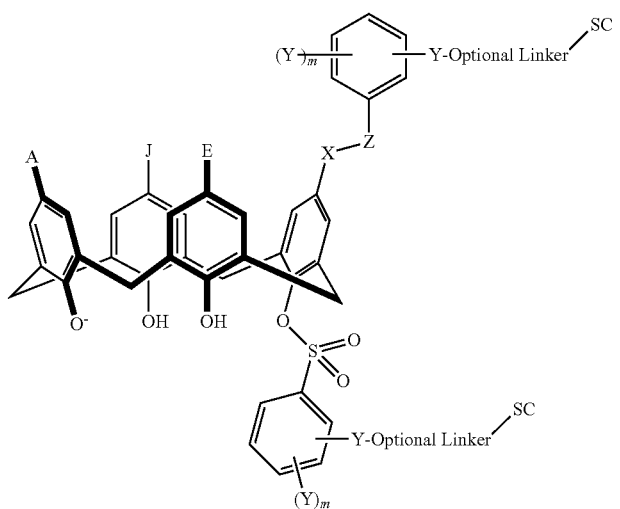
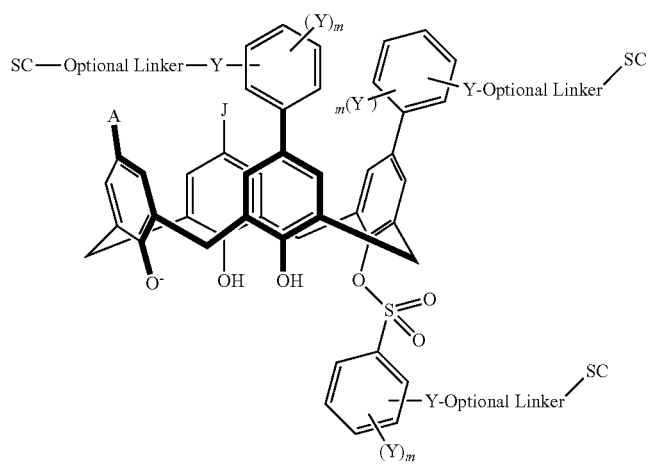

TABLE 4-continued
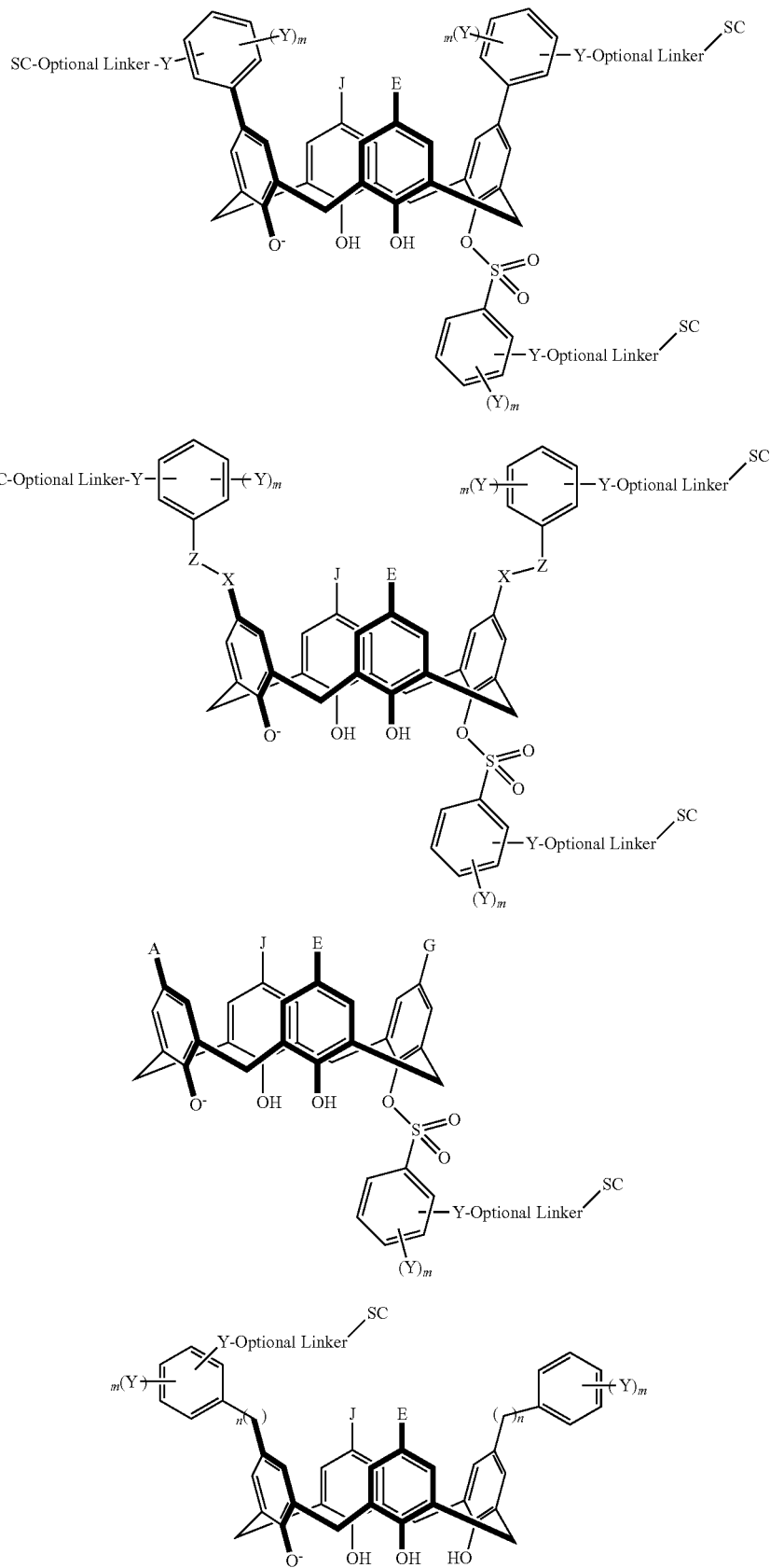

TABLE 4-continued
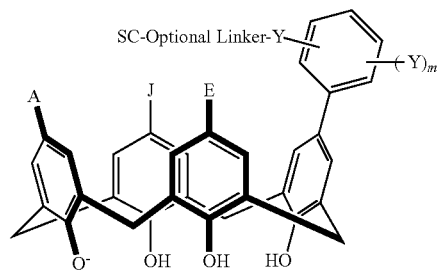
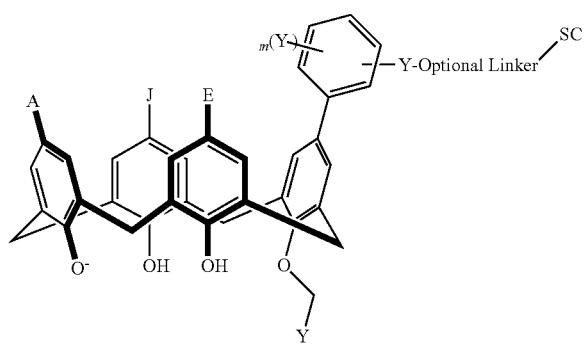
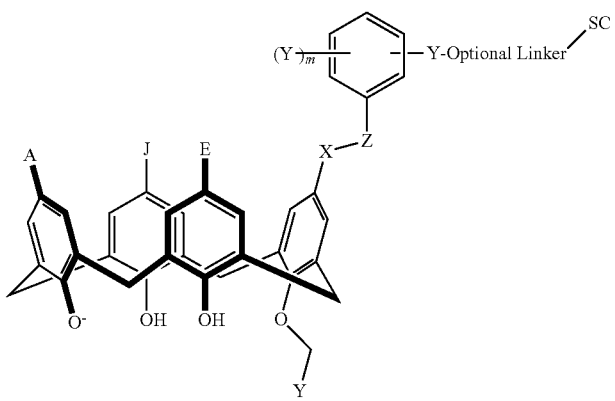
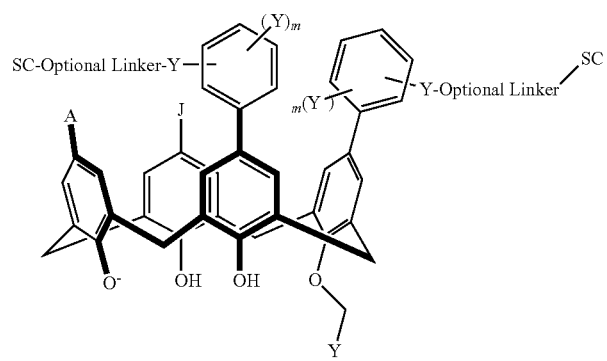

TABLE 4-continued
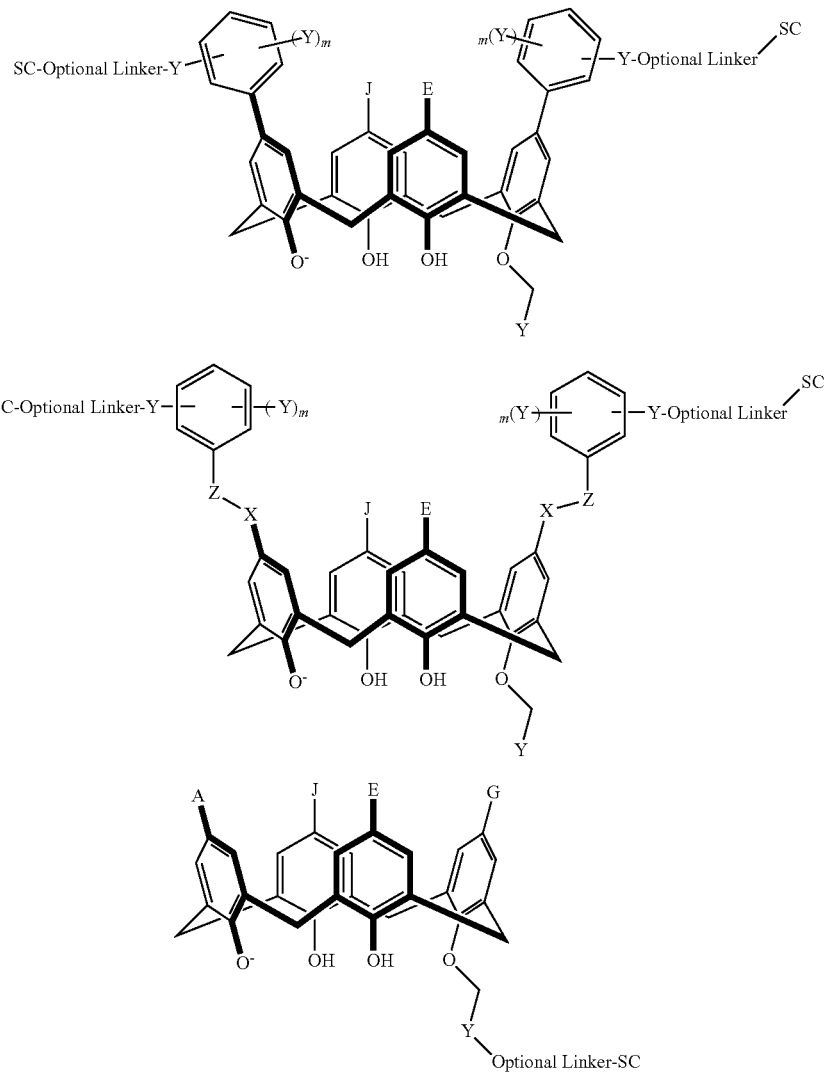
wherein each of X, Y, Z, m, n, optional linker, and SC are as recited above in Formula II.
Exemplary conjugates are provided below in Table 5.
TABLE 5
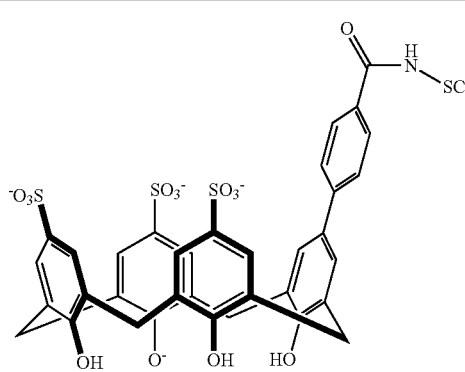
TABLE 5-continued
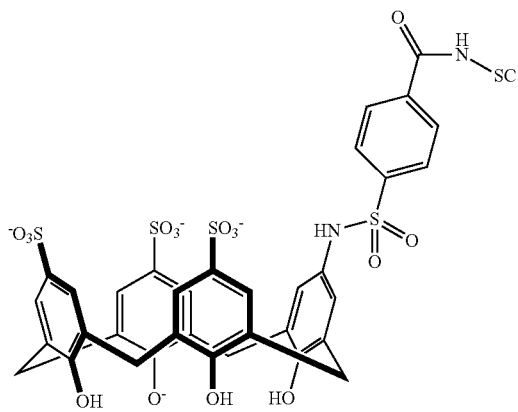

TABLE 5-continued
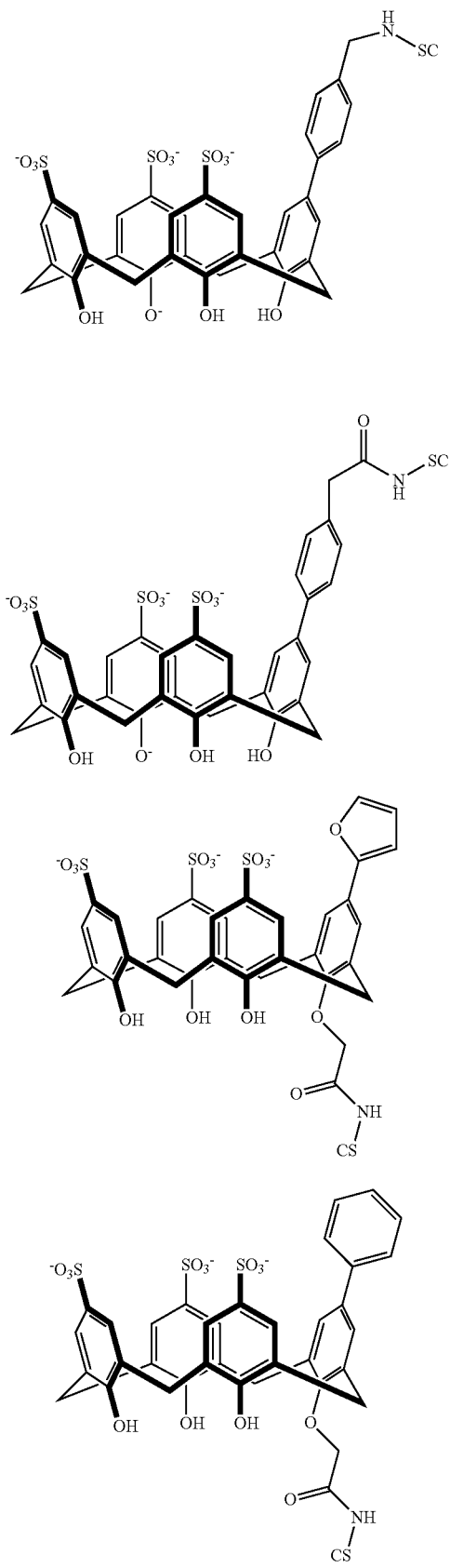
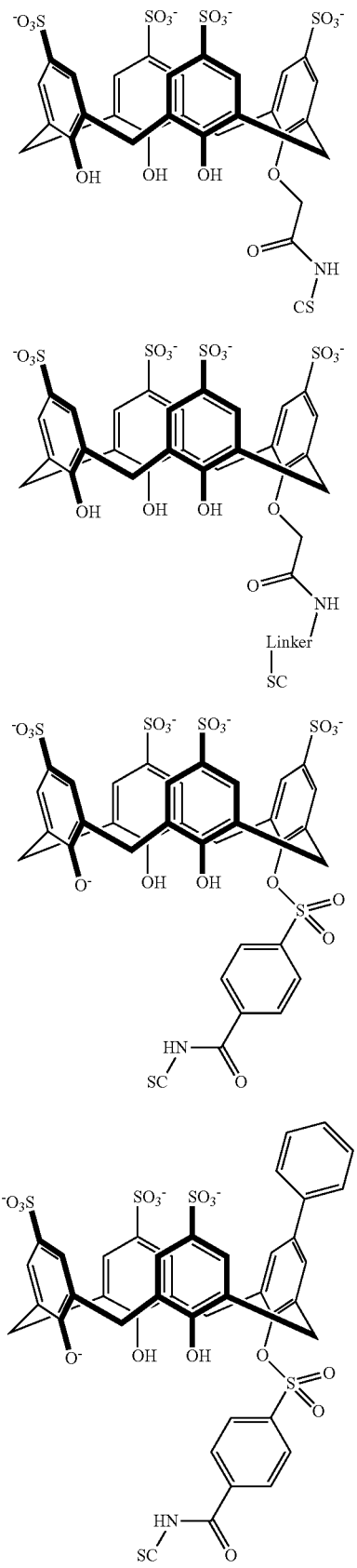

TABLE 5-continued
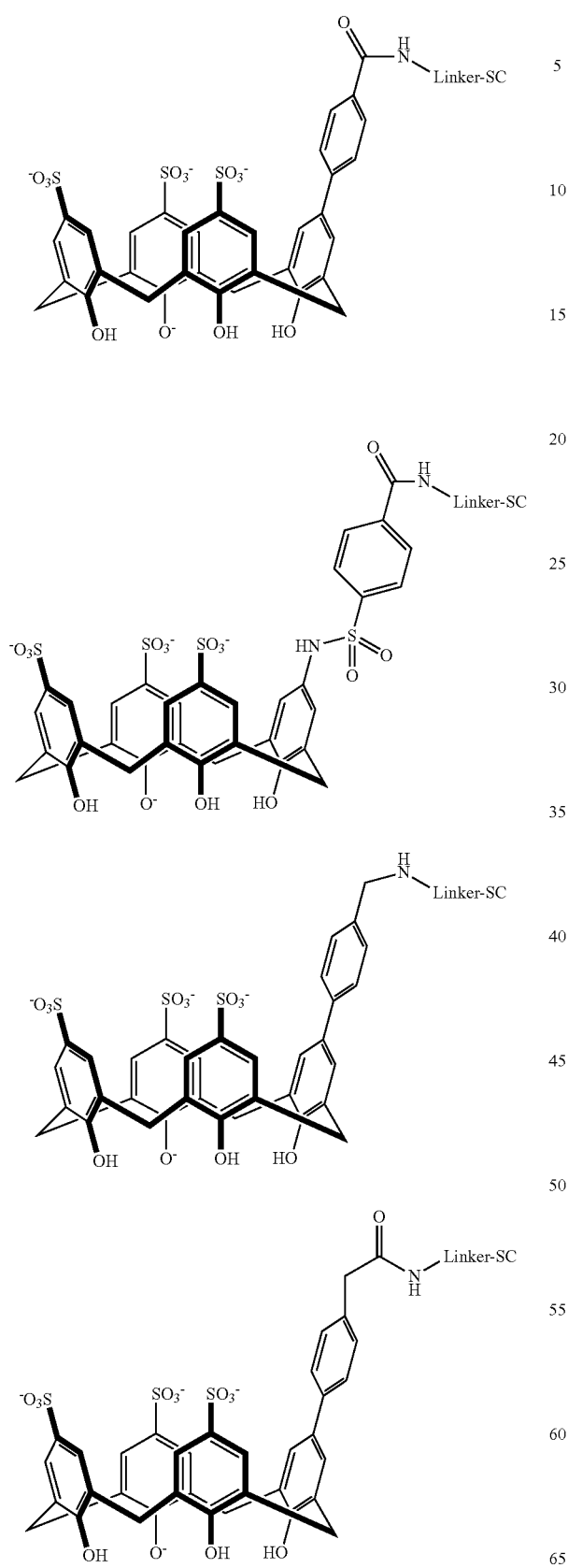
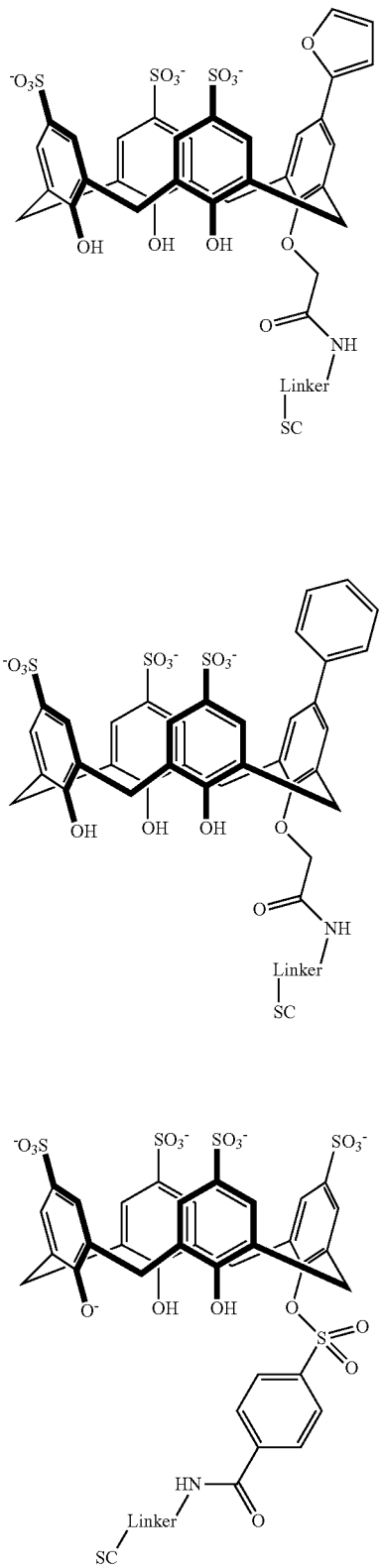

TABLE 5-continued

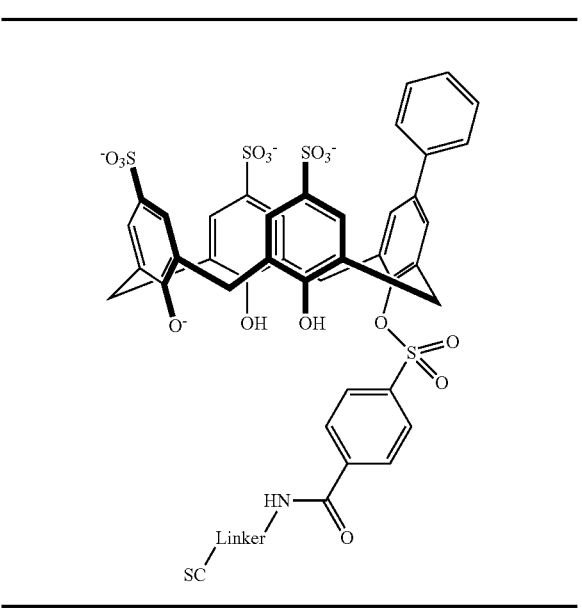

wherein the linker can be as recited above and SC corresponds to the support component.

IV. Methods for Making Compounds

Also disclosed herein are embodiments of methods for making the compounds disclosed herein. In particular disclosed embodiments, the methods can comprise making precursor compounds that can be converted to functionalized compounds that can be coupled with a support component.

In particular disclosed embodiments, a starting material 100 can be converted to a precursor compound 104 by protecting reactive functional groups on the compound and then substituting one or more rings of the starting material with a functional group that can be further modified to provide a desired functionalized compound (Scheme 1). In particular disclosed embodiments, the protection step can be performed selectively so as to provide one or more non-protected reactive functional groups to thereby activate the ring to which the non-protected reactive functional group is attached. Such non-protected reactive functional groups also can be used to append a moiety that can be coupled to a support component as described herein. Suitable functional groups include, but are not limited to, halogen (e.g., bromo, chloro, fluoro, or iodo), nitro, boronic acid or ester, azide, or the like. In some embodiments, the methods can further comprise exposing the precursor compound to a reagent capable of sulfonated and/or carboxylating one or more rings of the compound, such as is illustrated in Scheme 1.

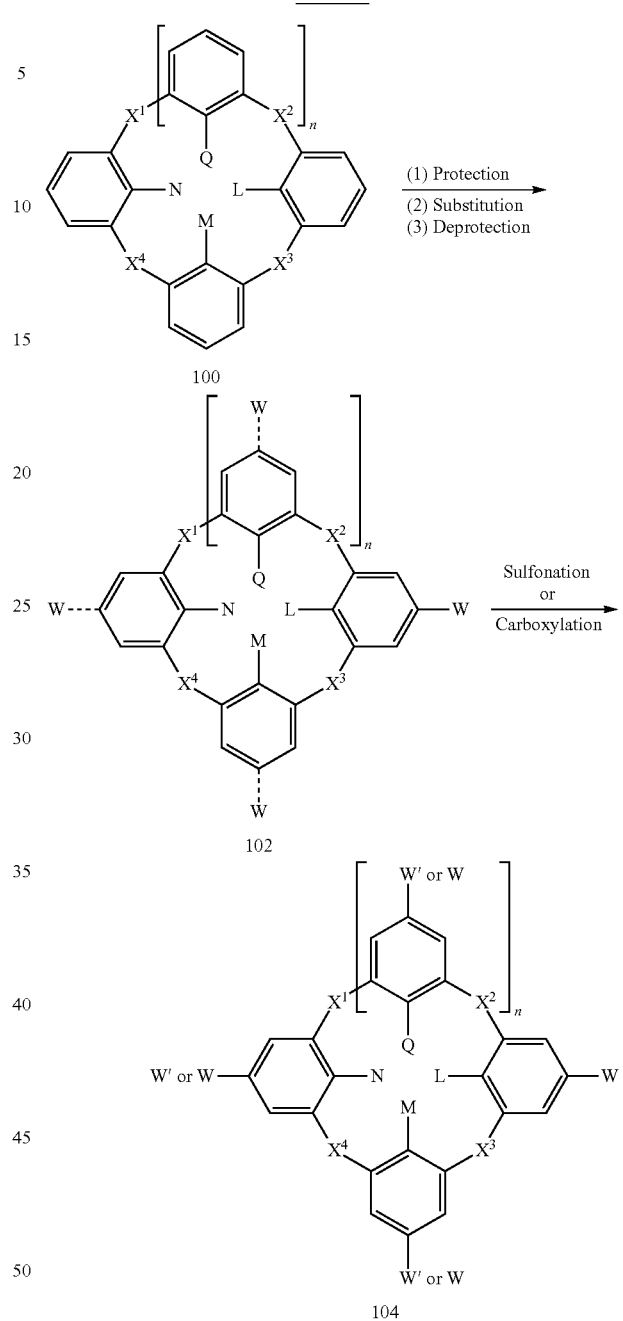

With reference to Scheme 1, one or more functional groups can be added to the precursor compound, but not all rings of the starting material need be functionalized with the functional group (as indicated by the dashed bonds illustrated for intermediate 102). In some embodiments, at least one ring of the precursor compound is not functionalized so that a sulfonate or carboxylate group (represented W' as illustrated in Scheme 1) can be added to the ring of the precursor compound. In particular disclosed embodiments, a plurality of carboxylate and/or sulfonate groups can be added to the precursor compound (Scheme 1, compound 104). Also, with reference to Scheme 1, each of M, N, L, Q, n and $X^1$-$X^4$ can be as recited above; each W group independently can be a halogen, a boronic acid, a boronic ester, or a nitro group; and each W' group independently can be a sulfonate or carboxylate group.

A representative method for making compounds disclosed herein is illustrated in Scheme 2. With reference to Scheme 2, bromo- and nitro-functionalized precursors 204 and 206 and can be made by tribenzoylation of the four lower rim phenols of starting compound 200 to produce one uniquely activated ring in the macrocycle as with compound 202. This ring can be reacted with either bromine or nitric acid, and subsequent basic hydrolysis of the benzoyl groups produced the desired monofunctionalized intermediates (Scheme 2A). Brominated compound 204 can then be sulfonated at the remaining para positions along the upper rim through treatment with $H_2SO_4$ to yield the monobromo, trisulfonate Suzuki coupling precursor compound 208 (Scheme 2B). The nitro-bearing compound 206 can be similarly sulfonated and then hydrogenated using $H_2$ and Raney nickel to yield the monoamino, trisulfonate compound 210 (Scheme 2C).

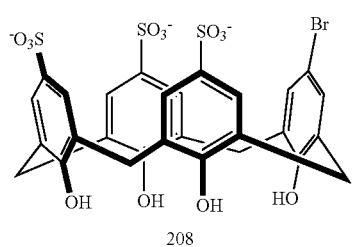
208

Scheme 2A

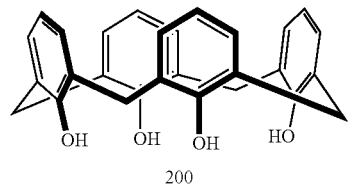
200

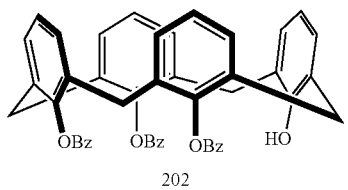
202

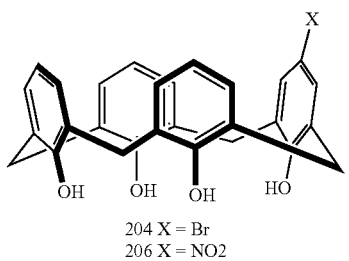
204 X = Br
206 X = NO2

Scheme 2B

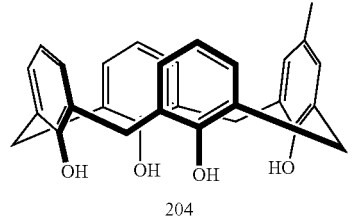
204

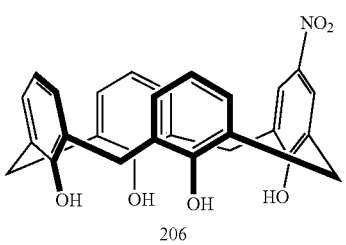
204

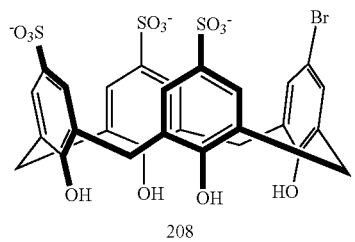
208

Scheme 2C

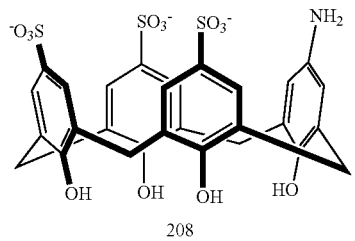
208

Once a sulfonated or carboxylated precursor compound, such as compound 104, is obtained, it can be converted to a functionalized compound 300 by reacting the functional group capable of further modification with an appropriate coupling reagent (Scheme 3). In some embodiments, the functionalized compound can be made using metal-mediated couplings or substitution reactions. With reference to Scheme 3, each W can be converted to a corresponding A, E, G, or J group, wherein the A, E, G, or J group is as recited herein. Any W' groups present on the precursor compound 104 will remain unfunctionalized.

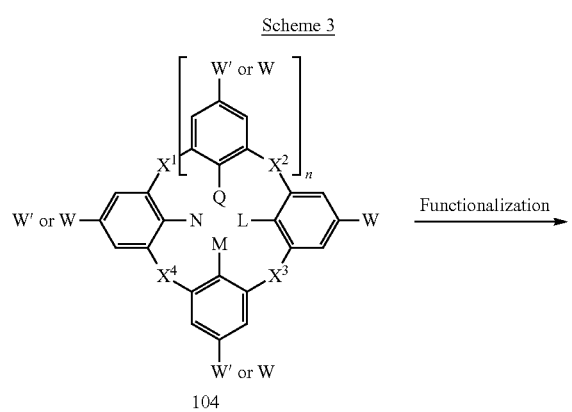

Scheme 3

Representative methods wherein a precursor compound is converted to a functionalized compound are illustrated in Schemes 4 and 5. Specifically, compounds 402-406 are made using a Suzuki coupling of a suitable functionalized boronic acid 400 to the precursor 208 under aqueous conditions at 150° C. in a sealed tube (Scheme 4). Compound 502, containing a sulfonamide linkage, is made from precursor 210 by coupling it with 4-(chlorosulfonyl)benzoic acid 500 in water under buffered conditions (Scheme 5). Additional representative embodiments are illustrated in Scheme 6.

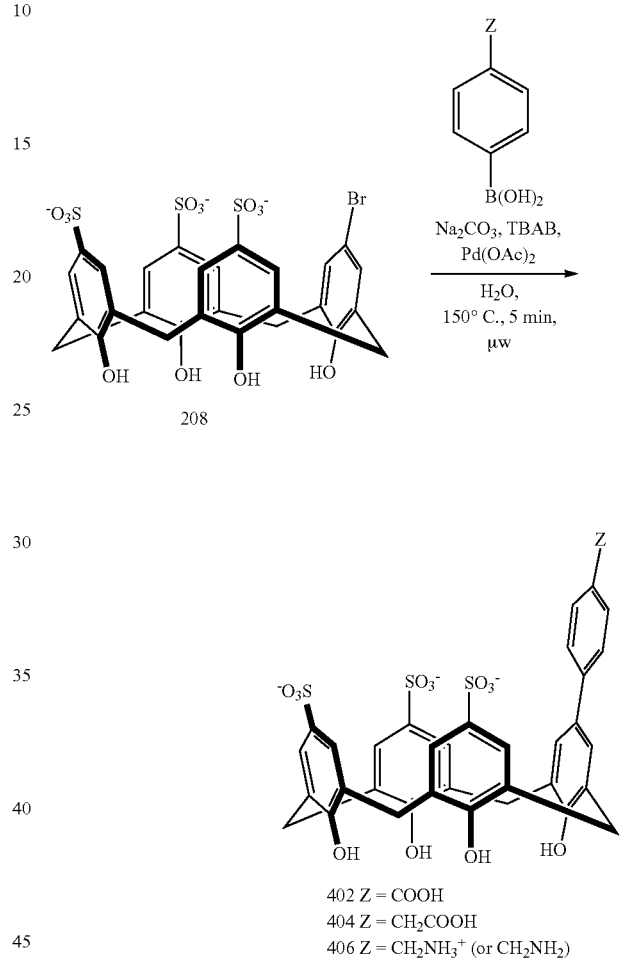

Scheme 4

402 Z = COOH
404 Z = CH$_2$COOH
406 Z = CH$_2$NH$_3^+$ (or CH$_2$NH$_2$)

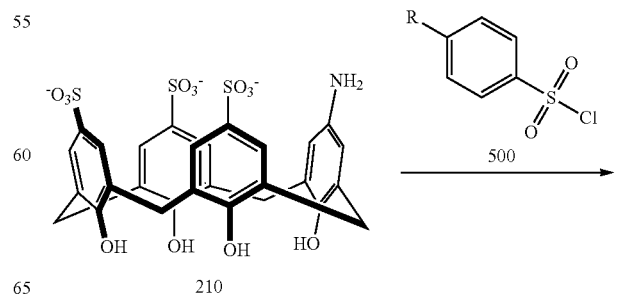

Scheme 5

-continued
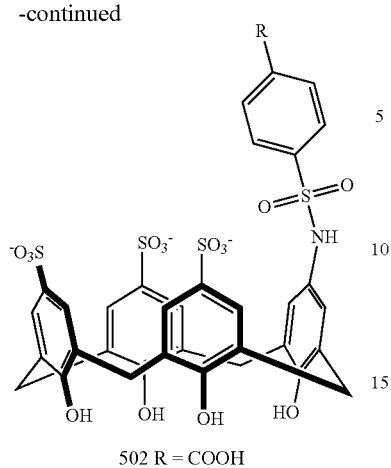
502 R = COOH
Scheme 6
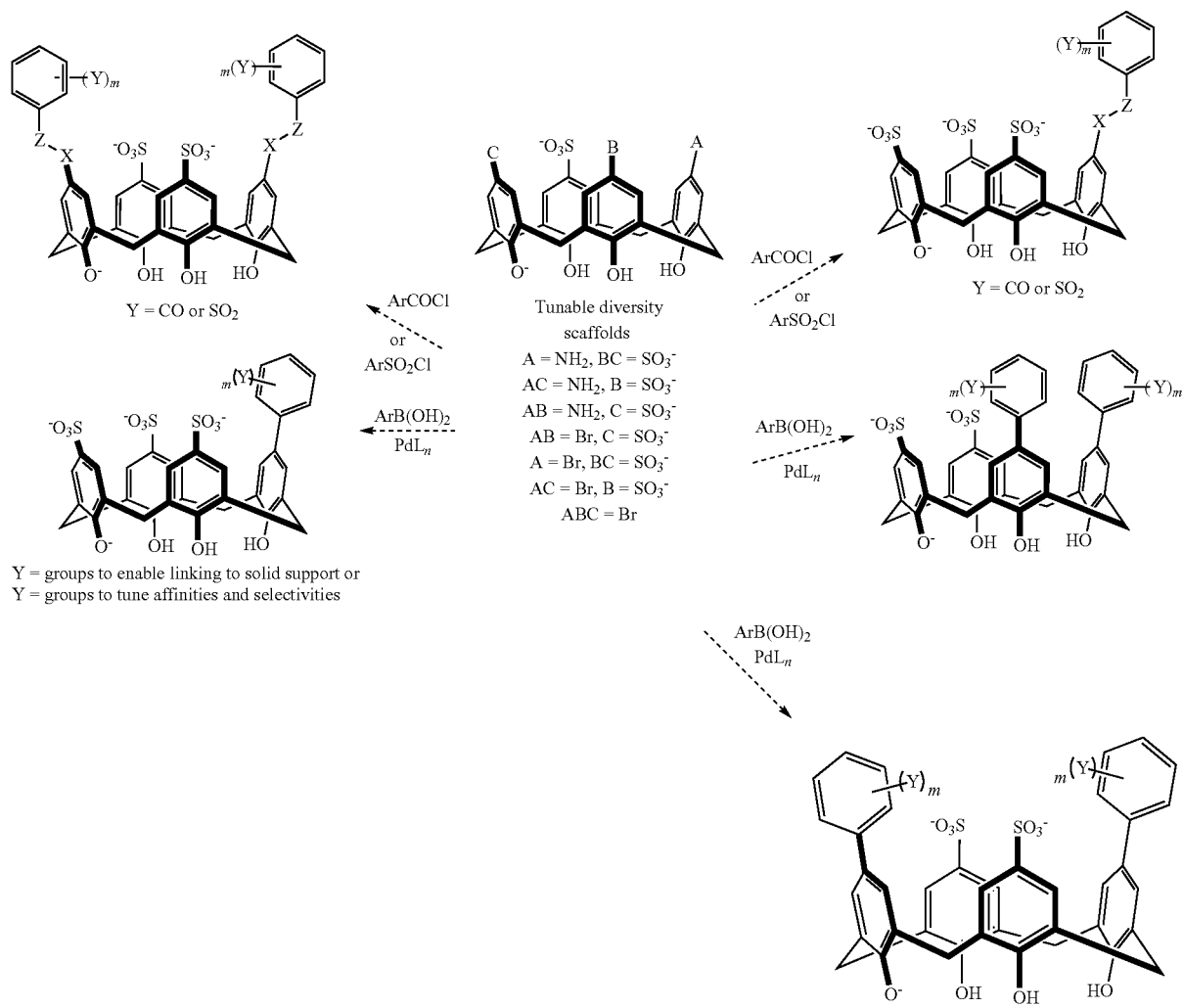

In some embodiments, the compounds disclosed herein can be coupled to a support component. Suitable support components include the supports described above. The support component can be coupled to the compounds disclosed herein by coupling a support material directly to a functional group of the compound or indirectly through a linker moiety. Scheme 7 illustrates a method embodiment whereby functionalized compound 300 is coupled to a support component ("SC") using suitable coupling reagents and a support component to form conjugate 700. With reference to Scheme 7, the support component can be coupled to any one or more of A, E, G or J directly or through a linker group (this variable bonding being depicted by connecting the support component to the bracketed structure of Scheme 7). In additional embodiments, the support component can be coupled to any one or more of Q, N, L, or M directly or through a linker group.

Representative synthetic methods for applying a support component, such as a resin or other support component is illustrated in Schemes 8 and 9.

Scheme 8

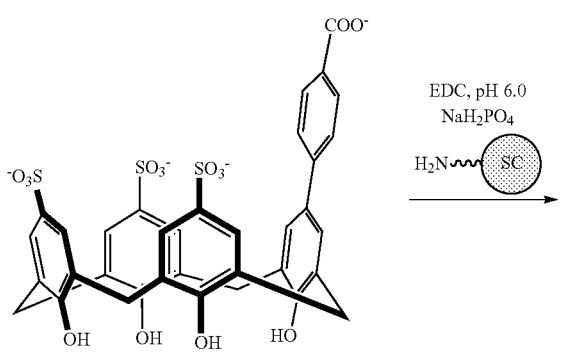

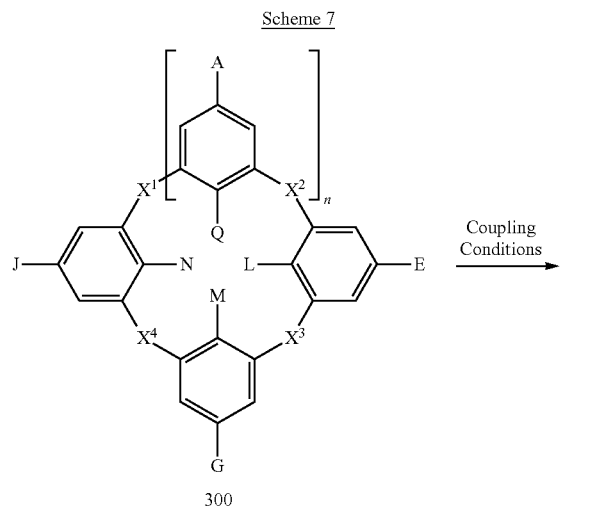

(SC = support component)

Scheme 9

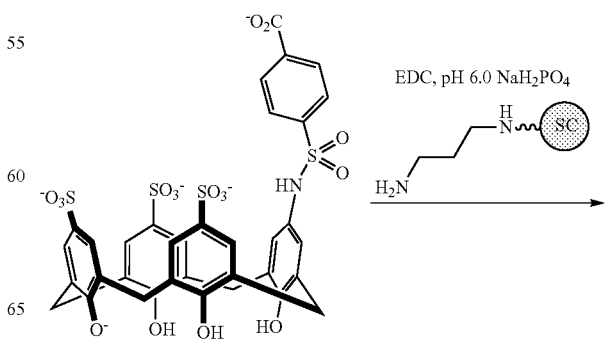

-continued

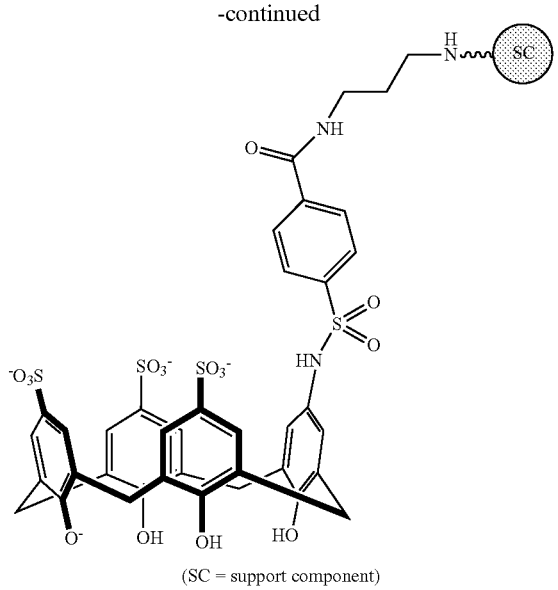

(SC = support component)

V. Methods of Using Compounds

In particular embodiments, the disclosed compounds and conjugates can be used as affinity reagents (see Scheme 10 for an example). As illustrated by the example in Scheme 10, a post-translationally modified analyte, such as methylated analyte 1002, can be trapped by a disclosed compound 1000, and thus can be separated from other non-modified analytes.

ponents of the conjugates can then interact with one or more post-translationally modified analytes such that the post-translationally modified analyte will be trapped by the compound and separated from analytes that do not comprise a post-translational modification. Methods using such compounds and conjugates can comprise introducing a fluid sample comprising one or more analytes into a solid-phase column packed with one or more conjugates comprising a support component and a compound as described herein that is coupled to the support component. The method can further comprise applying a first buffer of a first concentration to the solid-phase column and applying a second buffer of a second concentration to elute one or more post-translationally modified analytes present in the sample. The compounds of the conjugates will interact with the post-translationally modified analytes so as to sequester them from other analytes in the sample. The buffers of differing concentrations can be used to separately elute analytes that do not interact with the compounds and analytes that do interact with the compounds due to the post-translational modifications that are present on the analyte. In some embodiments, the buffer can be a salt buffer selected from a chloride salt buffer, a sulfate salt buffer, a citrate salt buffer, or the like. In some embodiments, the methods can further comprise adjusting flow rates and concentrations of the first and second buffer through the column so as to control elution times of the analytes present in the sample. The analytes will then elute at different times depending on whether they are associated with the compound of the conjugate.

In particular disclosed embodiments, column retention times, resolution, and selectivity can be controlled by any one or more of (1) the structure of the compound used in the Scheme 10

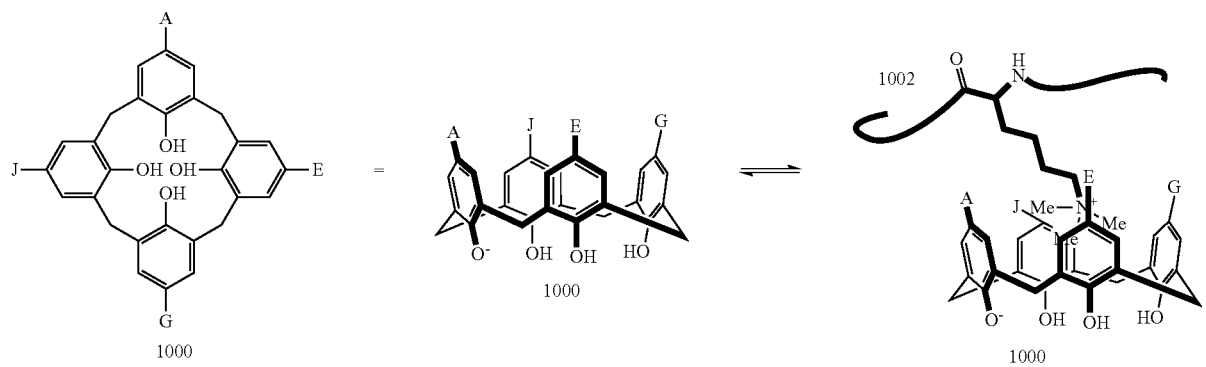

In particular disclosed embodiments, the conjugates comprise support components that facilitate using the conjugates as stationary-phase chromatography reagents in column chromatography devices and methods. In some embodiments, the compounds/conjugates can be used for liquid column chromatography, gravity chromatography, low-pressure chromatography, FPLC (fast protein liquid chromatography), HPLC (high-performance liquid chromatography), or capillary chromatography. In additional embodiments, the conjugates can be used as stationary-phase chromatography reagents for preparative chromatography or analytical chromatography. In particular disclosed embodiments, the conjugates can be physically packed into a column used in such methods and a solution comprising analytes of interest can be passed through the packed column. The compound comconjugate (e.g., the size of the macrocyclic skeleton can be increased or decreased, or functional groups present on the macrocyclic skeleton can be modified such that they become charged or neutral); (2) the dimensions of the column; or (3) the identity and concentrations of salts used in running buffer and elution buffer. Solely by way of example, in one embodiment, a proteolyzed protein mixture can be subjected to separation on a column that is packed with a compound and/or conjugate described herein and thus improve the ability of the column's ability to improve analysis of post-translationally modified proteins.

In some embodiments, the disclosed compounds and/or conjugates are used in methyl-targeting affinity columns, and can provide information about molecular mechanisms operating when eluting peptides as pure or mixed samples.

The compounds and/or conjugates also can be used to identify new methylated analytes in the proteome. The use of the compounds and/or conjugates in affinity columns is compatible with existing proteomics workflows, and offer a new tool that is different from the antibody-based enrichment tools that dominate modern epigenetics research. The applications of the disclosed methyl-targeting affinity compounds and/or conjugates described herein include prospecting, enrichment of a certain target or set of targets to facilitate their quantification, as a pre-enrichment step prior to diagnostic analysis, and other basic tasks in epigenetics research. Columns that can be used in combination with the disclosed compounds and/or conjugates include, but are not limited to, capillary columns, packed columns, or the like. The compounds and/or conjugates can be placed in the columns using dry-packing techniques, slurry techniques, or other suitable column-packing techniques known in the art.

In some embodiments, the compounds and/or conjugates are useful for discriminating between PTMs of lysine and arginine. The compounds and/or conjugates address deficiencies associated with conventional techniques. For example, antibodies targeting one methylation state will sometimes cross-react with another state, producing false positives in ChIP-Seq experiments. The disclosed compounds and conjugates avoid this problem. Also, mass spectrometry based discrimination of KMe3 vs KAc can be difficult as these components have similar masses. Lysine trimethylation adds an additional 42.049 Da while acetylation adds 42.010 Da. To distinguish between trimethylated and acetylated peptides, fragmentation patterns, RP-HPLC retention time and high-resolution MS analysis typically are used. To exacerbate the problem, a given lysine residue on the histone N-terminal tail can often be differentially decorated with two or more different PTMs. These PTMs often have high biological importance, making discrimination of KAc from KMe3 on the same site a frequently reoccurring problem. The compounds and conjugates disclosed herein obviate these issues.

In yet additional embodiments, the compounds and/or conjugates described herein can be used in pull-down assays. For example, the compounds and/or conjugates can be used to replace antibodies for immunoprecipitation techniques such as protein immunoprecipitation (IP), protein complex immunoprecipitation (Co-IP), chromatin immunoprecipitation (ChIP), RNA immunoprecipitation (RIP), or combinations thereof.

The disclosed compounds and/or conjugates also can be used to enrich, identify, or quantify a variety of target compounds from mixtures of compounds. In particular disclosed embodiments, the target compounds are biological molecules. Of particular interest are target compounds that comprise at least one post-translational modification. For example, the target compound can be selected from amino acids, peptides, and proteins that bear at least one post-translational modification. Particular disclosed embodiments concern enriching, identifying, or quantifying peptide or protein analytes based on their post-translational modifications. Particular disclosed embodiments concern enriching, identifying, or quantifying histones based on their post-translational modifications. In particular disclosed embodiments, the target compound comprises at least one post-translationally modified peptide or protein. Several different types of post-translational modifications are contemplated by the present disclosure. The disclosed compounds and/or conjugates can be used to enrich, identify, or quantify PTMs including methylations, phosphorylations, acetylations, citrullinations, hydroxylations, nitrosylations, ADP-ribosylations, glycosylations, propionylations, butyrylations, crotonylations, 2-hydroxyisobutyrylations, malonylations, succinylations, formylations, ubiquitinations, neddylations, proline cis-trans isomerizations, and combinations thereof. In particular, the disclosed compounds and/or conjugates can be used to enrich, identify, or quantify methylations and acetylations, for example monomethyl lysine (Kme1), dimethyl lysine (Kme2), trimethyl lysine (Kme3), acetyl lysine (Kac), monomethyl arginine (MMA), symmetric dimethyl arginine (sDMA), asymmetric dimethyl arginine (aDMA). This list is merely meant to be exemplary and is not limited to those particular PTMs that are listed.

In some embodiments, the quantification of analytes can be achieved by measuring the peak area in the chromatogram, with internal or external standards (including stable-isotope standards for use in mass spectrometry), or by collecting the enriched fraction off of the column any applying other quantitative analytical method. In one example, a standard sample of a Kme3-containing peptide analyte is prepared with incorporation of $^{13}C$-methyl groups, so that it has identical chromatographic properties to those of the natural analyte but a predictable mass difference. The stable isotope standard is added to the sample in a known amount, and the resulting chromatography experiment is analyzed by mass spectrometry. The relative mass spectrum peak sizes of stable isotope standard and Kme3 peptide analyte are used to determine the absolute concentration of Kme3 peptide analyte.

VI. Examples

General

Proton nuclear magnetic resonance spectra ($^1H$ NMR) were recorded at 500 MHz at 23° C. unless otherwise stated. Proton chemical shifts are expressed in parts per million (ppm, δ scale) downfield from tetramethylsilane, and are referenced to residual proton in the NMR solvent (DOH δ 4.79). Data are represented as follows: chemical shift, multiplicity (s=singlet, d=doublet, t=triplet, q=quartet, sext=sextet, m=multiplet and/or multiple resonances, br=broad), coupling constant in Hertz, and integration. Carbon nuclear magnetic resonance spectra ($^{13}C$ NMR) were recorded at 125 MHz at 23° C. Carbon chemical shifts are reported in parts per million downfield from tetramethylsilane and are referenced to the deuterium lock reference. Infrared (IR) spectra were obtained using a Perkin Elmer 1000 FT-IR spectrometer. Data are represented as follows: frequency of absorption ($cm^{-1}$), intensity of absorption (s=strong, m=medium, w=weak, br=broad). High-resolution electrospray ionization mass spectrometry (HR-ESI-MS) for compound characterization was obtained from the UVic-Genome BC Proteomics Centre on a LTQ Velos Orbitrap or in-house on a Micromass Q-TOF II. Samples were prepared in 1:1 solution of $CH3OH:H_2O$. Melting points were collected on a Gallenkamp Melting Point apparatus.

Microwave Conditions

Microwave reactions were performed using a Biotage Initiator microwave with disposable 5 mL glass vials sealed with crimped PTFE tops. Reactions were microwaved for 5 minutes at 150° C.

HPLC Purification

All reactions purified by HPLC were performed on a 250 mm×22 mm preparative C18 Alltech Apollo 10 µm column on a Shimadzu HPLC with UV detection at 280 nm. A gradient running from 90% $H_2O$ (with 0.1% TFA)/10% $CH_3CN$ (with 0.1% TFA) to 90% $CH_3CN$ (with 0.1% TFA)/10% $H_2O$ (with 0.1% TFA) over 30 minutes was used.

Synthesis

Peptides were synthesized using a CEM Liberty 1 solid-phase peptide-synthesizer. After cleavage from the resin, peptides were precipitated out of the trifluoroacetic acid based cleavage cocktail with $Et_2O$ and subsequently purified by RP-HPLC. Product-containing fractions were pooled and lyophilized to dryness. Concentration of the peptide solutions was determined by $A_{280}$, relying on the fact that all peptides contained one Tyr residue with an extinction coefficient of $e_{280}=1280$ $M^{-1}$ $cm^{-1}$. Peptides used were: H3 24-30=AcHN-AARKSAPY-COOH (both unmethylated and KMe3 variants at the underlined K residue), H3 1-7=$H_2$N-ARTKQTAY-COOH (unmethylated, R2Me2-s, R2Me2-a, K4Me1, K4Me2, K4Me3, K4Ac variants at the underlined R or K residue) H3 1-12=$H_2$N-ARTKQTARKSTGY-COOH (unmethylated, K4Me3, and K9Me3 variants at the underlined K residue).

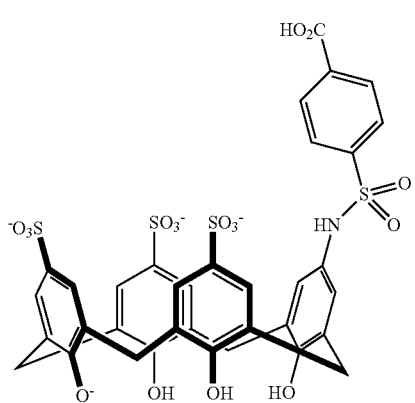

Figure 12:
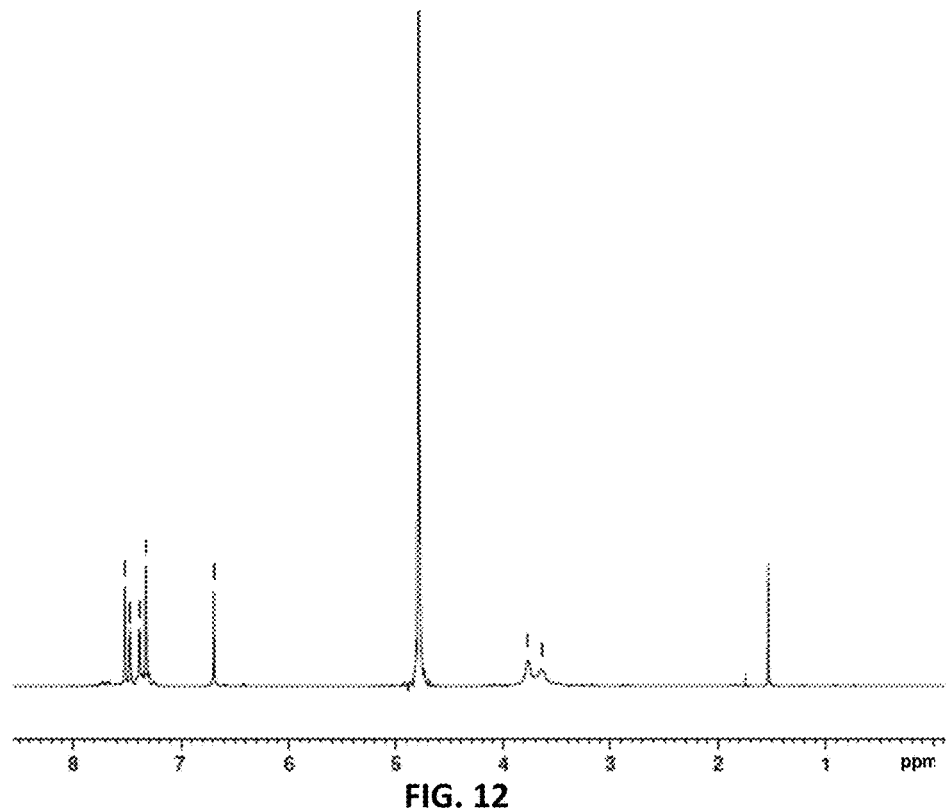
FIG. 12 is an $^1$HNMR spectrum of a representative compound.
Figure 13:
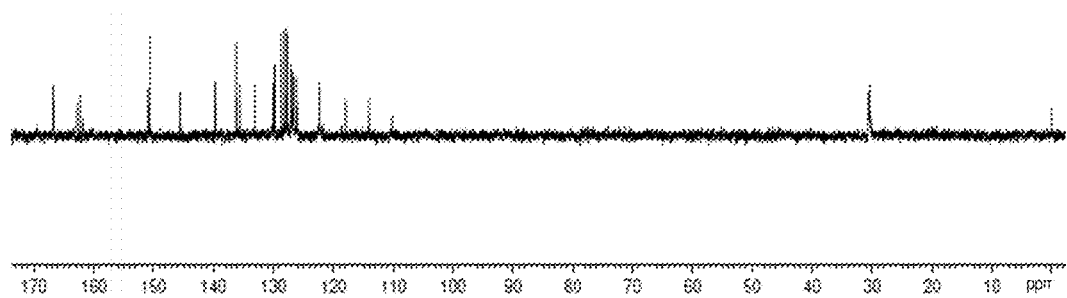
FIG. 13 is a $^{13}$CNMR spectrum of a representative compound.

5-(4-carboxyphenyl)sulfonamido-25, 26, 27, 28-tetrahydroxy-11-17-23-trisulfonatocalix[4]arene (502): Compound 210 (0.100 g, 0.147 mmol) and 4-chlorosulfonyl benzoic acid (1.1 equiv.) are dissolved in 6 mL of 1 M $Na_2HPO_4$/$NaH_2PO_4$ buffer (pH 8) and stirred overnight at room temperature. The aqueous solution is extracted with DCM (2×20 mL), EtOAc (1×25 mL), the aqueous phase is separated and evaporated. HPLC purification and evaporation of solvents in vacuo affords off-white powder in 34% yield. Mp: 204° C. (dec). IR (KBr pellet): 3210s br, 1714s, 1474s, 1454s, 1401w, 1160s, 1110s, 1040s, 886w, 786w, 690w, 651m, 623m, 559w. $^1$H NMR (300 MHz, $D_2O$): δ 7.52 (s, 2H), 7.47 (d, J=1.8 Hz, 2H), 7.38 (d, J=1.8 Hz, 2H), 7.32 (s, 4H), 6.70 (s, 2H), 3.77, 3.64 (br, 8H). 13C NMR (75 MHz, $D_2O$): δ 166.7, 150.8, 150.6, 145.5, 139.7, 136.1, 135.6, 133.1, 130.1, 129.8, 128.7, 128.2, 127.8, 127.7, 127.1, 126.8, 126.6, 126.1, 122.4, 30.5, 30.4. HR-ESI-MS: m/z observed 886.0216 ([M+Na]+, $C_{35}H_{29}NO_{17}S_4Na^+$; calculated 886.0216); see FIGS. 12 and 13.

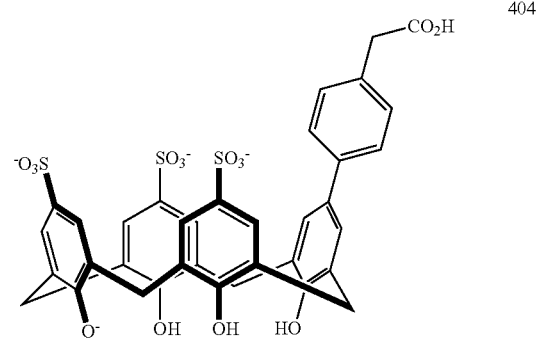

Figure 14:
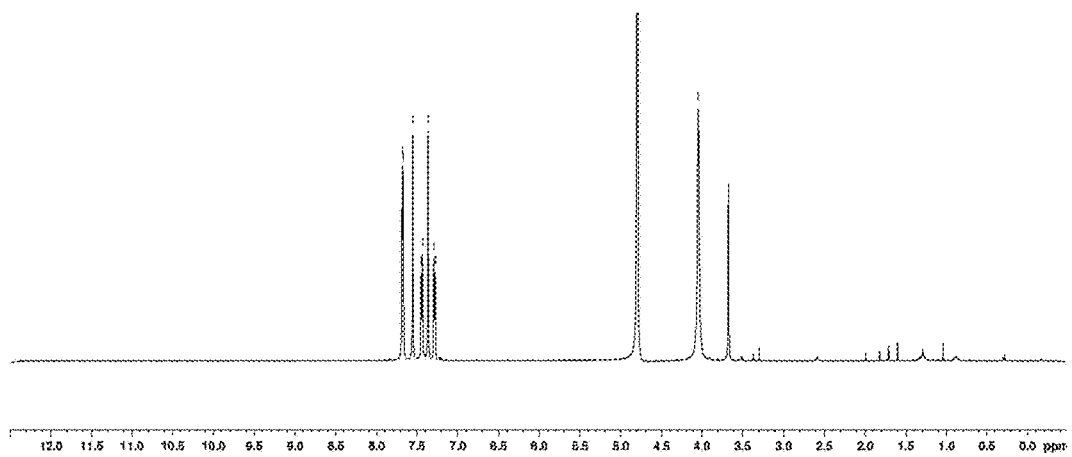
FIG. 14 is an $^1$HNMR spectrum of another representative compound
Figure 15:
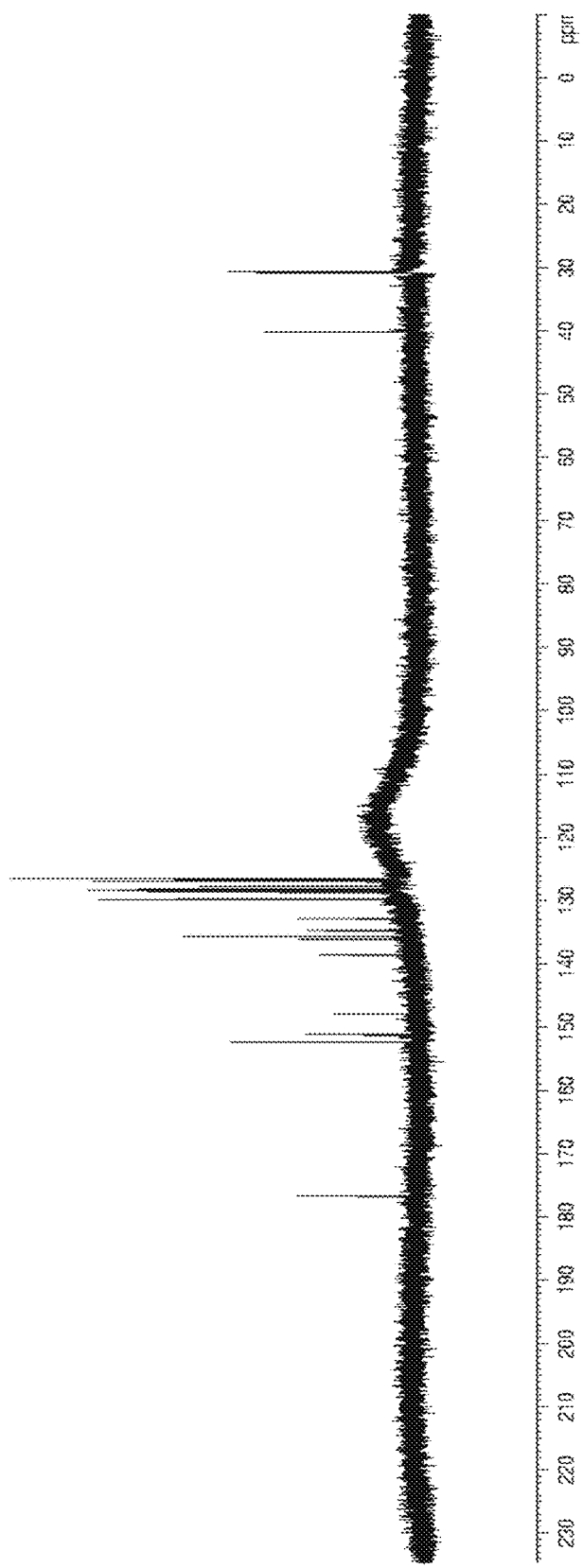
FIG. 15 is a $^{13}$CNMR spectrum of another representative compound.

5-(4-carboxymethylphenyl)-25, 26, 27, 28-tetrahydroxy-11-17-23-trisulfonatocalix[4]arene (404): Compound 208 (0.042 g, 0.057 mmol), 4-carboxymethylphenylboronic acid (1 equiv., 0.057 mmol), tetrabutylammonium bromide (0.0095 g, 0.5 equiv., 0.003 mmol), $Pd(OAc)_2$ (0.0028 g, 20 mol %) and sodium carbonate (0.0023 g, 3.8 equiv., 0.218 mmol) are dissolved in 5 mL of deionized $H_2O$ inside a microwave vial and microwave-irradiated for 5 minutes at 150° C. with stirring and cooling air on. The aqueous solution is extracted with DCM (2×20 mL), EtOAc (1×25 mL), the aqueous phase is separated and evaporated. HPLC purification and evaporation of solvents in vacuo affords an off-white powder in 50% yield. Mp: 240° C. (dec). IR (KBr pellet): 3253br, 2936s, 1719s, 1468s, 1457s, 1223w, 1153s, 1115s, 1041s, 887w, 812w, 785m, 658m, 627m, 556m. $^1$H NMR (500 MHz, $D_2O$): δ 7.68 (s, 2H), 7.67 (s, 2H), 7.55 (s, 2H), 7.43 (d, J=7.9 Hz, 2H), 7.36 (s. 2H), 7.28 (d, J=7.9 Hz 2H), 7.27 (s, 2H), 4.0 (s, 8H) $^{13}$C NMR (125 MHz, $D_2O$): δ 176.7, 152.3, 151.2, 147.9, 138.7, 136.2, 135.7, 134.8, 132.9, 129.8, 128.7, 128.3, 128.2, 127.7, 127.0, 126.7, 126.6, 40.2, 30.8, 30.7 HR-ESI-MS: m/z observed 398.03085 ([M−2H]$^{2-}$, $C_{36}H_{28}O_{15}S_3^{-2}$; calculated 383.03004). See FIGS. 14 and 15.

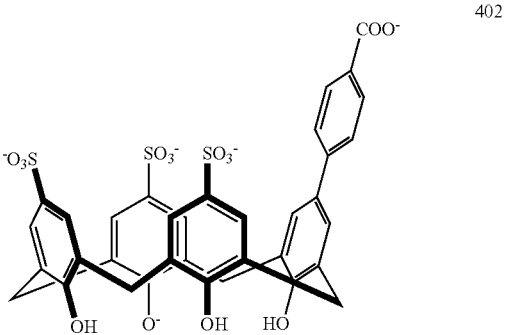

5-(4-carboxymethylphenyl)-25, 26, 27, 28-tetrahydroxy-11-17-23-trisulfonatocalix[4]arene (402): Compound 208 (0.042 g, 0.057 mmol), 4-boronobenzoic acid (1 equiv., 0.057 mmol), tetrabutylammonium bromide (0.0095 g, 0.5 equiv., 0.003 mmol), $Pd(OAc)_2$ (0.0028 g, 20 mol %) and sodium carbonate (0.0023 g, 3.8 equiv., 0.218 mmol) are dissolved in 5 mL of deionized $H_2O$ inside a microwave vial and microwave-irradiated for 5 minutes at 150° C. with stirring and cooling air on. The aqueous solution is extracted with DCM (2×20 mL), EtOAc (1×25 mL), the aqueous phase is separated and evaporated. HPLC purification and evaporation of solvents in vacuo affords an off-white powder in 38% yield. Mp: >250° C. (dec). IR (KBr pellet): 3424s br, 1701m, 1608m, 1477m, 1458m, 1453m, 1186s, 1115s, 1045s, 892w, 856w, 777w, 677w, 660m, 627m, 553m, 517w. $^1$H NMR (300 MHz, D$_2$O): δ 8.06 (d, J=8.4 Hz, 2H), 7.72 (d, J=2.1 Hz, 2H), 7.70 (d, J=2.4 Hz, 2H), 7.68 (d, J=8.4 Hz, 2H), 7.59 (s, 2H), 7.55 (s, 2H), 4.38, 4.37 (2s, 8H). $^{13}$C NMR (75 MHz, D$_2$O): δ 170.6, 152.1, 151.4, 149.0, 144.8, 136.4, 136.1, 133.9, 130.4, 128.8, 128.6, 128.6, 128.5, 128.2, 127.9, 126.8, 126.8, 126.7, 126.7, 31.2, 30.8. HR-ESI-MS: m/z observed 807.0488 ([M+Na]$^+$, C$_{35}$H$_{28}$O$_{15}$S$_3$Na$^+$; calcd 807.0488).

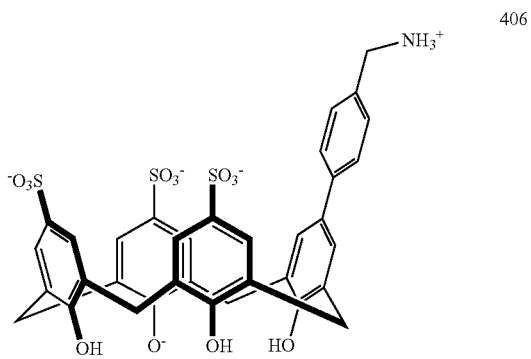

406

5-(4-aminomethylphenyl)-25, 26, 27, 28-tetrahydroxy-11-17-23-trisulfonatocalix[4]arene (406): Compound 208 (0.042 g, 0.057 mmol), 4-aminomethylbenzeneboronic acid hydrochloride (1 equiv., 0.057 mmol), tetrabutylammonium bromide (0.0095 g, 0.5 equiv., 0.003 mmol), Pd(OAc)$_2$ (0.0028 g, 20 mol %) and sodium carbonate (0.0023 g, 3.8 equiv., 0.218 mmol) are dissolved in 5 mL of deionized H$_2$O inside a microwave vial and microwave-irradiated for 5 minutes at 150° C. with stirring and cooling air on. The aqueous solution is extracted with DCM (2×20 mL), EtOAc (1×25 mL), the aqueous phase is separated and evaporated. HPLC purification and evaporation of solvents in vacuo affords an off-white powder in 32% yield. MP>250° C. (dec). IR (KBr pellet): 3236br, 2950br, 1474m, 1211m, 1161m, 1113m, 1040s, 657w, 628w, 553w. $^1$H NMR (300 MHz, D$_2$O): δ 7.86 (d, J=2.0 Hz, 2H), 7.78 (d, J=2.0 Hz, 2H), 7.56 (s, 2H), 7.11 (s, 2H), 6.65 (d, J=8.9 Hz, 2H), 6.03 (d, J=7.4 Hz, 2H), 4.12 (br, 8H), 2.58 (s, 2H) $^{13}$C NMR (75 MHz, D$_2$O): δ 152.5, 150.9, 147.5, 138.9, 136.4, 135.9, 133.4, 130.0, 128.8, 128.7, 128.4, 128.0, 127.9, 127.4, 126.5 (×2), 126.4 (×2), 41.9, 30.9, 30.6. HR-ESI-MS: 770.1034 m/z observed: ([M+H]$^+$, C$_{35}$H$_{32}$NO$_{13}$S$_3^+$; calcd 770.1036).

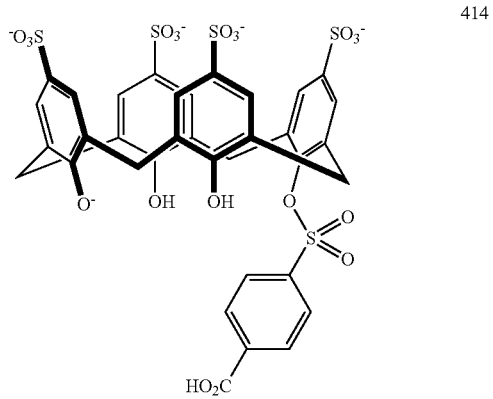

414

Figure 16:
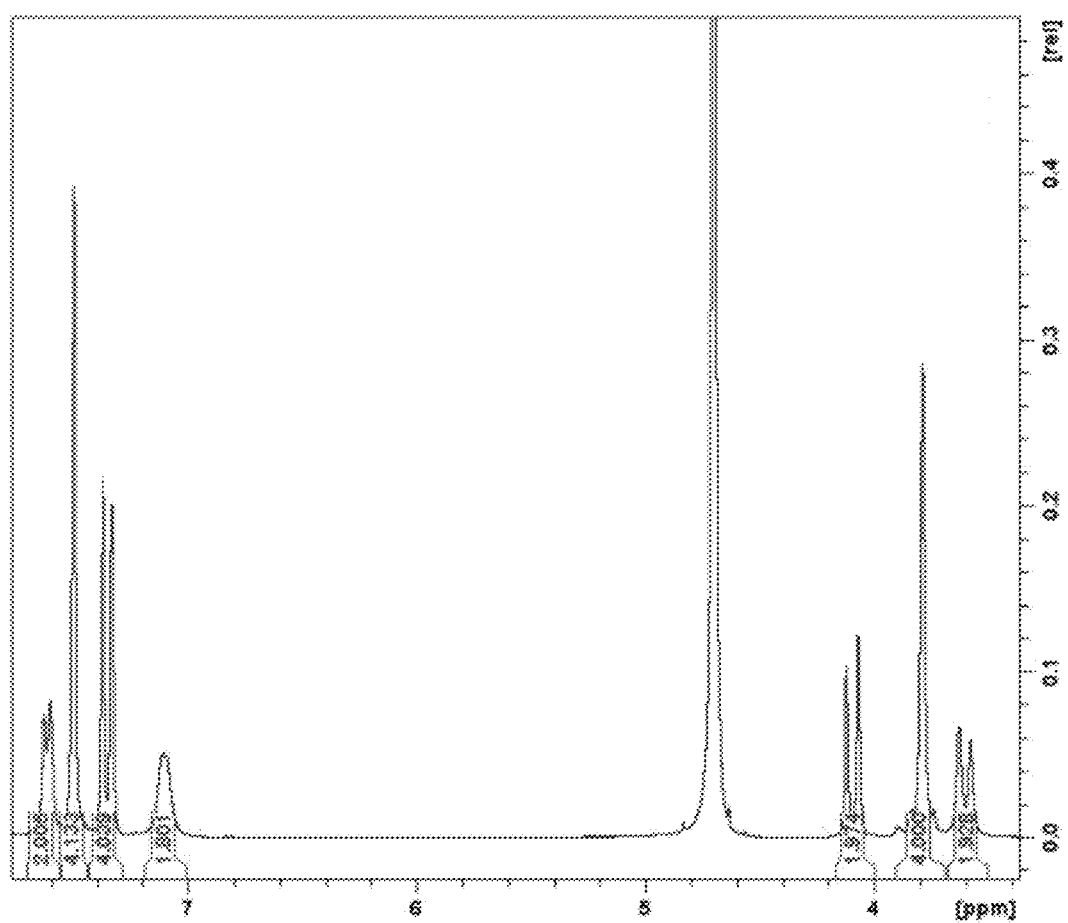
FIG. 16 is a proton NMR spectrum of a representative compound described herein.

Compound 414: para-Sulfonatocalix[4]arene is mixed with 4-chlorosulfonylbenzoic acid at a 1:1 ratio in a minimal volume of 100 mM pH 9 Na$_2$HPO$_4$ buffer. The reaction is maintained at pH 9 by adjusting with 1 M NaOH and 1 M HCl as necessary. After stirring at room temperature overnight, purification was completed by HPLC using an Apollo C18, 5 μm in preparative scale column. Solvent A: Deionized water with 0.1% TFA. Solvent B: MeCN with 0.1% TFA. Gradient program: 0-5 min 90% A, 5-25 min gradient to 10% A, 25-28 min 10% A, 28-30 min gradient to 90% A. Unreacted starting material t$_R$=14.8 min, compound 414 t$_R$=15.5 min, disubstituted product t$_R$=17 min. Compound 414: $^1$H NMR (300 MHz, D$_2$O): δ 7.62 (d, J=7.8 Hz, 2H), 7.50 (s, 4H), 7.35 (d, J=12.4 Hz, 4H), 7.11 (s, 2H), 4.09 (d, J=15.2 Hz, 2H), 3.79 (s, 4H), 3.60 (d, J=15.2 Hz, 2H). ESI-MS: m/z [M–H]$^-$ calculated for C$_{35}$H$_{27}$O$_{20}$S$_5^-$ 926.97, observed 927.20; [M–2H+Na]$^-$ calculated for C$_{35}$H$_{26}$O$_{20}$S$_5$Na$^-$ 948.95, observed 949.07. See FIG. 16.

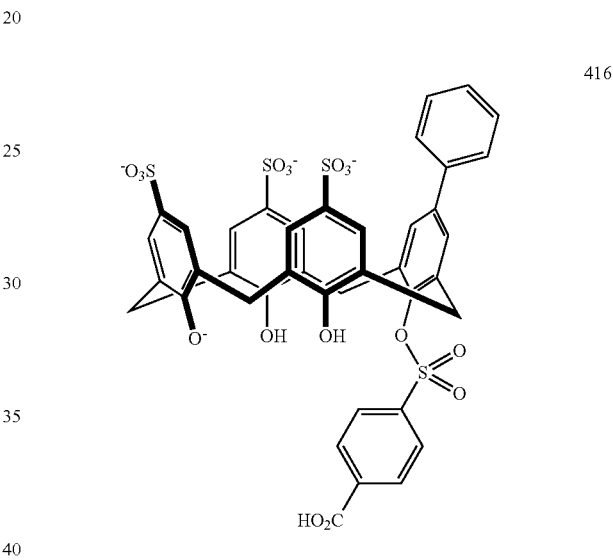

416

A microwave vial is charged with 1 equivalent mono bromo-trisulfonatocalix[4]arene (208), 4 equivalents of phenylboronic acid, 4 equivalents sodium carbonate, 1 equivalent tetra-n-butylammonium bromide, 10 mol % of palladium(II) acetate and a stir bar. All the solids are dissolved in water and the vial is sealed. The vial is then microwaved at 150° C. for 5 min in a reactor. After cooling the vial to room temperature, 1 mL of 1 M thiourea is added. The vial is then heated at 70° C. for 1 hour. The mixture is then passed through celite, concentrated to dryness, and redissolved in 9:1 water:acetonitrile for HPLC purification of the Phenyl-coupled intermediate. After purification the intermediate is mixed with 4-chlorosulfonylbenzoic acid at a 1:1 ratio in a minimal volume of 100 mM pH 9 Na$_2$HPO$_4$ buffer. The reaction is maintained at pH 9 by adjusting with 1 M NaOH and 1 M HCl as necessary. After stirring at room temperature overnight, purification was completed by HPLC using an Apollo C18, 5 μm preparative scale column. Solvent A: Deionized water with 0.1% TFA. Solvent B: MeCN with 0.1% TFA. Gradient program: 0-20 min gradient from 90% A to 60% A, 20-22 min 60% A to 10% A, 22-26 min 10% A, 26-27 min gradient to 90% A. Compound 416 t$_R$=16 min, unreacted starting material t$_R$=16.7 min, disubstituted product t$_R$=18.6 min. ESI-MS: m/z [M–H]$^-$ calculated for C$_{41}$H$_{31}$O$_{17}$S$_4^-$ 923.04, observed 923.0.

Calixarene Immobilization

In some examples, agarose resins can be used. Agarose resins typically comprise 2-6% agarose by weight that has been cross-linked and milled into beads. Agarose itself is a linear polysaccharide derived from seaweed, formed from the repeat unit disaccharide of agarobiose, and can gel at low temperatures and form porous networks inside the beads. These porous channels are large enough to allow biomolecules such as proteins and DNA to pass, making agarose a useful medium for the chromatographic separation of biomolecules based on size. In its unmodified state, it is used in chromatographic applications such as gel electrophoresis and size exclusion chromatography. It can also be chemically derivatized with preactivated functional heads for the attachment of different molecules for the purposes of affinity chromatography. AffiGel-102 agarose resin was purchased from BioRad. AffiGel consists of a slurry of crosslinked agarose beads with an undisclosed % agarose. They are between 70-300 μM in diameter and are preactivated with functional group heads attached through a short proprietary hydrophilic linker. AffiGel-102 comes packaged as a slurry and has a 14 μmole/mL concentration of primary amine functional heads for the coupling to a molecule bearing a carboxylic acid through a carbodiimide driven amide bond formation. AffiGel-10 similarly comes in a slurry with 15 μmole/mL concentration, but has activated N-hydroxysuccinimide (NHS) ester groups for coupling to molecules bearing free amines. The Profinity epoxide resin is another suitable resin that can be used. It is functionalized with electrophilic epoxide head groups for reaction with molecules bearing nucleophiles such as amines. Also, in some examples, TentaGel (TG) can be used. TentaGel is a water swellable resin comprising a graft copolymer composed of polyethylene glycol linker arms affixed to a cross-linked polystyrene core matrix and machined into beads 130 μm in diameter. Preactivated functionality options for these resins are similar as to the agarose based resins.

Carboxylic acid-containing calixarenes 404, 502, 414, and 416 were coupled to Affigel-102 using EDC by the instructions provided. To monitor the progress of the coupling, the supernatant of the coupling reaction was sampled by LCMS using a Phenomenex Luna C18 analytical column and the mobile phase gradient outlined above, at a flow rate of 1.5 mL/min. Relative calixarene concentration in the supernatant was determined by area under the curve (AUC) calculations of the UV absorbance monitored at $A_{280}$. After coupling, the resin was filtered over a glass-fritted funnel and rinsed with 2 M $NH_4Cl$ and $diH_2O$ before being stored in a 1.5 mL microfuge tube suspended in $diH_2O$.

In particular disclosed embodiments, amine functionalized resins Affigel-102 and TentaGel S $NH_2$ were coupled to carboxylic acid-containing calixarenes 402 and 404 by the following general procedure: Resin slurry (0.6 mL) was placed in a microfuge tube, and to it was added 1.1 equivalents of calixarene dissolved in 0.6 mL of 50 mM phosphate buffered $dH_2O$ at pH 7.0 with caffeine (1.0 mM) as an internal standard. (Transfer of resin from the bottle was achieved using a 1 mL pipette with a tip that had been snipped off to enlarge the opening). To initiate amide bond formation, 2 equivalents of the carbodiimide coupling agent EDC were added as the HCl salt and the tubes were rotated end-over-end at room temperature. To monitor the progress of the coupling, the tubes were centrifuged for ~3 seconds to settle the resin, samples of supernatant (10 μL) were taken using an autopipette, diluted to 120 μL total volume with $diH_2O$+ 0.1% TFA with tosylate (0.10 μM) as an external standard. Sample volumes of 40 μL were injected onto an analytical Phenomenex Luna C18 column using the gradient outlined in Section 2.6.3, at a flow rate of 1.5 mL/min. Relative calixarene concentration in the supernatant was determined by area under the curve (AUC) of UV absorbance monitored at $A_{280}$. After coupling, the resin was filtered over a glass-fritted funnel and rinsed with $diH_2O$ before being stored in a 1.5 mL microfuge tube suspended in $diH_2O$. As a final confirmation that the resin had been covalently functionalized, the total filtrate was collected and analyzed for calixarene content by LCMS while accounting for dilution.

This protocol was adapted for the coupling of the amine functionalized calixarene 406 to the epoxide and NHS-activated resins. In this protocol, calixarene levels were calculated before and after resin addition relative to the caffeine internal standard. A decrease in calixarene concentration compared to a caffeine standard was considered evidence of covalent coupling to the resin.

1.1.1 Batch Pulldown Protocol

Calixarene-functionalized resins were treated with different mixtures of peptides under different conditions as described in the Results section. Standard conditions are described as follows. Example were set up in 1.5 mL microfuge tubes. Typical conditions: 700 μM (4 eq.) of resin, 0.18 μM (1 eq.) of each of the AARKSAPY K and KMe3 variant peptides, along with buffer and co-solvents made up to 200 μL of total volume with $diH_2O$. Standard buffer conditions consisted of 5 mM phosphate buffer for pH 4-12 and acetate buffer for pH<4. Resin was added last by pipette in 25 μL volume. Examples were sampled before resin addition and again after 18 h incubation. During this period experiments were refrigerated at 4° C. To sample the supernatant, the tubes were briefly centrifuged to settle the resin and 10 μL removed by autopipette. This 10 μL was diluted into 120 μL total volume with 0.1% TFA in $H_2O$ with tosylate (0.10 μM) as an external standard prior to LC injection. Sample volumes of 40 μL were injected onto an analytical Phenomenex Luna C18 column by an isocratic elution using 90% $H_2O$/10% MeCN containing 0.1% TFA at 1.5 mL/min over 20 minutes. AUC measurements of the UV absorbance at $A_{222}$ were used to determine the levels of peptides in the supernatant. To keep peak shape consistent and AUC measurements accurate, the column was refreshed every 20 samples or fewer by running 100% MeCN with 0.1% TFA for 1 h at 1.5 mL/min. Blank samples containing the original peptide mixture were injected 3 times per batch of LCMS runs to ensure that LCMS response was consistent over the course of the entire sample list.

Preparation of Columns and Capillaries

The 1 mL HiTrap SPXL ion exchange column was purchased from GE Healthcare. Empty 1 mL columns for loading with prototype resins were purchased from Agarose Bead Technologies; these columns have a length of 35 mm and an internal diameter of 6.2 mm. Columns were loaded with resin following the instructions provided. Capillary columns were prepared from 1/16" OD, 0.040" ID PFA tubing purchased from IDEX. Tubing was cut to the desired length and packed with resin using a syringe pump, the ends of the capillary were sealed with 10 μm pore diameter frits enclosed into a union assembly. A conjugate comprising compound 502 was packed into either 1 mL glass columns (6.2×35 mm) or Teflon capillaries (1×600 mm). Thorough washing of the resin with 50-100 column volumes of elution buffer was performed to ensure removal of EDC and byproducts from the resin prior to sample injection.

In some examples, the columns were clamped in a vertical position and loaded with 1.4 mL agarose resin slurry, which equates to 19.6 mmole of calixarene. Care was taken to avoid the introduction of air bubbles during loading. To seal the column after loading the resin, fritted end-plugs which were inserted into both ends, compacting the resin to 1 mL total volume. These end plugs have 10-32 fittings for connection to PEEK tubing commonly used in FPLC. Columns were briefly subjected to a flow rate of 5 mL/min of $diH_2O$ using the FPLC to help settle the beads and remove any air bubbles inside the column. The conjugates were then packed into columns.

Instrument

In some examples, columns were plumbed into an Agilent 1200 Series HPLC system. Sampling was performed using the onboard sampling and injection unit. Detection was achieved using the UV detector observing at $A_{222}$ and $A_{280}$.

In some other examples, columns were plumbed into an Agilent 1200 Series HPLC system that had been set up for FPLC style low-pressure, aqueous phase purification of biomolecules. Fractions were collected into 4 mL vials using the onboard fraction collector.

Chromatography

Step-gradient elution protocols were employed to achieve the desired separations. A switch from low to high-ionic strength buffer was effective in eluting bound molecules from strong cation exchange columns, such as the HiTrap SPXL, whereas elution from the calixarene-based columns was most effectively achieved with elution buffers containing $NH_4^+$ salts. A general run program consists of an initial 5-10 column volumes (CV) of low ionic strength buffer ('running buffer'), such as 50 mM aqueous phosphate buffer, pH 7.5. A change to an elution solution that was made up of running buffer plus added salts such as 2 M $NH_4Cl$ ('elution buffer') was applied over 5 CV and held for 5 CV to ensure the elution of all bound species. The gradient is then reversed back to the running buffer to equilibrate the column prior to the next sample. Flow rates of 1 mL/min were employed for column separations and a flow rate of 0.1 mL/min was employed when running capillary columns. All peptides were created to 1.0 mM stock solutions, as determined by $A_{280}$, and typically injected in 20 µL aliquots.

A method time-program was created and used consistently during all analyses and optimizations. The representative program below is for the 1 mL column.

0-10 minutes: pure running buffer (RB)
10-15 minutes: transition from RB to elution buffer (EB)
15-20 minutes: full EB
20-25 minutes: transition back to RB
25-30 minutes: full RB to condition the column for the next sample.

To fully equilibrate the column to the current running conditions, 3 or more blank runs were performed before starting a batch of samples and 1 blank run was performed prior to new experimental runs each time the solvent/salt system was changed. The baseline shows consistent, minor variations arising from changes in salt concentrations. Chromatograms were obtained at $A_{222}$ and were baseline subtracted from a blank injection running the same method.

Protein Digest—Preparation

Samples of calf thymus histone (Worthington Chemicals) were used as obtained. Histones were incubated at 100:1 (w/w) with ArgC protease (Sigma Aldrich) at 37° C. for 18 h in 100 mM $NH_4HCO_3$. After incubation, digested samples were frozen at −4° C. and thawed immediately before use.

Fractions as eluted from a column comprising a conjugate formed with compound 502 (referred to herein as 502-SC) were collected in 1 mL aliquots in Eppendorf tubes and pooled into two samples: flow-through fraction (S2), and retained fraction (S3). Along with the input sample (S1), these fractions were submitted for proteomics analysis.

Protein Digest—LC-MS/MS Analysis

Samples were acidified with formic acid (10 µL) prior to C18Stage desalting and sample cleanup. Thermo Scientific C18Stage Tips SP301 (200 µL) were used to desalt peptides. Following binding and washing, peptides were eluted with 40 µL (80% v/v Acetonitrile, 0.1% v/v Formic acid), speed vacuumed to near dryness and rehydrated with 2% Acetonitrile, 0.1% Formic acid, and water.

The peptide mixtures were separated by on-line reverse phase chromatography using a Thermo Scientific EASY-nLC 1000 system with a reversed-phase pre-column Magic C18-AQ (100 µm I.D., 2 cm length, 5 µm, 100 Å, and an in-house prepared reverse phase nano-analytical column Magic C-18AQ (75 µm I.D., 15 cm length, 5 µm, 100 Å, Michrom BioResources Inc, Auburn, Calif.), at a flow rate of 300 nL/min. The chromatography system was coupled on-line with an Orbitrap Fusion Tribrid mass spectrometer (Thermo Fisher Scientific, San Jose, Calif.) equipped with a Nanospray Flex NG source (Thermo Fisher Scientific). Solvents were A: 2% Acetonitrile, 0.1% Formic acid; B: 90% Acetonitrile, 0.1% Formic acid. After a 249 bar (~8 µL) pre-column equilibration and 249 bar (~10 µL) nanocolumn equilibration, samples were separated by a 55 minute gradient (0 min: 5% B; 45 min: 30% B; 2 min: 100% B; hold 8 min: 100% B).

The Orbitrap Fusion instrument parameters were as follows for iontrap (IT-MS/MS) with HCD fragmentation: Nano-electrospray ion source with spray voltage 2.4 kV, capillary temperature 275°. Survey MSI scan m/z range 400-2000 profile mode, resolution 120,000 FWHM@200 m/z one microscan with maximum inject time 50 ms. The Siloxane mass 445.120024 was used as lock mass for internal calibration. Data-dependent acquisition Orbitrap survey spectra were scheduled at least every 3 seconds, with the software determining "Top-speed" number of MS/MS acquisitions during this period. The automatic gain control (AGC) target values for FTMS and MSn were 200,000 and 10,000 respectively. The most intense ions charge state 2-7 exceeding 50,000 counts were selected for CID ion trap MSMS fragmentation with detection in centroid mode. Monoisotopic Precursor Selection (MIPS) was enabled and Dynamic exclusion settings were: repeat count: 2; repeat duration: 15 seconds; exclusion duration: 60 seconds with a 10 ppm mass window. The ddMS2 IT CID scan used a quadrupole isolation window of 1.6 Da; IonTrap rapid scan rate centroid detection first mass 100 m/z, 1 microscan, 50 ms maximum injection time and stepped collision energy 30%±5.

The samples were also analyzed by orbitrap (OT-MS/MS) with HCD fragmentation. The survey MS 1 scan m/z range 400-2000 profile mode, resolution 120,000 FWHM@200 m/z one microscan with maximum inject time 50 ms. The Siloxane mass 445.120024 was used as lock mass for internal calibration. Data-dependent acquisition Orbitrap survey spectra were scheduled at least every 3 seconds, with the software determining "Top-speed" number of MS/MS acquisitions during this period. The automatic gain control (AGC) target values for FTMS and MSn were 400.000 and 10,000 respectively. The most intense ions charge state 2-7 exceeding 50,000 counts were selected for HCD MSMS fragmentation in the ion routing multipole. Monoisotopic Precursor Selection (MIPS) was enabled and Dynamic exclusion settings were: repeat count: 2; repeat duration: 10 seconds; exclusion duration: 10 seconds with a 10 ppm mass window. The ddMS2 OT HCD scan used a quadrupole isolation window of 1.6 Da; 30,000 resolution Orbitrap scan first mass 100m/z with centroid detection, 1 microscan, 60 ms maximum injection time and stepped collision energy 30%±5.

Protein Digest—Data Analysis

Raw files were created by XCalibur 3.0.63 (Thermo Scientific) software and analysed with Proteome Discoverer 1.4.0.228 software suite (Thermo Scientific). Parameters for the Spectrum Selection to generate peak lists of the CID spectra (activation type: CID; s/n cut-off: 1.5; total intensity threshold: 0; minimum peak count: 1; precursor mass: 350-5000 Da) The peak lists were submitted to an in-house Mascot 2.4.1 server against UP_cow (24,461 sequences; 13,017,573 residues) database search as follows: precursor tolerance 5 ppm; MS/MS tolerance 0.8 Da; Trypsin (or Arg-C) enzyme 2 missed cleavages; FT-ICR instrument type; fixed modification: none; variable modifications: acetyl(K), methyl (K,R), dimethyl(K,R), trimethyl (K); and propionyl (K). Percolator settings: Max delta Cn 0.05; Target FDR strict 0.01, Target FDR relaxed 0.05 with validation based on q-Value.

The data collected by FT-HCD MS/MS used the following search parameters: precursor tolerance 5 ppm and MS/MS tolerance 15 mmu.

The raw data was further processed and analyzed for PTM content using Scaffold. The software presented the probability that an observed peptide was from a specific protein. Proteins with less than 50% probability of being present based on these observed peptides were omitted from the PTM data analysis. The percent coverage refers to the percent of the known sequence of the protein that was actually observed using the mass spectrometry proteomics analysis. For each peptide, any residues with a PTM were also noted as in Table 6.

TABLE 6

List of proteins and PTMs identified in each fraction.

| Fraction | Accession | Probability | Coverage | PTM residue | Kme1 | Kme2 | Kme3 | Kac | Rme1 | Rme2 |
|---|---|---|---|---|---|---|---|---|---|---|
| S1 | G3MWV5 | 100% | 32% | K34 | 1 | | | | | |
| S1 | G3MWV5 | 100% | 32% | K46 | | | | 1 | | |
| S1 | G3MWV5 | 100% | 32% | K52 | | | | 1 | | |
| S1 | H12 | 100% | 22% | R33 | | | | | 1 | |
| S1 | H12 | 100% | 22% | K34 | 1 | | | | | |
| S1 | H12 | 100% | 22% | K46 | | | | 1 | | |
| S1 | H12 | 100% | 22% | K52 | | | | 1 | | |
| S1 | G5E6I9 | 100% | 16% | none | | | | | | |
| S1 | F2Z4F9 | 100% | 69% | none | | | | | | |
| S1 | E1B8G9 | 100% | 9% | none | | | | | | |
| S1 | G3MWH4 | 99% | 13% | none | | | | | | |
| S1 | F1MVX6 | 94% | 19% | K140 | | | | 1 | | |
| S1 | G3N0O80 | 89% | 0% | none | | | | | | |
| S1 | H31 | 100% | 51% | K19 | | | | 1 | | |
| S1 | H31 | 100% | 51% | K24 | | | | 1 | | |
| S1 | H31 | 100% | 51% | K28 | 1 | 1 | | | | |
| S1 | H31 | 100% | 51% | K80 | 1 | 1 | | | | |
| S1 | H3C | 60% | 17% | K80 | 1 | 1 | | | | |
| S1 | G3X807 | 100% | 78% | R15 | | | | | 1 | |
| S1 | G3X807 | 100% | 78% | K16 | | 1 | | | | |
| S1 | G3X807 | 100% | 78% | R19 | | | | | 1 | 1 |
| S1 | G3N2B8 | 80% | 67% | K6 | | | | 1 | | |
| S1 | G3N2B8 | 80% | 67% | K9 | | | | 1 | | |
| S1 | G3N2B8 | 80% | 67% | K13 | | | | 1 | | |
| S1 | G3N2B8 | 80% | 67% | K17 | | | | 1 | | |
| S1 | G3N2B8 | 80% | 67% | R20 | | | | | 1 | |
| S1 | G3N2B8 | 80% | 67% | K21 | | 1 | | | | |
| S1 | G3N2B8 | 80% | 67% | R24 | | | | | 1 | 1 |
| S1 | F2Z4G5 | 100% | 81% | R89 | | | | | | 1 |
| S1 | F2Z4G5 | 100% | 81% | K96 | 1 | 1 | | | | |
| S1 | F2Z4G5 | 100% | 81% | K100 | 1 | 1 | | | | |
| S1 | A4IFUS | 100% | 81% | none | | | | | | |
| S1 | H2A2C | 100% | 81% | none | | | | | | |
| S1 | E1BH22 | 100% | 72% | none | | | | | | |
| S1 | F1MLQ1 | 100% | 48% | none | | | | | | |
| S1 | H2AJ | 56% | 44% | none | | | | | | |
| S1 | F1MMU4 | 100% | 10% | none | | | | | | |
| S1 | H2AV | 90% | 45% | none | | | | | | |
| S1 | H2AZ | 98% | 45% | none | | | | | | |
| S1 | Q0VC27 | 100% | 18% | none | | | | | | |
| S1 | Q2HJ65 | 100% | 14% | none | | | | | | |
| S1 | HP1B3 | 100% | 4% | none | | | | | | |
| S1 | E1B8K6 | 100% | 7% | none | | | | | | |
| S1 | A5D7M6 | 100% | 9% | none | | | | | | |
| S1 | E1B8N6 | 100% | 5% | none | | | | | | |
| S1 | F1N7I5 | 99% | 1% | none | | | | | | |
| S1 | F1MK30 | 100% | 12% | none | | | | | | |
| S1 | VIME | 99% | 3% | none | | | | | | |
| S1 | H10 | 85% | 0% | none | | | | | | |
| S1 | ACTA | 99% | 9% | none | | | | | | |
| S1 | RL6 | 75% | 0% | none | | | | | | |
| S1 | Q1LZ92 | 100% | 2% | none | | | | | | |
| S1 | F6S1Q0 | 100% | 4% | none | | | | | | |

TABLE 6-continued

List of proteins and PTMs identified in each fraction.

| Fraction | Accession | Probability | Coverage | PTM residue | Kme1 | Kme2 | Kme3 | Kac | Rme1 | Rme2 |
|---|---|---|---|---|---|---|---|---|---|---|
| S1 | P04264 | 99% | 3% | none | | | | | | |
| S2 | G3MWV5 | 100% | 21% | K34 | 1 | | | 1 | | |
| S2 | G3MWV5 | 100% | 21% | K46 | | | | 1 | | |
| S2 | E1B8G9 | 100% | 9% | R93 | | | | | 1 | |
| S2 | G3MWH4 | 100% | 13% | none | | | | | | |
| S2 | H31 | 100% | 41% | K19 | | | | 1 | | |
| S2 | H31 | 100% | 41% | K24 | | | | 1 | | |
| S2 | H31 | 100% | 41% | K80 | 1 | 1 | | | | |
| S2 | H3C | 85% | 17% | K80 | 1 | 1 | | | | |
| S2 | G3X807 | 100% | 59% | none | | | | | | |
| S2 | G3N2B8 | 76% | 50% | K6 | | | | 1 | | |
| S2 | G3N2B8 | 76% | 50% | K9 | | | | 1 | | |
| S2 | G3N2B8 | 76% | 50% | K13 | | | | 1 | | |
| S2 | G3N2B8 | 76% | 50% | K17 | | | | 1 | | |
| S2 | A4IFUS | 70% | 20% | none | | | | | | |
| S2 | H2A2C | 75% | 12% | none | | | | | | |
| S2 | E1BH22 | 94% | 11% | none | | | | | | |
| S2 | F1MLQ1 | 65% | 20% | none | | | | | | |
| S2 | Q0VC27 | 100% | 24% | none | | | | | | |
| S2 | Q2HJ65 | 100% | 3% | none | | | | | | |
| S2 | HP1B3 | 96% | 6% | none | | | | | | |
| S2 | E1B8K6 | 100% | 2% | none | | | | | | |
| S2 | A5D7M6 | 100% | 5% | none | | | | | | |
| S2 | E1B8N6 | 100% | 5% | none | | | | | | |
| S2 | F1N7I5 | 100% | 2% | none | | | | | | |
| S2 | F1MK30 | 99% | 3% | none | | | | | | |
| S2 | VIME | 100% | 6% | none | | | | | | |
| S2 | P35527 | 100% | 7% | none | | | | | | |
| S2 | ACTA | 100% | 3% | none | | | | | | |
| S2 | RL6 | 99% | 8% | none | | | | | | |
| S2 | Q1LZ92 | 100% | 2% | none | | | | | | |
| S2 | F6S1Q0 | 100% | 9% | none | | | | | | |
| S3 | H13 | 97% | 24% | K17 | | | 1 | 1 | | |
| S3 | H13 | 97% | 24% | K35 | 1 | | | | | |
| S3 | H12 | 100% | 24% | K17 | | | | 1 | | |
| S3 | H12 | 100% | 24% | K34 | 1 | | | | | |
| S3 | G3MWH4 | 99% | 13% | none | | | | | | |
| S3 | H31 | 100% | 25% | K10 | | 1 | 1 | | | |
| S3 | H31 | 100% | 25% | K15 | | | | 1 | | |
| S3 | H31 | 100% | 25% | K28 | 1 | 1 | | 1 | | |
| S3 | H31 | 100% | 25% | K37 | 1 | 1 | | | | |
| S3 | H31 | 100% | 25% | K38 | 1 | 1 | | | | |
| S3 | G3X807 | 100% | 28% | R19 | | | | | | 1 |
| S3 | G3N2B8 | 92% | 40% | K6 | | | | 1 | | |
| S3 | G3N2B8 | 92% | 40% | K9 | | | | 1 | | |
| S3 | G3N2B8 | 92% | 40% | K13 | | | | 1 | | |
| S3 | G3N2B8 | 92% | 40% | K17 | | | | 1 | | |
| S3 | G3N2B8 | 92% | 40% | R24 | | | | | | 1 |
| S3 | A4IFUS | 73% | 42% | none | | | | | | |
| S3 | H2A2C | 71% | 7% | none | | | | | | |
| S3 | E1BH22 | 63% | 32% | none | | | | | | |
| S3 | F1MLQ1 | 63% | 15% | none | | | | | | |
| S3 | F1MMU4 | 100% | 20% | none | | | | | | |
| S3 | H2AV | 100% | 22% | none | | | | | | |
| S3 | H2AZ | 96% | 7% | none | | | | | | |
| S3 | Q0VC27 | 98% | 18% | none | | | | | | |
| S3 | Q2HJ65 | 100% | 3% | none | | | | | | |
| S3 | HP1B3 | 100% | 6% | K535 | | 1 | 1 | | | |
| S3 | HP1B3 | 100% | 6% | K538 | 1 | 1 | 1 | | | |
| S3 | HP1B3 | 100% | 6% | K542 | 1 | 1 | 1 | | | |
| S3 | HP1B3 | 100% | 6% | K544 | | 1 | 1 | | | |
| S3 | HP1B3 | 100% | 6% | K548 | 1 | 1 | | | | |
| S3 | HP1B3 | 100% | 6% | K549 | 1 | 1 | 1 | | | |

Measuring Performance

For analysis and visualization of resin performance, it is desirable to have a single value descriptor of resin efficiency. In some embodiments, this can be achieved by measuring the ratio of KMe3/K variant peptides in the supernatant, and then taking the ratio of those values determined before and after compound and/or conjugate addition. The resulting value, termed "enrichment," represents the ratio of KMe3 to K variant peptides after resin addition divided by the ratio prior to resin addition (which was 1:1). Enrichment is then a simple numeric descriptor of the relative ratio of changing supernatant peptide levels after resin addition. Using such a descriptor, an enrichment value of 1 indicates no change in ratio after resin addition, while values lower than 1 represent a supernatant enriched for K (and depleted of KMe3) after resin addition. For example, 0.5 would represent 2× more K to KMe3 in the supernatant while 0.10 would represent 10× more K to KMe3. A higher ratio of K in the supernatant correlates with more KMe3 bound by the resin and so when using this term to describe an experimental outcome, lower values imply higher discrimination of KMe3. This value is a useful estimate of resin effectiveness when the total peptide bound is relatively low.

The enrichment value described above indicates nothing about the total amount of peptide bound to the resin. The total fraction of peptide remaining free after the addition of resin is also a useful value. This value gives an idea of the total affinity of the resin for both peptides without making comment on discrimination between. Total fraction free can be calculated from the standard-corrected AUC measurements of the levels of peptide in the supernatant before and after peptide addition. In this case, a lower fraction free indicates a higher affinity resin. The baseline value for this is roughly 0.85 as sample is diluted roughly 15% during resin addition and this dilution was not corrected for.

Example 1

In this example, the activity of various compound embodiments described herein were evaluated. A calixarene parent compound and compounds 502 and 404 were evaluated. Compound 502 was used has an upper-rim aryl group attached via sulfonamide linkage, and also includes a distal carboxy group for conjugation to solid-phase supports. The solution-phase affinities of a calixarene parent compound, and compounds 502 and 404 were determined for various methyllysine and methylarginine containing peptides by fluorescence indicator displacement assay (Table 1). Compound 502 exhibited sub-micromolar affinities for Kme2, Kme3, and aDMA-containing peptides, and weaker binding to unmethylated controls and Kac containing peptides. It can bind both H3K4me3 and H3K9me3 peptides, indicating that it is less sensitive to the sequence surrounding a particular methylation site than it is to the absence/presence of the trimethyllysine residue itself. The parent calixarene and compound 404 have distinct solution-phase equilibrium dissociation constant profiles, but like compound 502 show sub-micromolar affinities for Kme2 and Kme3, and weaker binding to unmethylated controls and Kac containing peptides (Table 7).

was complete, the conjugate 502-SC was filtered, washed extensively with MeOH and $H_2O$, and packed into a standard 1 mL glass column (6.2×35 mm) or a Teflon capillary column (1×600 mm).

Chromatography was performed using a test set of peptides representing varied lengths, charges, and methylation states of types that would be expected in a typical methylation-driven proteomics experiment. 7-mer peptides represented histone 3 residues 24-30, bracketing well known methylation site H3K27 and having net charge of +2. 12-mer peptides represent histone 3 residues 1-12, home to both H3K4 and H3K9 methylation sites and bearing an overall charge of +5.

Figure 1B:
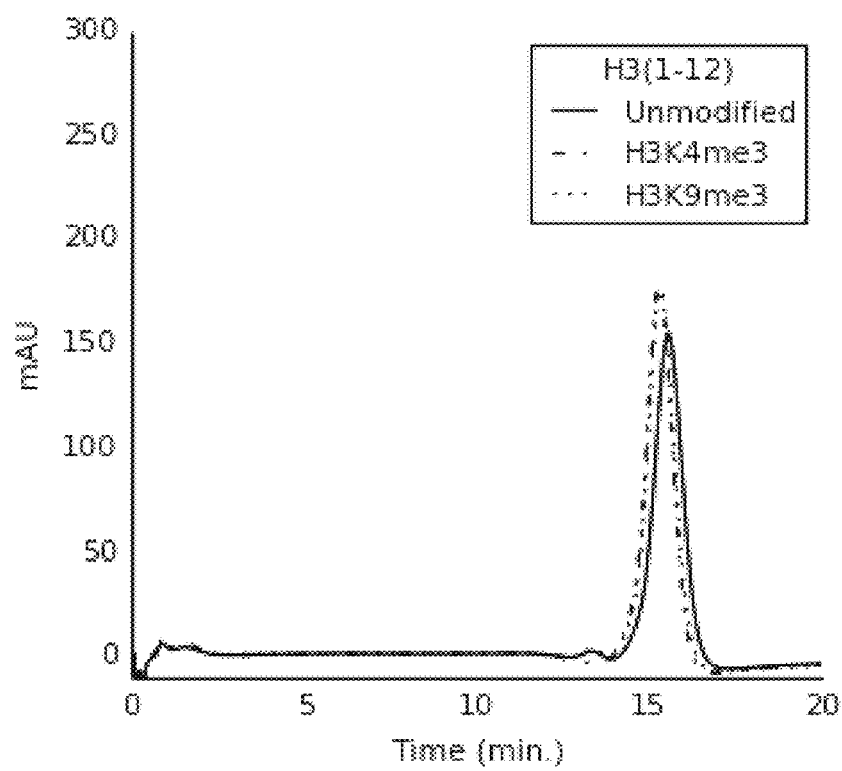

The sulfonates of the affinity reagent 502-SC provide a solid-phase reagent with strong cation-exchange functionality. To provide a baseline for understanding its behavior, chromatographic analyses were initiated with a commercial strong cation exchange resin that is also made from cross-linked agarose and that also bears sulfonates as its ion-exchanging groups (SPXL, GE Healthcare). FIGS. 1A and 1B shows the results of running various methylated and unmethylated peptide samples on this column using the manufacturer's suggested conditions (running buffer: 50 mM $NaH_2P_4$ pH 7.5; elution buffer: running buffer plus 1 M NaCl). The commercial column cannot resolve analytes on the basis of methylation. Chromatograms arising from matched sets of analytes with and without Kme3 modifications are identical for 7-mer peptides (FIG. 1A) and 12-mer peptides (FIG. 1B). Attempts to optimize the elution buffer did not give the SPXL column the ability to resolve methylated and unmethylated peptides.

A column comprising conjugate 502-SC retained analytes much more strongly than did SPXL. Histone-derived peptides would not elute from the column using the SPXL running buffer/elution buffer time program. The test peptides eluted with reasonable retention times and peak shapes when the elution buffer was changed from its original value of 1 M NaCl to 2 M $NH_4Cl$.

Figure 2A:
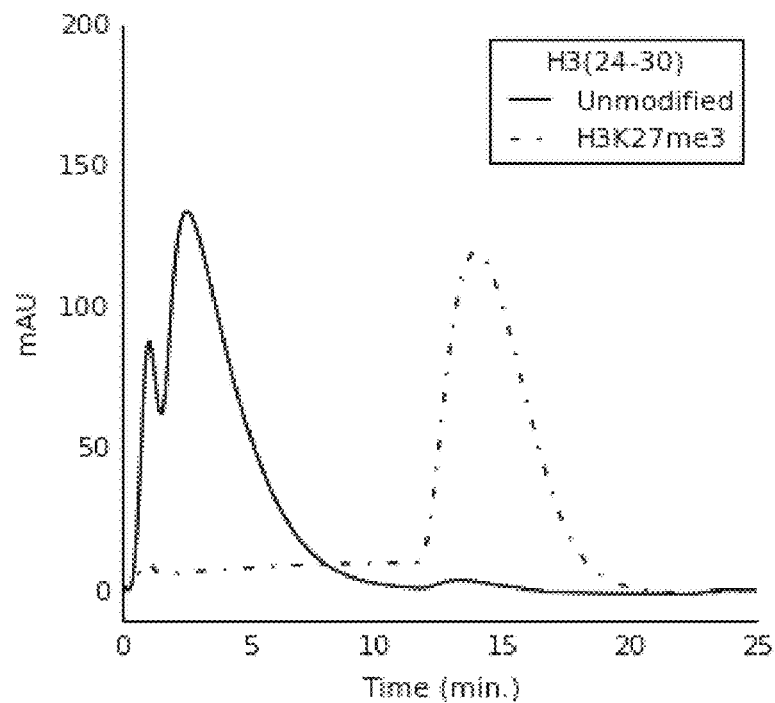
FIGS. 2A and 2B are chromatograms of 7-mer (+2 charge) peptides (FIG. 2A) and 12-mer (+5 charge) peptides (FIG. 2B) run on a column comprising a representative compound described herein; the chromatograms illustrate that the representative compound can resolve peptides on the basis of methylation.
Figure 2B:
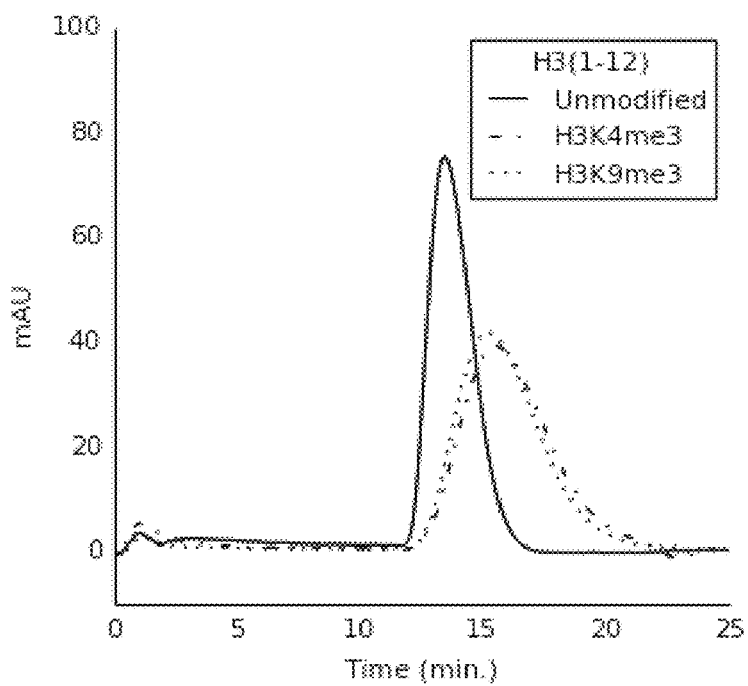

FIGS. 2A and 2B show that the 1 mL column of 502-SC retains peptides differently on the basis of their methylation. The 7-mer peptides based on H3K27 and H3K27me3 (having net charge of +2 each) elute separately, and are baseline separated when co-injected (FIG. 2A). The longer peptides

TABLE 7

Solution-phase equilibrium dissociation constants ($K_d$) of selected affinity reagents (a parent calixarene compound, 502, and 404 for a panel of PTM-containing peptides.

| Kd μM | H3K4 | H3K4me | H3K4me2 | H3K4me3 | H3K4ac | H3R2me2s | H3R2me2a | H3K9me3 |
|---|---|---|---|---|---|---|---|---|
| 1 | 3.6 | 1.9 | 0.7 | 0.5 | 14.6 | 4.9 | 2.0 | 1.2 |
| 2 | 3.8 | 1.3 | 0.4 | 0.2 | 7.6 | 2.6 | 0.6 | 0.5 |
| 3 | 85.5 | 2.3 | 0.1 | 0.2 | >1000 | 6.62 | 1.0 | 1.0 |

All values were determined in 10 mM phosphate buffer at pH 7.4 and are averages of triplicate determinations by an indicator displacement assay.

Compound 502 was conjugated to a cross-linked agarose support component by reaction with aminopropyl-functionalized AffiGel-102 (BioRad) using the peptide coupling agent EDC. Reaction progress was followed by observing the depletion of calixarene reagent from the supernatant using LCMS. Minimal calixarene depletion was observed before EDC addition, showing that nonspecific adsorption of the reagents to the resin was not occurring. After coupling based on H3(1-12) have net charge of +5 each, and are only partially resolved under the same running conditions (FIG. 2B).

Figure 3A:
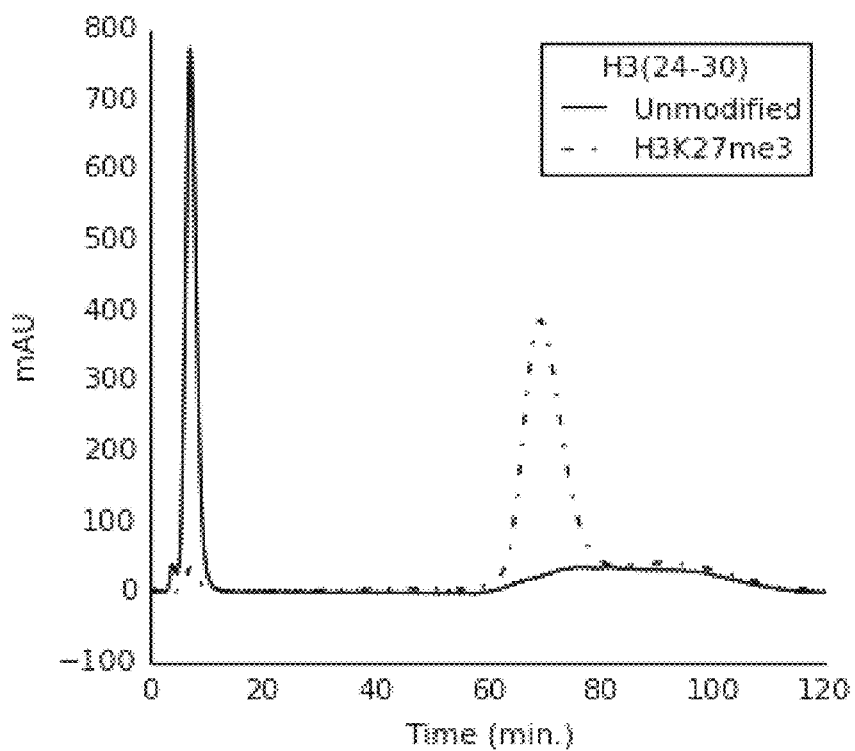
FIGS. 3A and 3B are chromatograms showing that a capillary column form factor improves resolution; the chromatograms were obtained from using a capillary column (1×600 mm) containing a stationary phase compound-containing conjugate treated with 7-mer (+2 charge) peptides (FIG. 3A) and 12-mer (+5 charge) peptides (FIG. 3B) with or without trimethyllysine marks.
Figure 3B:
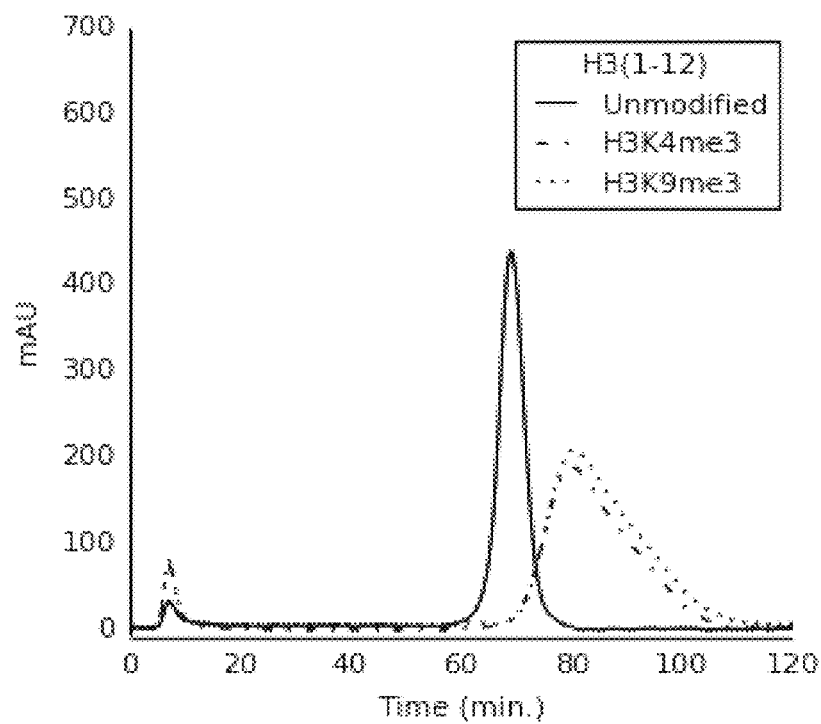
Figure 4A:
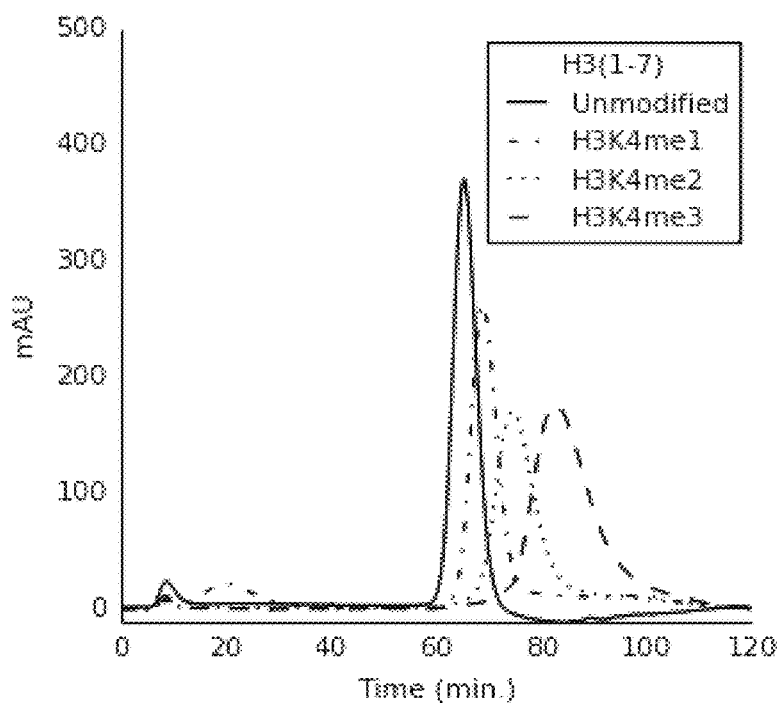
FIGS. 4A and 4B are chromatograms illustrating that the degree of methylation can be resolved, and other post-translational modification states, like lysine acetylation, can be resolved using representative compounds/conjugates; the chromatograms were obtained from a capillary column (1×600 mm) containing a stationary compound treated with 7-mer peptides bearing no modification, Kme1, Kme2, or Kme3 marks (FIG. 4A) or bearing no modification, Kac, aDMA, or sDMA marks (FIG. 4B).
Figure 4B:
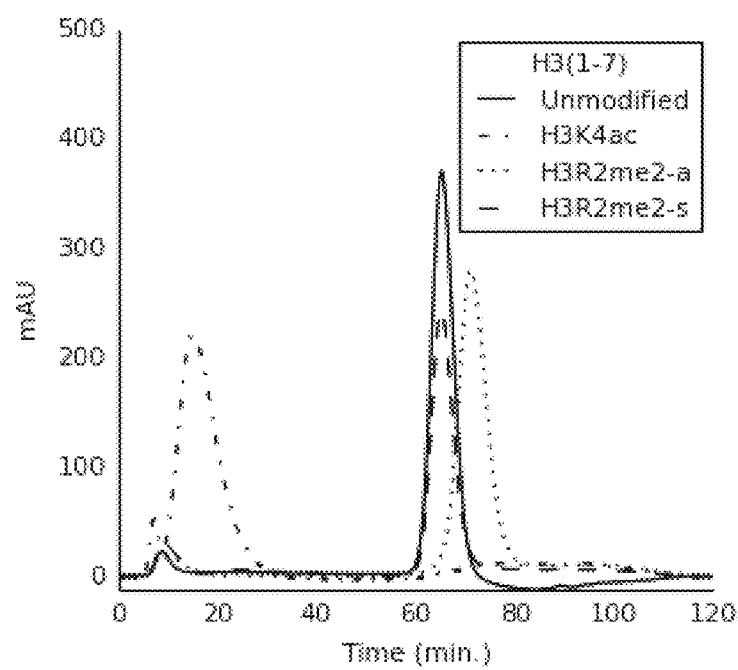

FIGS. 3A and 3B show the impact of changing to the longer, skinnier capillary column (1×600 mm). Chromatograms for 7-mer (+2) peptides are still cleanly resolved (FIG. 3A), and the 12-mer peptides H3K4me3 and H3K9me3 are better resolved (FIG. 3B) from their unmethylated counterpart. The traces in FIGS. 4A and 4B show how more subtly different methylation states behave on the column comprising 502-SC. FIG. 4A is a chromatograms arising from capillary column (1×600 mm) containing a stationary phase of 502-SC treated with 7-mer peptides bearing no modification, Kme1, Kme2, or Kme3 marks and FIG. 4B is a chromatogram showing results for 7-mer peptides bearing no modification, Kac, aDMA, or sDMA marks. Acetyllysine, as expected of a charge-neutralizing modification, causes dramatic reduction in retention times of analyte H3K4ac. Mono-, di-, and trimethyllysine provide incrementally longer retention times than the unmethylated control. Asymmetric dimethyl arginine (aDMA) is retained better than is symmetric dimethylarginine (sDMA), in line with the solution phase affinities determined for these two analytes.

Without being limited to a particular theory of operation, it is currently believed that the compounds disclosed herein operate via post-translational modification-specific affinity (e.g., methyl-specific affinity) layered on top of a background of very strong electrostatic attraction (e.g., ion exchange). Tuning the elution conditions can provide a series of chromatograms that indicate some degree of 'pan-specific' affinity for all kinds of post-translational methylations. The identities of analytes that are or are not retained are qualitatively connected to the solution-phase affinities in Table 7 (e.g., analytes with lower affinities as determined in the simple phosphate buffer for indicator displacement assays are not well retained by the column).

Figure 5:
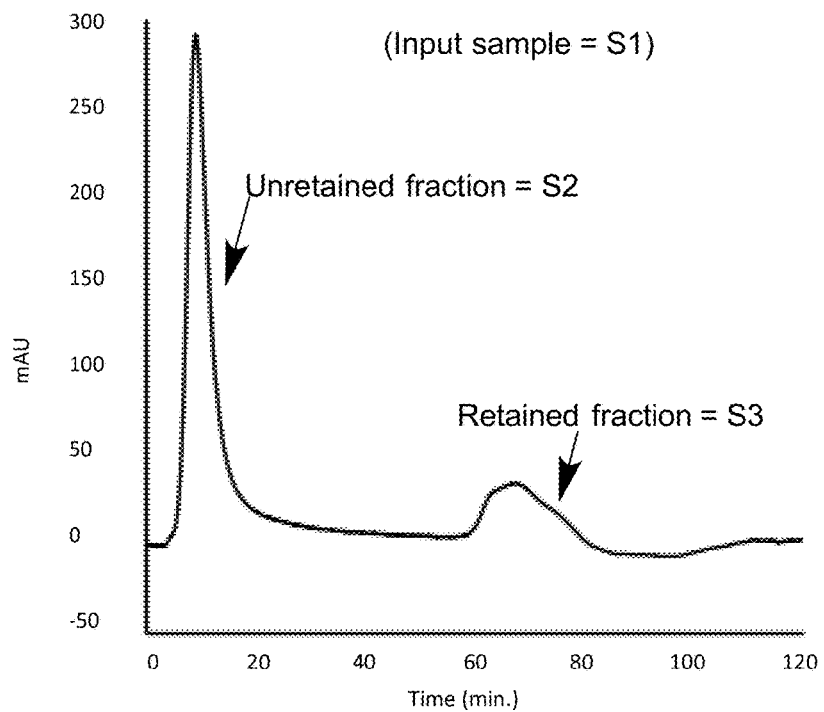
FIG. 5 is a chromatogram illustrating results from calf thymus histones that were digested with ArgC and separated on a capillary column comprising a representative compound.

Particular disclosed embodiments concern making methylation-seeking proteomics experiments possible without resorting to antibody-based reagents. The degree of charge on peptides in proteomics samples would likely range from +2 (in which case desirable resolution of methylated analytes can be obtained) to +5 (which, in some embodiments may result in some unmethylated analytes to elute along with the retained fraction). In some embodiments, a nuclear histone extract comprising calf thymus histones was used as a sample that would provide convenient access to challenging, heterogeneous mixtures of strongly cationic analytes containing many kinds of post-translational modifications. These 'calf thymus histone' samples included at least 38 identified proteins, including core histones, linker histones, histone variants, and multiple other proteins (Table 8). Many are annotated as DNA binders or other nuclear factors, explaining their presence in this sample. The sample was proteolyzed with ArgC prior to running on a capillary column comprising 502-SC. The chromatogram (FIG. 5) exhibits a typical elution profile, with the bulk of the sample eluting early and a small peak eluting at ca. 60 minutes.

TABLE 8

List of proteins identified in each fraction.

| Fraction S1 (input) Nickname | Accession | Fraction S2 (unretained) Nickname | Accession | Fraction S3 (retained) Nickname | Accession |
|---|---|---|---|---|---|
| 60S ribosomal protein | F1MK30 | 60S ribosomal protein | F1MK30 | HP1 Binding protein 3 | HP1B3 |
| 60S ribosomal protein | RL6 | 60S ribosomal protein | RL6 | High mobility group AT-hook 1 | Q0VC27 |
| Actin, aortic smooth muscle | ACTA | Actin, aortic smooth muscle | ACTA | Histone H1.2 | H12 |
| HP1 Binding protein 3 | HP1B3 | HP1 Binding protein 3 | HP1B3 | Histone H1.3 | H13 |
| High mobility group AT-hook 1 | Q0VC27 | High mobility group AT-hook 1 | Q0VC27 | Histone H2A | A4IFUS |
| Histone H1.0 | H10 | Histone H2A | A4IFUS | Histone H2A | E1BH22 |
| Histone H1.2 | H12 | Histone H2A | E1BH22 | Histone H2A | F1MLQ1 |
| Histone H2A | A4IFUS | Histone H2A | F1MLQ1 | Histone H2A | H2A2C |
| Histone H2A | E1BH22 | Histone H2A | H2A2C | Histone H2A | Q2HJ65 |
| Histone H2A | F1MLQ1 | Histone H2A | Q1LZ92 | Histone H2A.V | H2AV |
| Histone H2A | F2Z4G5 | Histone H2A | Q2HJ65 | Histone H2A.Z | H2AZ |
| Histone H2A | H2A2C | Histone H2B | E1B8G9 | Histone H3.1 | H31 |
| Histone H2A | Q1LZ92 | Histone H3.1 | H31 | Histone H4 | G3N2B8 |
| Histone H2A | Q2HJ65 | Histone H3.3C | H3C | Histone H4 | G3X807 |
| Histone H2A.J | H2AJ | Histone H4 | G3N2B8 | uncharacterized | F1MMU4 |
| Histone H2A.V | H2AV | Histone H4 | G3X807 | uncharacterized | G3MWH4 |
| Histone H2A.Z | H2AZ | KRT5 protein | A5D7M6 | | |
| Histone H2B | E1B8G9 | SWISS-PROT: P35527 | P35527 | | |
| Histone H2B | F1MVX6 | uncharacterized | E1B8K6 | | |
| Histone H2B | F2Z4F9 | uncharacterized | F1N7I5 | | |
| Histone H2B | G3N080 | uncharacterized | F6S1Q0 | | |
| Histone H2B | G5E6I9 | uncharacterized | G3MWH4 | | |
| Histone H3.1 | H31 | uncharacterized | G3MWV5 | | |
| Histone H3.3C | H3C | Vimentin | VIME | | |
| Histone H4 | G3N2B8 | | | | |
| Histone H4 | G3X807 | | | | |
| KRT5 protein | A5D7M6 | | | | |
| SWISS-PROT: P04264 | P04264 | | | | |
| uncharacterized | E1B8K6 | | | | |
| uncharacterized | E1B8N6 | | | | |
| uncharacterized | F1MMU4 | | | | |
| uncharacterized | F1N7I5 | | | | |
| uncharacterized | F6S1Q0 | | | | |

TABLE 8-continued

List of proteins identified in each fraction.

| Fraction S1 (input) Nickname | Accession | Fraction S2 (unretained) Nickname | Accession | Fraction S3 (retained) Nickname | Accession |
|---|---|---|---|---|---|
| uncharacterized | G3MWH4 | | | | |
| uncharacterized | G3MWV5 | | | | |
| Vimentin | VIME | | | | |

The input sample ("S1"), the unretained fraction ("S2"), and the retained fraction ("S3"), were subjected to LC-MS/MS analysis (Table 9). Peptide sequences and post-translational modification states/sites were determined by molecular weight and MS/MS fragmentation patterns using Mascot (for protein identification) and Scaffold (for PTM analysis). Peptide identities were assigned by comparison to the Bos taurus proteome.

TABLE 9

Properties of the column as revealed by analyzing peptide sets identified in each fraction.

| Fraction | # residues | MW (Da) | Charge[b] |
|---|---|---|---|
| S1 (input) | 22 ± 13 | 2340 ± 1720 | 1.7 ± 1.4 |
| S2 (unretained) | 15 ± 6 | 1560 ± 520 | 0.6 ± 1.8 |
| S3 (retained) | 17 ± 9 | 1740 ± 840 | 2.1 ± 2.0 |

Uncertainties are reported as standard deviations.
[b]Gas-phase charge states are not relevant to the properties of the peptides while being eluted.
The mean solution-phase charges on the peptides at pH 7.4 were predicted by totaling the number of cationic and anionic side chains.

The column behaves as predicted by studies with pure peptides even when handling complex mixtures. There is no significant retention bias based on peptide size or molecular weight (Table 8). From the differences in peptide charges between unretained and retained fractions it can be concluded that the column is acting partially as a cation exchanger, but the large standard deviations for each value show that its behavior is not dominated exclusively by peptide charge.

In some examples, K and KMe3 variants of the synthetic AARKSAPY and ARTKQTARKSTGY peptides with propionic anhydride to get an idea of how propionylation would affect retention. Assuming it has been fully propionylated, this would lead to a reduction in the net charge on the ARTKQTARKSTGY K variant peptide from +5 to +2 with both lysine residues and the N-terminal amine being propionylated, while the K4Me3 and K9Me3 variants would end up with a total charge of +3 after propionylation. After propionylation the ARTKQTARKSTGY K variant was no longer well retained and instead eluted early, in the first column volume. The propionylated ARTKQTARKSTGY K9Me3 variant was partially retained with a portion of the peptide eluting early and a smaller portion being retained until the elution buffer was applied. The double elution profile suggests that a portion of peptide may not have been fully propionylated and as such was more strongly retained by the column. Future studies should confirm complete propionylation via LCMS. The AARKSAPY peptide, which was poorly retained to begin with, eluted even more quickly. The AARKSAPY KMe3 peptide, which should be not react with propionic anhydride as it does not have a free K residue, was similarly retained before and after treatment with propionic anhydride. These results collectively show that propionylation of peptides using protocols identical to those used in the preparation of proteomics samples may improve the column's ability to separate analytes on the basis of lysine methylation.

Figure 6:
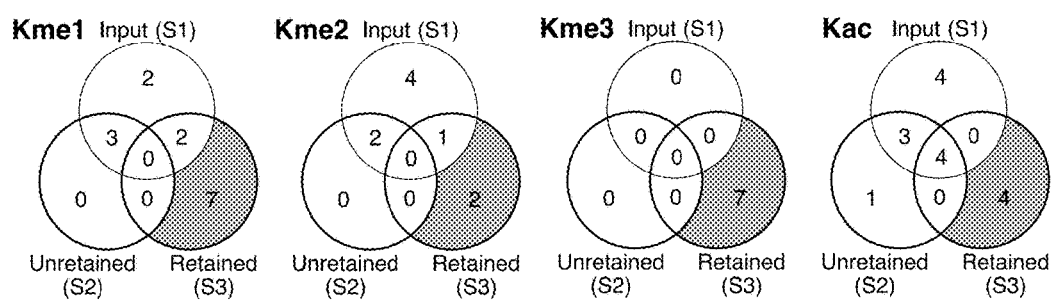
FIG. 6 illustrates Venn diagrams showing that fractionation on columns comprising representative compounds helps to identify otherwise unobserved modification sites; unique and shared observations of particular Kme1, Kme2, Kme3, and Kac sites in each fraction from analyzing calf thymus histone extract are illustrated and the PTM sites uniquely observed in the retained fraction S3 after chromatography are in the shaded sector.

The column comprising 502-SC improves observation of Kme methylation marks. Together, Kme, Kme2, Kme3 modifications are more often observed in the retained fraction (S3; total of 26 sites) relative to the unretained fraction (S2, total of 5 sites) (Table 10). These results are consistent with the tendency of the column to retain methyllysine peptides. Kme3 sites are not identified in the input S1 fraction, while 7 are identified in the retained S3 fraction. This shows that analytes that are present, but whose ionization is inefficient in the complex input mixture (S1) are identifiable after enrichment. In addition to showing more modification sites, retained fraction S3 contains several uniquely observed PTM sites of all kinds that are not observed in input sample S1 (FIG. 6). The unretained fraction S2 has zero Kme3 sites, and zero uniquely observed lysine methylation sites of any kind.

TABLE 10

Occurrence of post-translational modifications in peptides arising from ArgC-proteolysis of calf thymus histones before and after fractionation on a column comprising 502-SC.

| Fraction | Lysine PTMs (occurrences) | | | | | Arginine PTMs (occurrences) | | |
|---|---|---|---|---|---|---|---|---|
| | Kme1 | Kme2 | Kme3 | All Kme | Kac | Rme1 | Rme2 | All Rme |
| S1 (input) | 7 | 7 | 0 | 14 | 11 | 5 | 3 | 8 |
| S2 (unretained) | 3 | 2 | 0 | 5 | 8 | 1 | 0 | 1 |
| S3 (retained) | 9 | 10 | 7 | 26 | 8 | 0 | 2 | 2 |
| Sum | 19 | 19 | 7 | 45 | 27 | 6 | 5 | 11 |

Figure 7A:
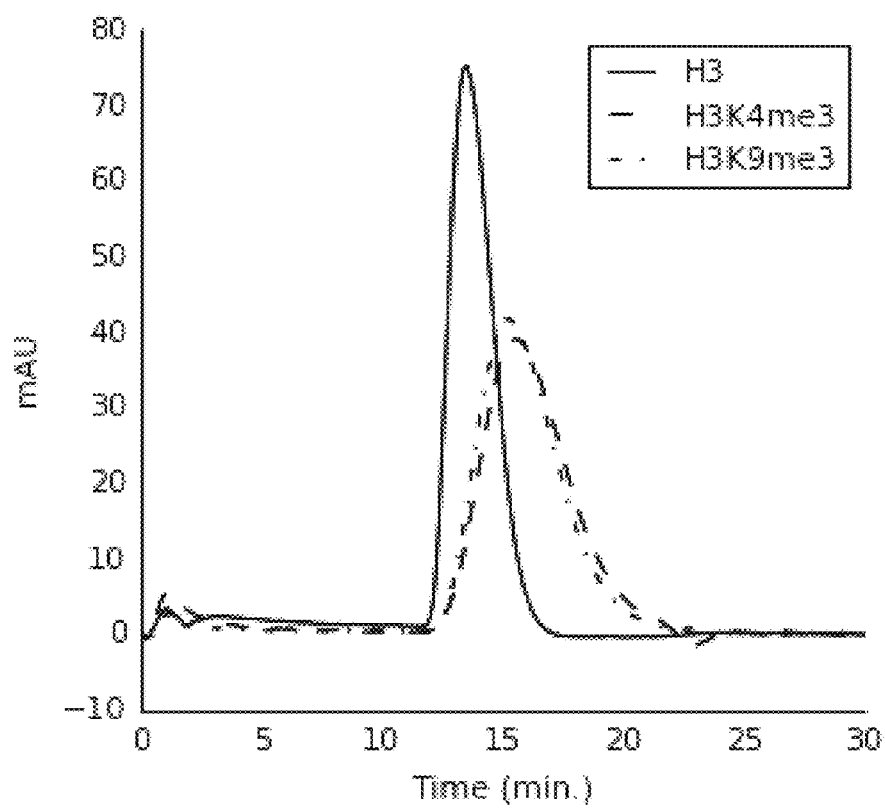
FIGS. 7A-7C illustrate additional chromatograms obtained from using representative compounds to separate peptides based on PTMs; adding NaCl to the running buffer helps improve separation as can be seen by comparing FIG. 7A (0 M NaCl) with FIG. 7B (0.2 M NaCl) and FIG. 7C (1 M NaCl).
Figure 7B:
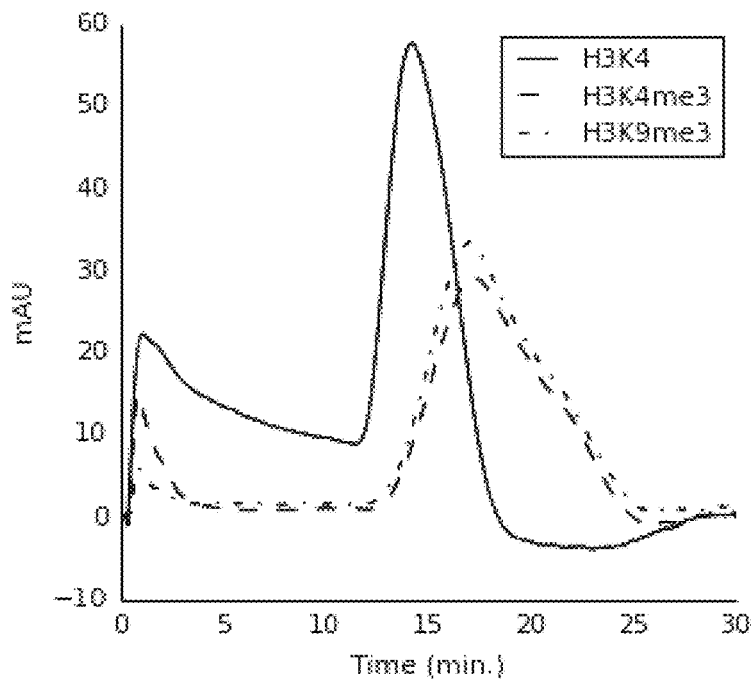
Figure 7C:
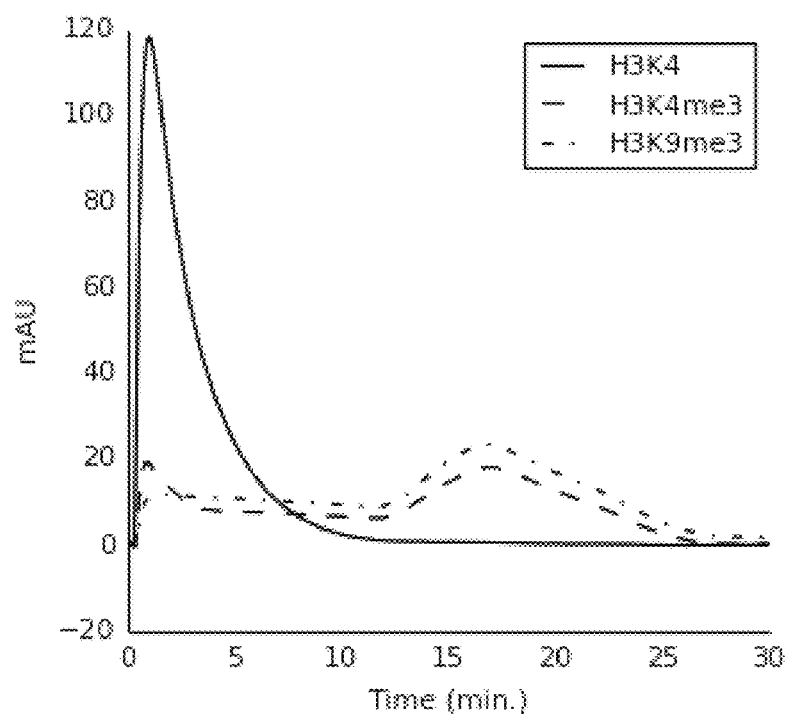

Additional results are shown in FIGS. 7A-7C. The results shown in FIGS. 7A-7C were obtained from embodiments where NaCl was added to the running buffer to improve separation. Chromatograms arising from capillary column (1×600 mm) containing stationary phase 502-SC treated with 12-mer peptides bearing no modification or trimethyllysines. Elutions conditions are as described above, except that running buffer contains 0 M NaCl (FIG. 7A) 0.2 M NaCl (FIG. 7B), or 1 M NaCl (FIG. 7C). Running buffer 50 mM phosphate at pH 7.5 containing the indicated amounts of NaCl. Elution buffer was 2 M $NH_4Cl$ in running buffer.

Figure 8:
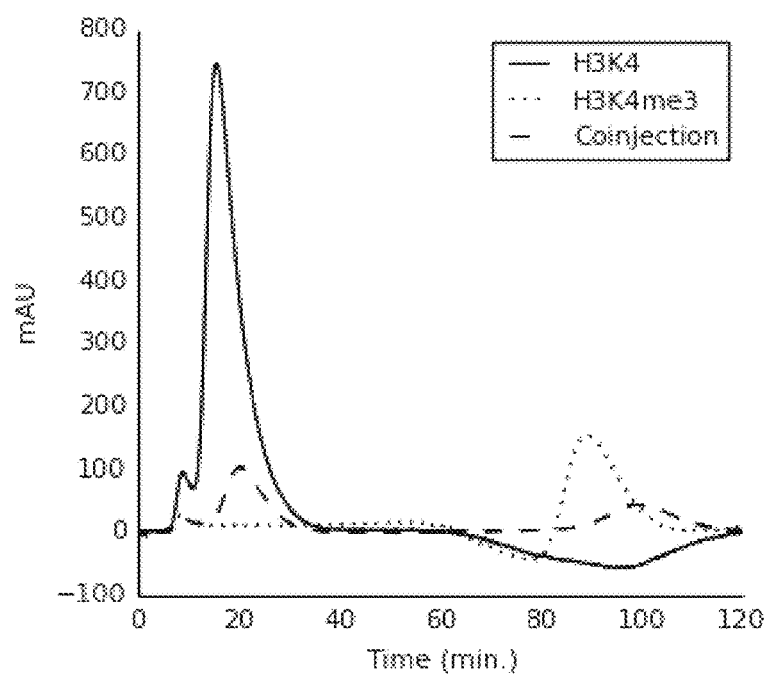
FIG. 8 is a chromatogram showing that a representative compound can be used to separate species on the basis of methylation.
Figure 9:
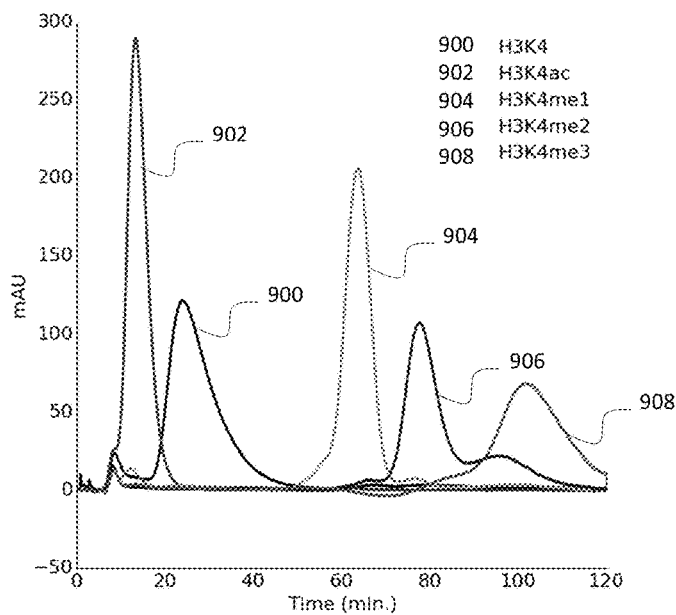
FIG. 9 is a chromatogram showing that a representative compound can be used to resolve Kac, K, Kme1, Kme2, and Kme3 peptides.

FIGS. 8 and 9 show results from using a disclosed conjugate in a column to achieve separation on the basis of methylation (FIG. 8), and the ability to resolve Kac, K, Kme1, Kme2, Kme3 peptides (FIG. 9). The chromatograms (FIGS. 8 and 9) arising from capillary column (1×600 mm) containing a stationary phase of a conjugate comprising compound 416 (referred to as 416-SC) treated with 7-mer peptides bearing no modification, Kac or methyllysines as indicated. The running buffer was 50 mM phosphate at pH 7.5 and the elution buffer was 2 M $NH_4Cl$ in running buffer.

Figure 10:
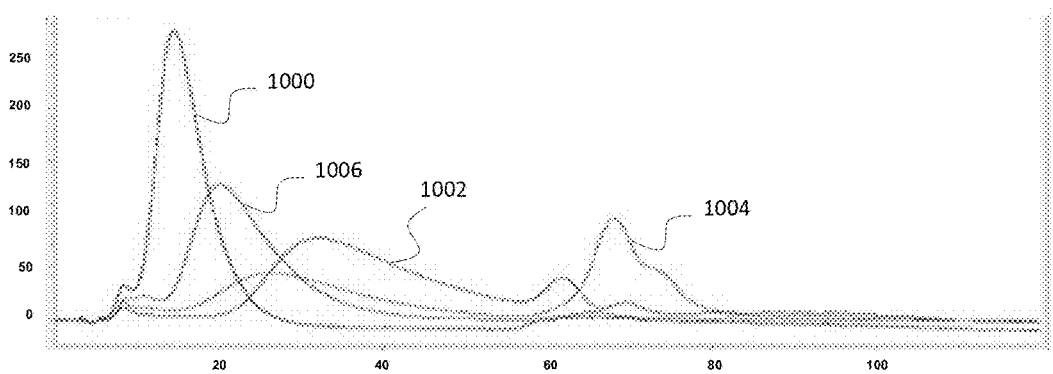
FIG. 10 is a chromatogram illustrating results obtained using a column comprising another representative compound; the compound is able to separate 12-mer peptides wherein H3K4 is trace 1000, H3K4Me3 is trace 1002, H3K4Me2 is trace 1004, and H3K4Me1 is trace 1006.
Figure 11:
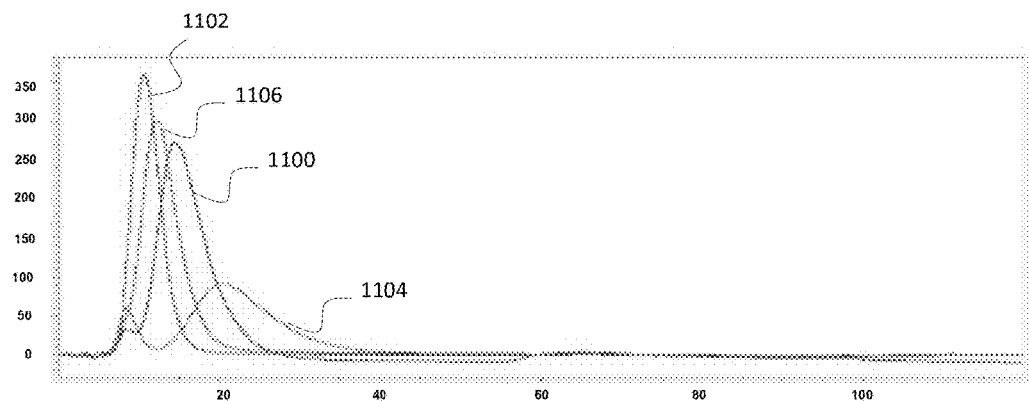
FIG. 11 is a chromatogram illustrating results obtained using a column comprising another representative compound; the compound is able to separate 12-mer peptides wherein H3K4 is trace 1100, H3K4Ac is trace 1102, H3R2 MeA is trace 1104, and H3R2 MeS is trace 1106.

Results from yet another representative conjugate are illustrated in FIGS. 10 and 11. The conjugate in this example exhibited distinct separation performance, including selectivity for forms of dimethylarginine and dimethyllysine. Chromatograms arising from capillary column (1×600 mm) containing a stationary phase of a conjugate comprising compound 414 (referred to as 414-SC) treated with 12-mer peptides (FIG. 10) H3K4 (trace 1000), H3K4Me3 (trace 1002), H3K4Me2 (trace 1004), H3K4Me1 (trace 1006) and (FIG. 11) H3K4 (trace 1100), H3K4Ac (trace 1102), H3R2 MeA (trace 1104), H3R2 MeS (trace 1106). The running buffer was 50 mM phosphate at pH 7.5 and the elution buffer was 2 M $NH_4Cl$ in running buffer. See methods for time program.

In some independent embodiments, a column comprising 502-SC does not provide benefit for the enrichment or analysis of methylarginine containing peptides. Rme1/Rme2 modifications are more readily seen in the input control S1 than in either of the eluted fractions S2 or S3.

Many canonical histone methylation sites are identified in the samples. H3K27 is expected to be highly abundant and is visible in both the input control and the enriched fraction S3. The lesser-known H3K69 is also found in both the input and the enriched fraction. H3K9, H3K27, and H3K36 are well known and found only in the enriched sample. The less well-known (and presumably less abundant) histone methylation at H3K37 is visible only in enriched sample S3 and not in the input S1.

Sample S3 contains multiple non-histone-derived peptides bearing methylated lysine residues. Among this limited data set, the multiple methylation sites identified on HP1-binding-protein-3 (HP1BP3) consist of a new discovery. HP1BP3 has been known to be acetylated, and heavily phosphorylated, but no reports of any methylation sites/states exist in the online databases UniProt or PhosphositePlus (a PTM-specific database). HP1B3 peptides are identified in both the input fraction S1 and the unretained fraction S2, but all lysine methylation sites and states seen for HP1BP3 are only visible after enrichment in the retained S3 fraction.

Example 2

In this example, conjugates described herein were used in chromatographic setups. In such embodiments, the conjugates are able to have multiple interactions with the analyte as it transits through the column, all of which will contribute to the separation. By increasing the length of the column, the number of theoretical plates should increase and so should the separation. In some examples, lectin-glycoprotein capillary columns or IMAC-phosphopeptide columns can be used. These are both examples of columns used for weak affinity chromatography (WAC), which uses low affinity reagents for the separation of analytes by differential retention, as opposed to antibody enrichment which is most typically performed in a batch-binding approach.

In some examples, reagents can have $K_{ass}=10^2-10^4$ $M^{-1}$ for effective WAC separations, and high loading can be achieved by immobilizing the reagents onto porous columns with a high surface area.

Columns were prepared by loading the respective resin into empty columns purchased from Agarose Bead Technologies as a gel slurry, as discussed above. To set a benchmark for comparison of these columns, a 1 mL HiTrap SPXL strong cation exchange column containing an agarose resin bearing simple monosulfonate head groups (GE Healthcare) was used as a control. To test the affinity of the columns for the KMe3 motif, stock peptide solution of the AARKSAPY peptide (K and KMe3 variants), the same used in the batch binding experiments, were prepared. In addition, longer peptides bearing the sequence of the H3 N-terminal sequence ARTKQTARKSTGY, with alternative K, K4Me3 and K9Me3 variation were also used. This longer peptide is more cationic bearing 2 lysine and 2 arginine residues in addition to a free N-terminal amine for a total 5+ charge. A trypsin digest of calf-thymus histone was also subjected to separation by the column.

Figure 17A:
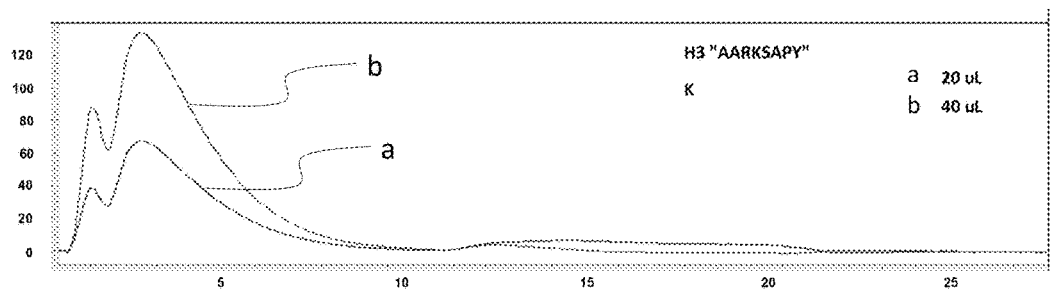
FIGS. 17A-17F are chromatogram traces showing the ability of representative compounds to resolve short peptides (FIGS. 17A-17D) and longer peptides (FIGS. 17E and 17F), and showing the ability to measure amounts of peptides by peak area.
Figure 17B:
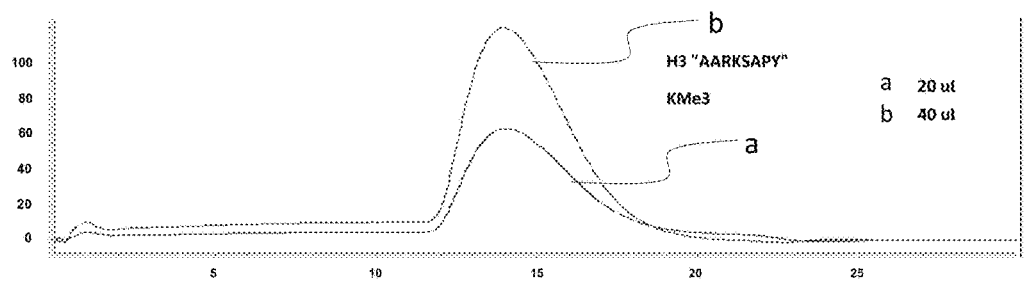
Figure 17C:
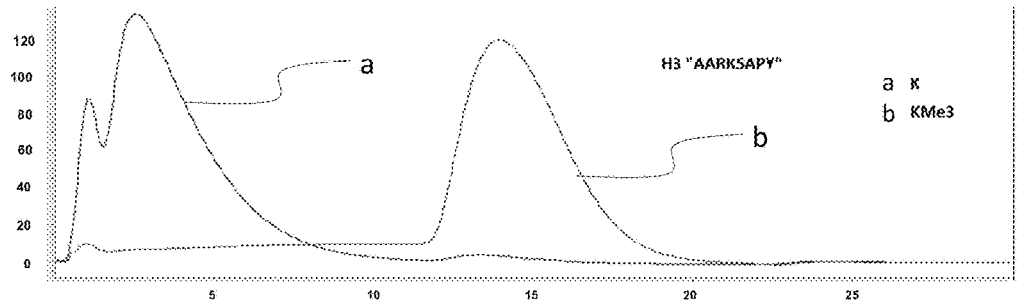
Figure 17D:
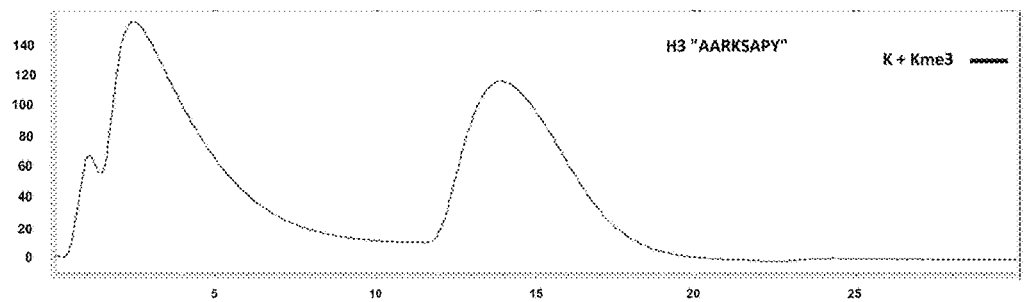
Figure 17E:
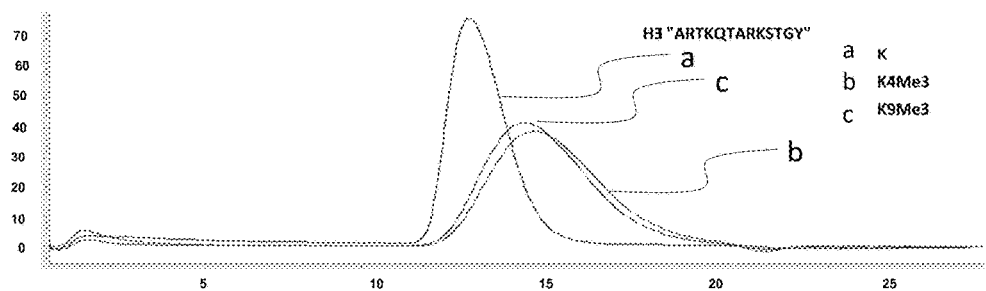
Figure 17F:
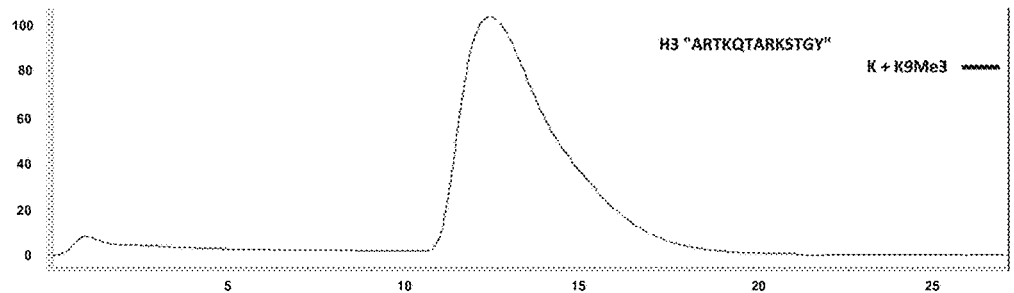

The application of an $NH_4Cl$ elution buffer was highly successful in promoting rapid elution of bound peptides from columns comprising disclosed conjugates. When applied to the AARKSAPY peptides, total discrimination between the AARKSAPY K and KMe3 variants was realized, with the KMe3 variant eluting from the column only after the elution buffer had been applied (FIGS. 17A-17F). Furthermore, when a sample containing both K and KMe3 variants was injected, total separation was achieved between the K and KMe3 variants confirming that separation from a mixture of the peptides on the basis of methylation (with no difference in charge) is possible (FIG. 17D). These result represent a dramatic success of the system when applied to relatively short 8-mer peptides. The longer and more highly cationic ARTKQTARKSTGY K, K4Me3 and K9Me3 variant peptides were only partly discriminated under these conditions. All peptides were retained and eluted as broad peaks with retention times of 13.5 min, 15.3 min and 15.5 min for the K, K9Me3 and K4Me3 variants, respectively, only after the elution buffer was applied (FIGS. 17E and 17F). Although there is significant overlap of K and K9Me3 variant peptides peaks, it should be possible to isolate pure fractions of either peptide from the early and late eluting fractions of the K and K9Me3 peaks, respectively.

Resolution between the K and KMe3 variants of the ARTKQTARKSTGY can be improved either by increasing the separation between the peaks or by sharpening the peaks themselves. Using a column comprising an exemplary conjugate, the peak shape was typically broad with peptides typically eluting over 3 or 4 minutes and often tailing somewhat. In an attempt to improve peak shape and better the separation of the ARTKQTARKSTGY peptides, small amounts of $NH_4Cl$ were introduced to the running buffer. Overall peak shape did seem to sharpen slightly; thus, inclusion of $NH_4Cl$ in the running buffer can be used to improve the separation of the ARTKQTARKSTGY peptides, as the K9Me3 variant peptide was less susceptible to the presence of NH$_4$Cl and was relatively well retained compared to the K variant.

In view of the many possible embodiments to which the principles of the present disclosure may be applied, it should be recognized that the illustrated embodiments are only preferred examples and should not be taken as limiting. Rather, the scope is defined by the following claims. We therefore claim as our invention all that comes within the scope and spirit of these claims.

We claim:

1. A conjugate, wherein the conjugate is a compound having a structure satisfying Formula I that is covalently coupled to a support component by at least one of A, E, G, J, L, M, N, or Q of Formula I, either directly or through an aliphatic linker, a heteroaliphatic linker, an aryl linker, or a heteroaryl linker, wherein Formula I is

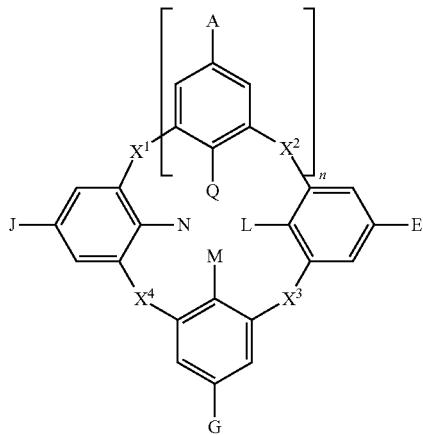

Formula I and wherein

G is aryl, heteroaryl, -linker-aryl, —SO$_3^-$, —SO$_3$H, or -linker-heteroaryl, wherein each linker independently is a sulfonamide;

each of A, E, and J independently is SO$_3^-$; —SO$_3$H; aryl; heteroaryl; -linker-aryl; or -linker- heteroaryl, wherein each linker independently is a sulfonamide;

M is —OH; —O$^-$; —O(CH$_2$)$_p$Y; —O(CH$_2$)$_p$Ph(CH$_2$)$_p$(Y)$_m$; —OC(O)Ph(CH$_2$)$_p$(Y)$_m$; or —OSO$_2$Ph(CH$_2$)$_p$(Y)$_m$; wherein each Y independently is alkyl, alkoxy, amide, thiol, thioether, aldehyde, carboxyl, ester, NH$_2$, or NH$_3^+$, p is an integer selected from 0 to 10, and m is an integer selected from 0 to 4;

each of L, N, and Q independently is —OH; —O$^-$; O(CH$_2$)$_p$Y; —O(CH$_2$)$_p$Ph(CH$_2$)$_p$(Y)$_m$; —OC(O)Ph(CH$_2$)$_p$(Y)$_m$; or —OSO$_2$Ph(CH$_2$)$_p$(Y)$_m$; wherein each Y independently is alkyl, alkoxy, amide, thiol, thioether, aldehyde, carboxyl, ester, NH$_2$, or NH$_3^+$, p is an integer selected from 0 to 10, and m is an integer selected from 0 to 4;

each of X$^1$, X$^2$, X$^3$, and X$^4$ is CH$_2$;

n is an integer selected from 1 to 3; and wherein if (i) each of G, A, E, and J are SO$_3^-$ and (i) M is —O(CH$_2$)$_p$Y wherein p is 1, then Y is selected from alkyl, alkoxy, thiol, thioether, NH$_2$, or NH$_3^+$.

2. The conjugate of claim 1, wherein the support component comprises a resin, a bead, a polymeric matrix, a metal oxide, a powder, a crystalline compound, an amorphous compound, or a combination thereof.

3. The conjugate of claim 1, wherein the support component comprises agarose, sepharose, cellulose, modified cellulose, dextran, polyacrylamide, polystyrene, latex, bonded silica gel, silica based solid, activated alumina, a polysaccharide polymer, a resinous polymer, or a combination thereof.

4. The conjugate of claim 1, wherein G is aryl, heteroaryl, —NR$^b$SO$_2$-aryl (wherein R$^b$ independently is hydrogen, aliphatic, heteroaliphatic, aryl, or heteroaryl), NR$^b$SO$_2$ heteroaryl (wherein R$^b$ independently is hydrogen, aliphatic, heteroaliphatic, aryl, or heteroaryl); and A, E, and J are —SO$_3^-$.

5. The conjugate of claim 1, wherein each aryl group independently is phenyl or phenyl substituted with an aliphatic moiety, a heteroaliphatic moiety, a halogen, a heteroatom-containing moiety, or a combination thereof.

6. The conjugate of claim 1, wherein each aryl group independently is phenyl substituted with an aliphatic moiety, a heteroaliphatic moiety, a halogen, a heteroatom-containing moiety, or a combination thereof, wherein the aliphatic moiety is alkyl, alkenyl, or alkynyl; the heteroaliphatic is moiety is alkoxy, ether, thioether, amine (—NHR$^b$, —NR$^b$R$^c$, or —(CH$_2$)$_p$NHR$^b$, wherein R$^b$ and R$^c$ independently are hydrogen, aliphatic, heteroaliphatic, aryl, or heteroaryl; and p is an integer selected from 0 to 10); the halogen is chloro, iodo, bromo, or fluoro; and the heteroatom-containing moiety is aldehyde (—(CH$_2$)$_p$C(O)H), acyl halide (—(CH$_2$)$_p$C(O)X, wherein X is selected from fluorine, chlorine, bromine, and iodine), carbonate (—(CH$_2$)$_p$OC(O)OR$^b$, wherein R$^b$ is hydrogen, aliphatic, heteroaliphatic, aryl, or heteroaryl), carboxyl (—(CH$_2$)$_p$C(O)OH), carboxylate (—(CH$_2$)$_p$COO$^-$), ester (—(CH$_2$)$_p$C(O)OR$^b$), hydroxyl (—(CH$_2$)$_p$OH), ketone (—(CH$_2$)$_p$C(O)R$^b$), peroxy (—(CH$_2$)$_p$OOR$^b$, wherein R$^b$ is hydrogen, aliphatic, heteroaliphatic, aryl, or heteroaryl), hydroperoxy (—(CH$_2$)$_p$OOH), phosphate (—(CH$_2$)$_p$OP(O)OH$_2$), phosphoryl (—(CH$_2$)$_p$P(O)(OH)$_2$), phosphodiester [—(CH$_2$)$_p$(O)P(OH)OR$^b$], wherein R$^b$ is hydrogen, aliphatic, heteroaliphatic, aryl, or heteroaryl], thiol (—(CH$_2$)$_p$SH), disulfide (—(CH$_2$)$_p$SSR$^b$, wherein R$^b$ is hydrogen, aliphatic, heteroaliphatic, aryl, or heteroaryl), sulfonate (—(CH$_2$)$_p$SO$_3^-$—, sulfinyl (—(CH$_2$)$_p$S(O)R$^b$, wherein R$^b$ is hydrogen, aliphatic, heteroaliphatic, aryl, or heteroaryl), sulfonate ester (—(CH$_2$)$_p$SO$_2$OR$^b$, wherein R$^b$ is hydrogen, aliphatic, heteroaliphatic, aryl, or heteroaryl), sulfonyl (—(CH$_2$)$_p$SO$_2$R$^b$, wherein R$^b$ is hydrogen, aliphatic, heteroaliphatic, aryl, or heteroaryl), carbonothioyl (—(CH$_2$)$_p$C(S)R$^b$ or —(CH$_2$)$_p$C(S)H, wherein R$^b$ is hydrogen, aliphatic, heteroaliphatic, aryl, or heteroaryl), sulfino (—(CH$_2$)$_p$S(O)OH), sulfo (—(CH$_2$)$_p$SO$_3$H), thiocyanate (—(CH$_2$)$_p$SCN), isothiocyanate (—(CH$_2$)$_p$NCS), oxazole, oxadiazole, imidazole, triazole, tetrazole, amide (—(CH$_2$)$_p$C(O)NR$^b$R$^c$, wherein R$^b$ and R$^c$ independently are hydrogen, aliphatic, heteroaliphatic, aryl, or heteroaryl), azide (—(CH$_2$)$_p$N$_3$), azo (—(CH$_2$)$_p$NNR$^b$, wherein R$^b$ is hydrogen, aliphatic, heteroaliphatic, aryl, or heteroaryl), isocyanate (—(CH$_2$)$_p$NCO), imide (—(CH$_2$)$_p$C(O)NR$^b$C(O)R$^b$, wherein R$^b$ and R$^b$ independently are hydrogen, aliphatic, heteroaliphatic, aryl, or heteroaryl), nitrile (—(CH$_2$)$_p$CN), isonitrile (—(CH$_2$)$_p$N$^+$=C$^-$), nitro (—(CH$_2$)$_p$NO$_2$), nitroso (—(CH$_2$)$_p$NO), nitromethyl (—(CH$_2$)$_p$CH$_2$NO$_2$), or —(CH$_2$)$_p$NH$_2$, wherein each p independently is an integer selected from 0 to 10.

7. The conjugate of claim 1, wherein:

each of A, E, and J independently is —SO$_3^-$, or —NHSO$_2$Ph(CH$_2$)$_p$(Y)$_m$, wherein each Y independently is positioned ortho, meta, or para on the Ph group and is aliphatic, aryl, halogen, heteroaliphatic, heteroaryl, a heteroatom-containing function group, or a combination thereof, each m is an integer selected from 0 to 4, and each p is an integer selected from 0 to 10; and
n is 1.
8. The conjugate of claim 1, wherein the compound has a formula
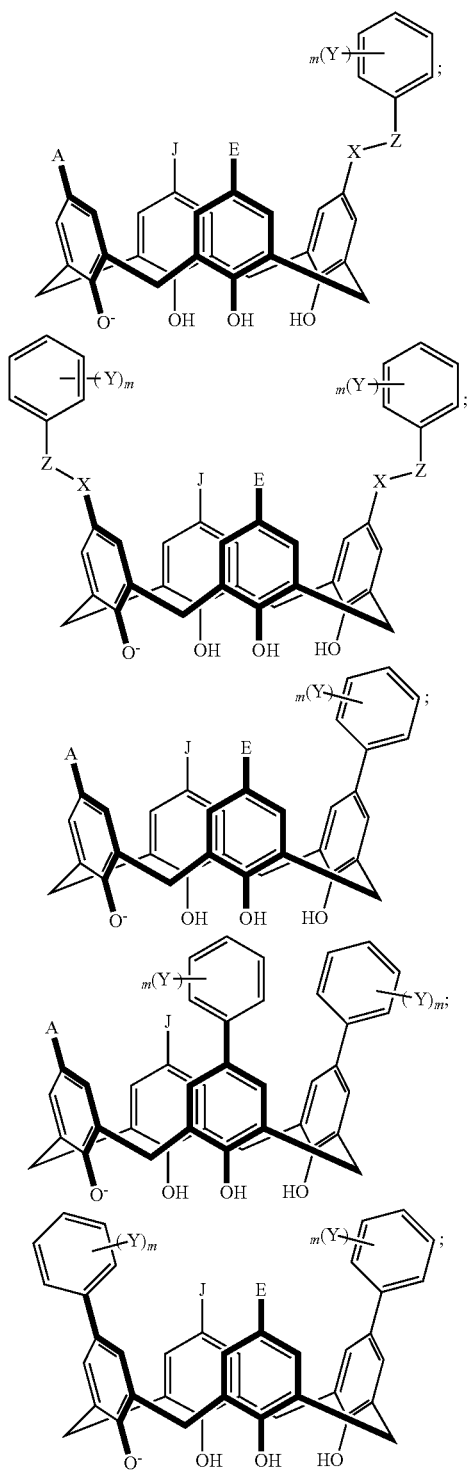
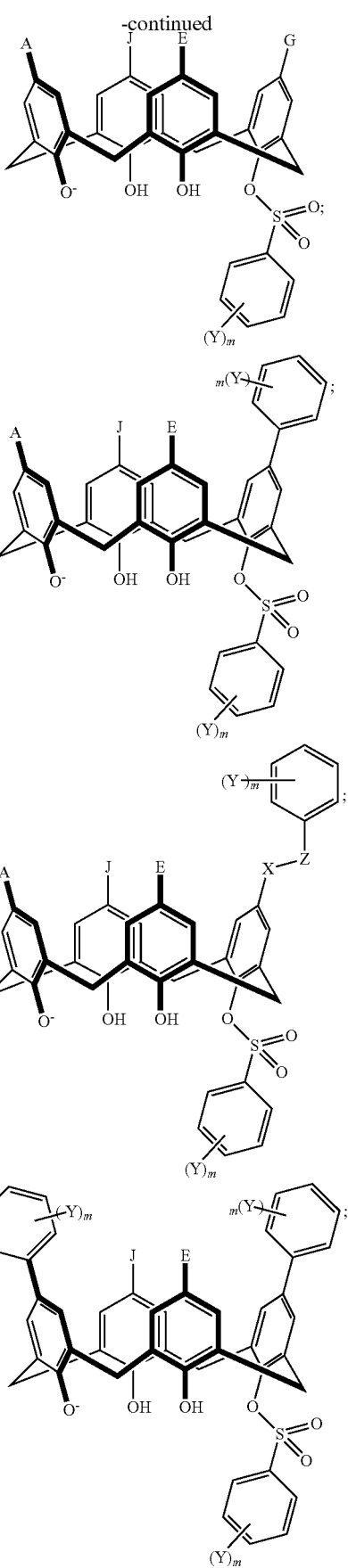

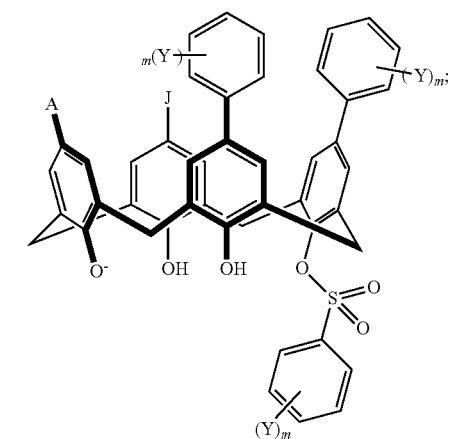
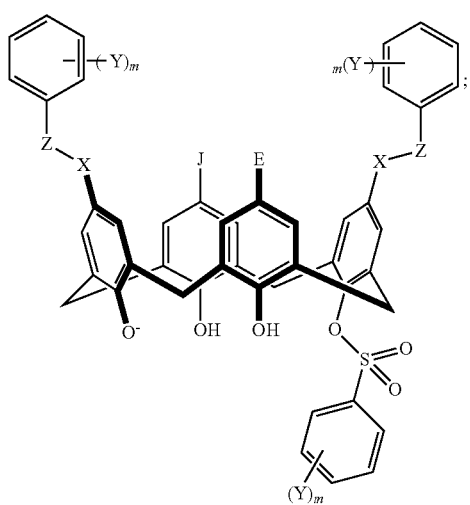
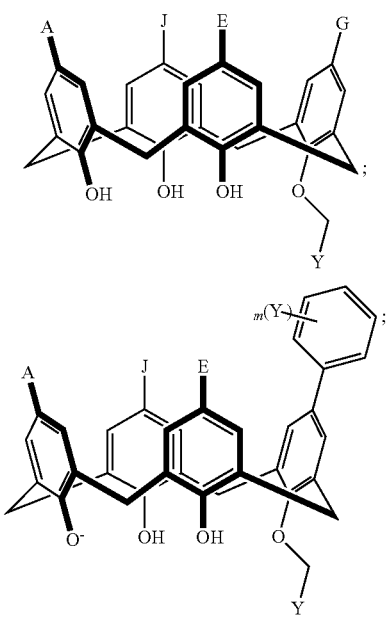
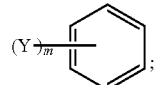
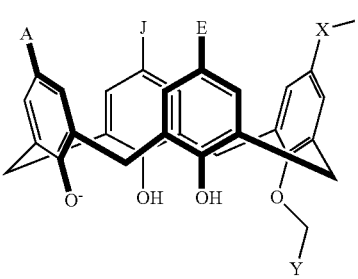
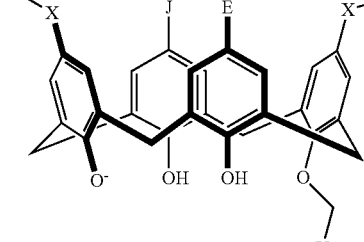
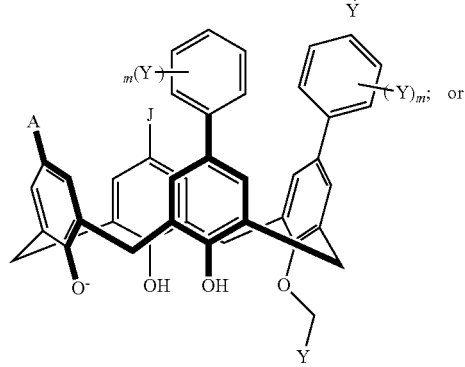
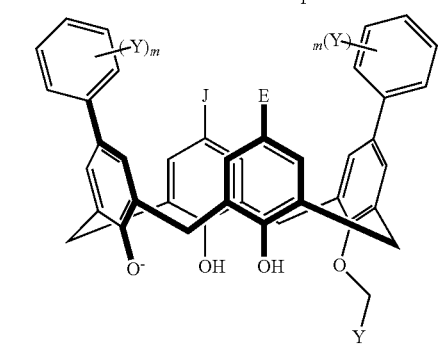
wherein each Y of the $(Y)_m$ group independently is —$(CH_2)_pC(O)NH_2$, —$(CH_2)_pC(O)OH$, —$(CH_2)_pNH_2$, or —$(CH_2)_pNH_3^+$ wherein each p independently is an integer selected from 0 to 10 and each m is an integer selected from 0 to 4, each X independently is NH, and each Z independently is $SO_2$.

9. The conjugate of claim 1, wherein the compound has a formula
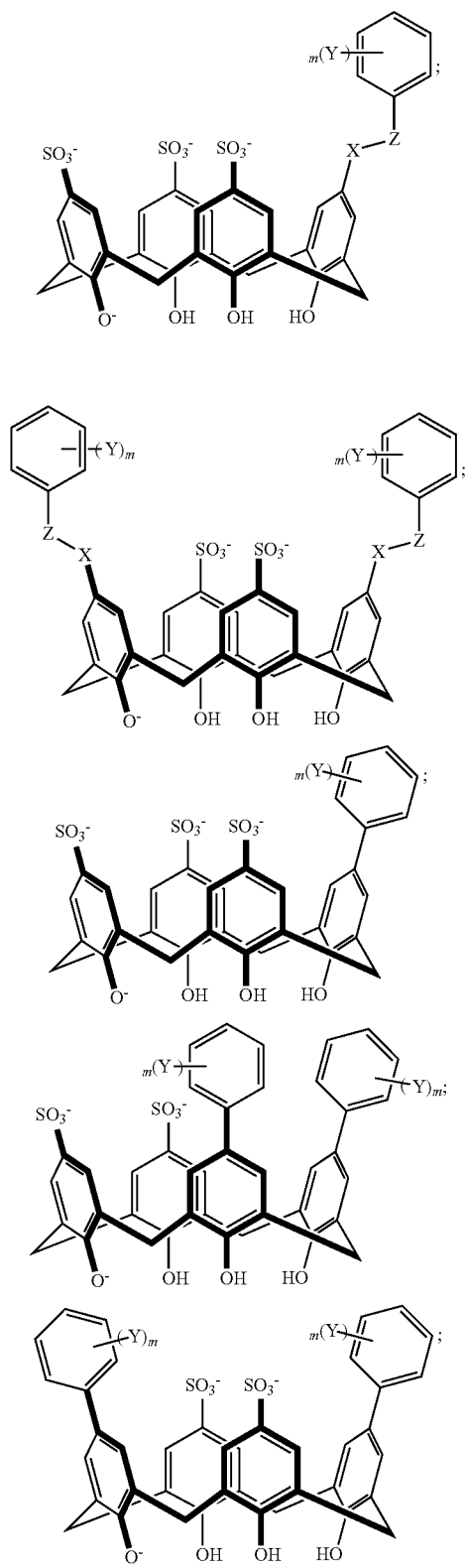
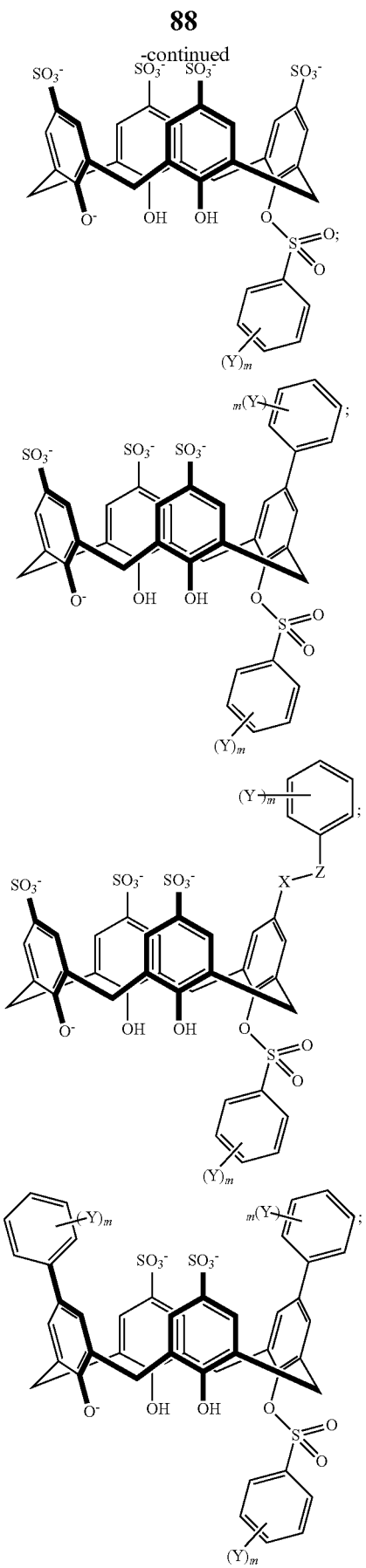

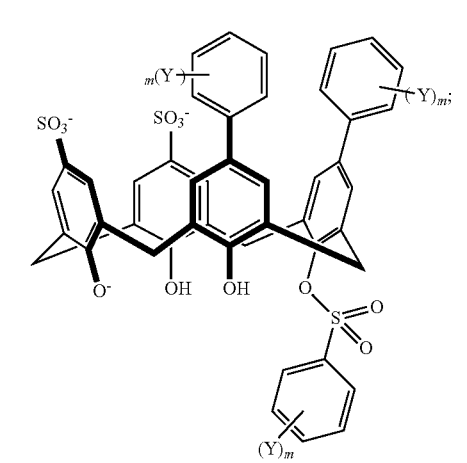
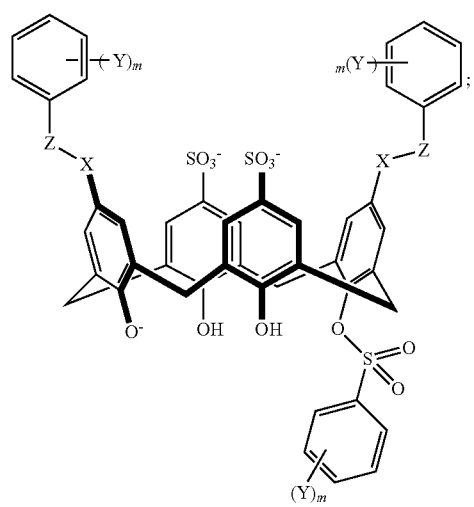
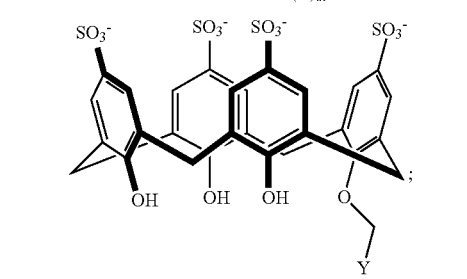
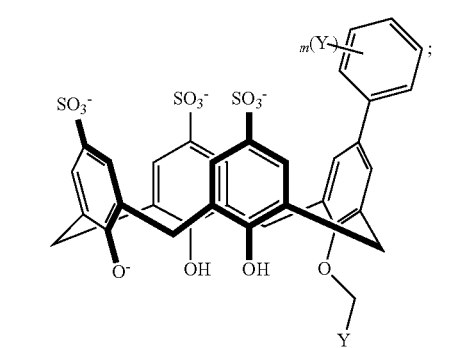
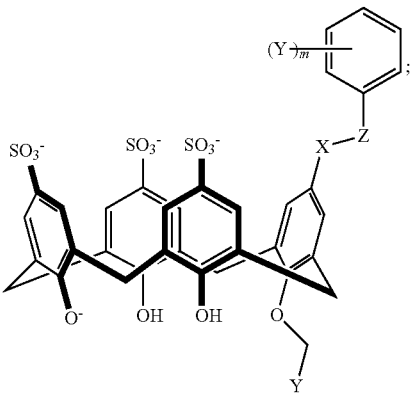
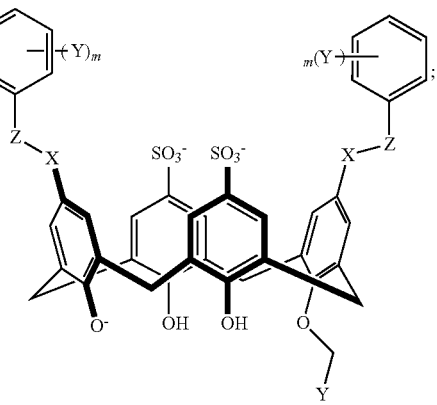
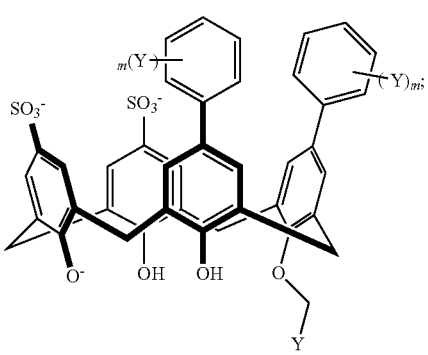
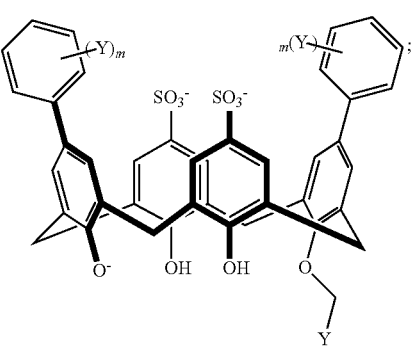

91
-continued
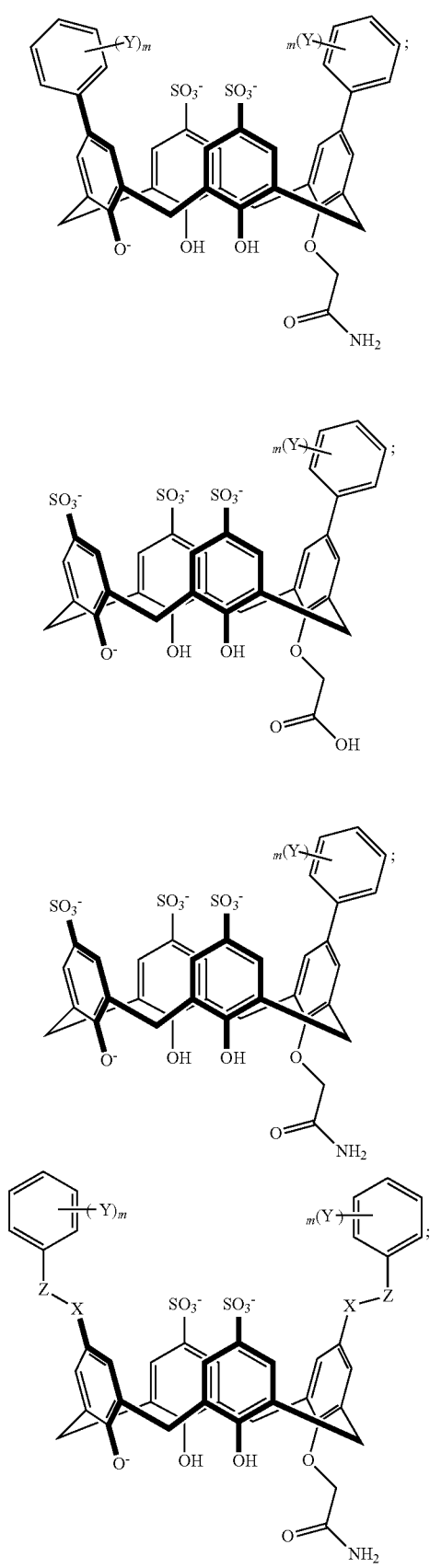
92
-continued
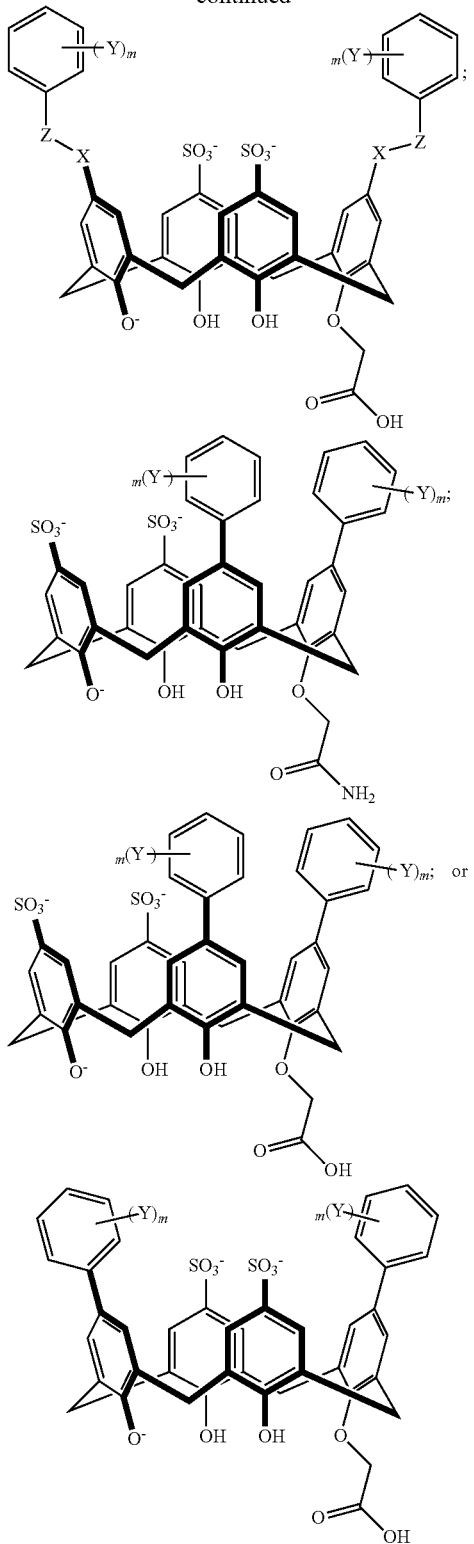
wherein each Y of the $(Y)_m$ group independently is
—$(CH_2)_pC(O)NH_2$, —$(CH_2)_pC(O)OH$, —$(CH_2)_pNH_2$,
or —$(CH_2)_pNH_3^+$, wherein each p independently is an
integer selected from 0 to 10, and each m is an integer
selected from 0 to 4, and wherein the compound
includes a counterion provided by an aqueous solution.

10. The conjugate of claim 1, wherein the compound is
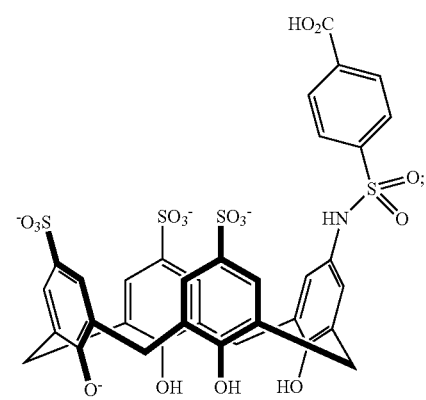
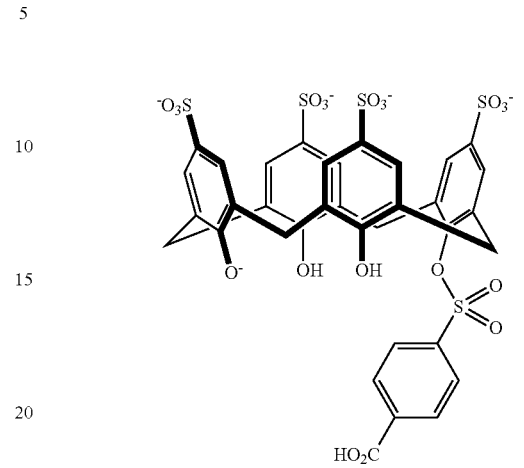
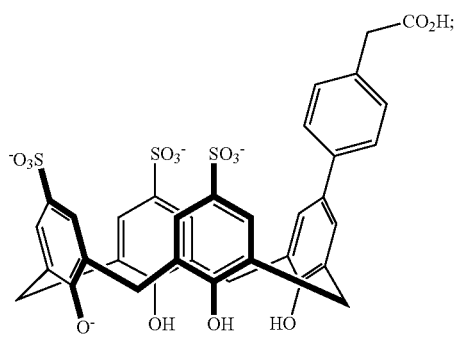
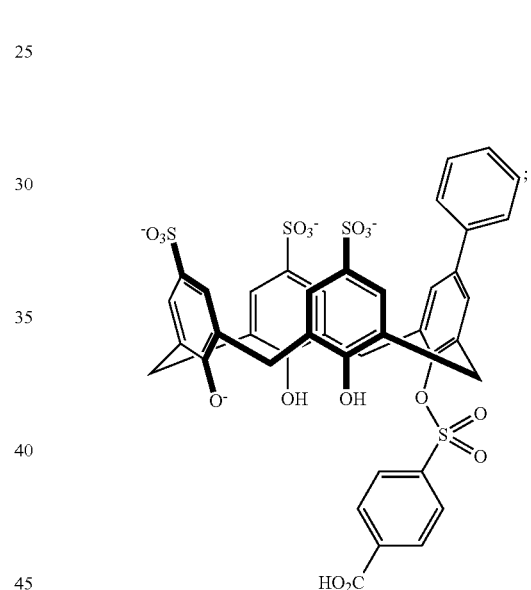
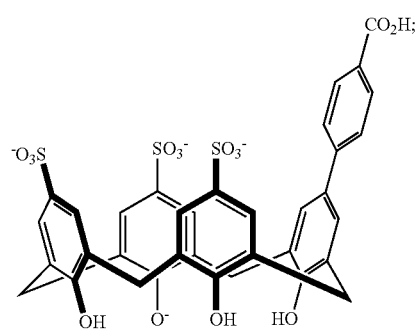
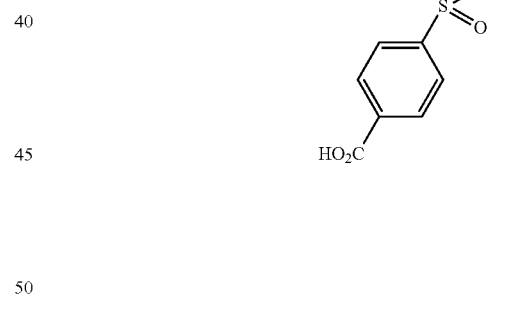
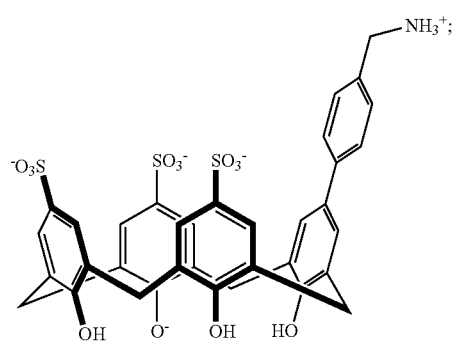
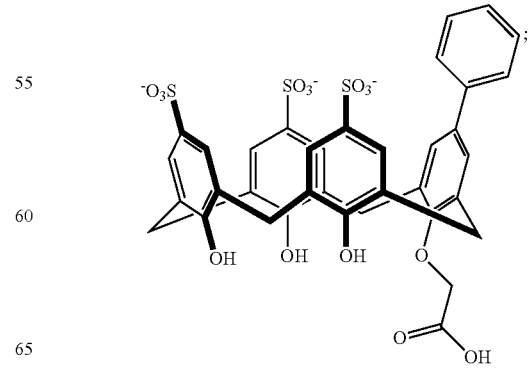

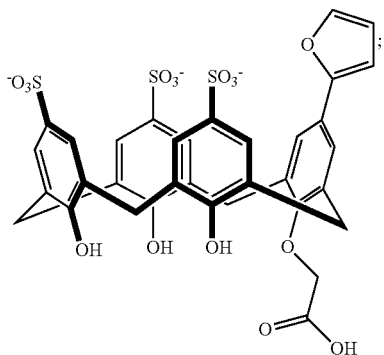

wherein the compound includes one or more counterions provided by an aqueous solution.

11. The conjugate of claim 1, wherein the conjugate has a structure satisfying Formula II

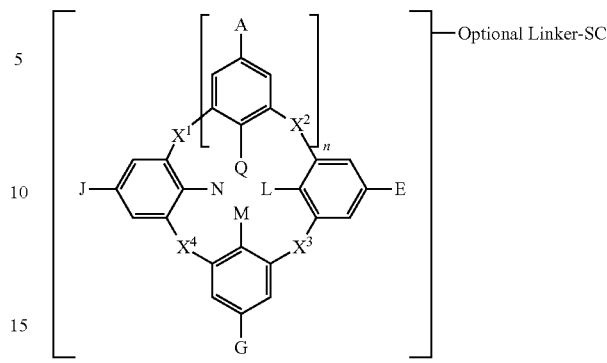

wherein:
SC is the support component, wherein SC is covalently coupled to at least one of A, E, G, J, L, M, N, or Q directly or through the optional linker, which, if present is selected from aliphatic, heteroaliphatic, aryl, or heteroaryl.

12. The conjugate of claim 1, wherein the conjugate has a structure satisfying a formula

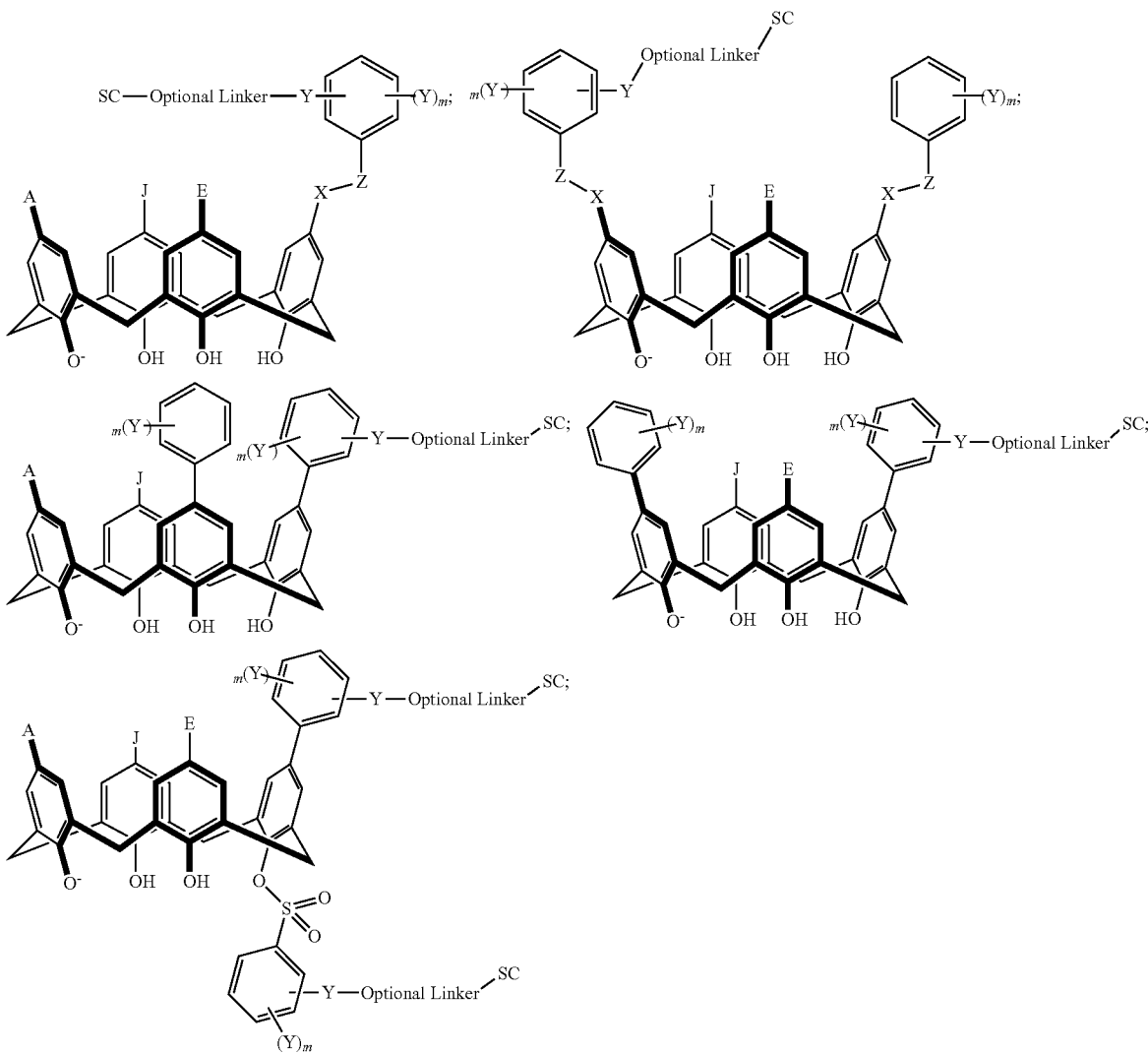

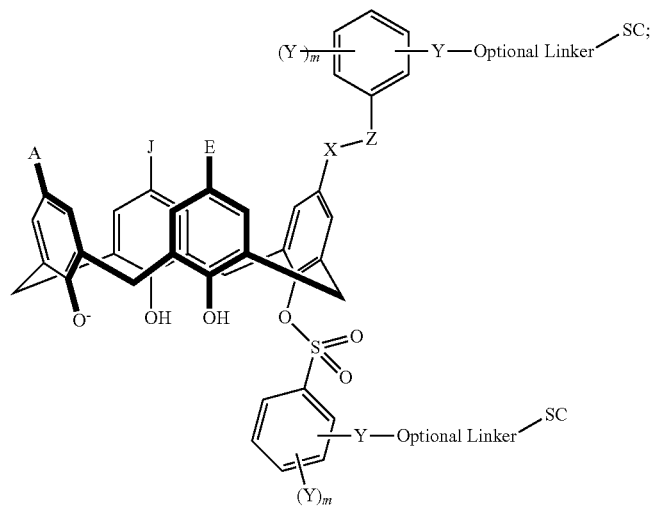
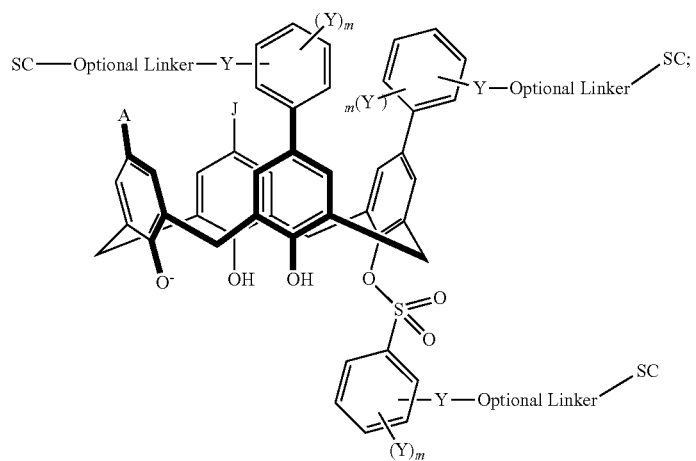
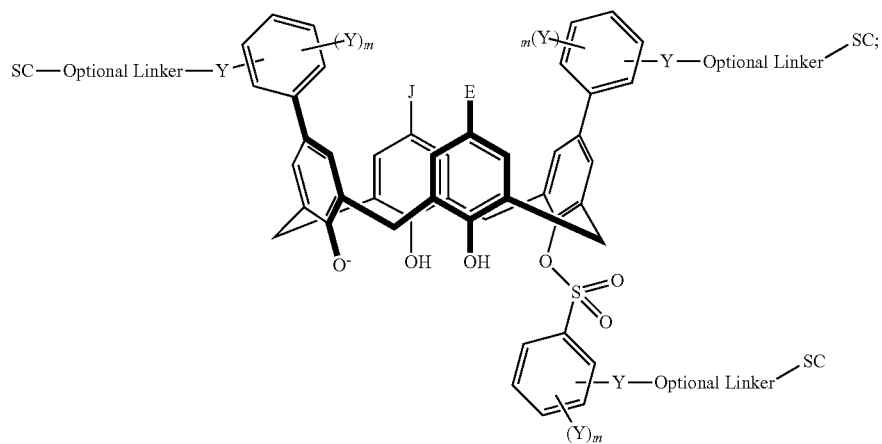

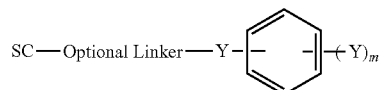 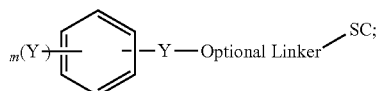
-continued
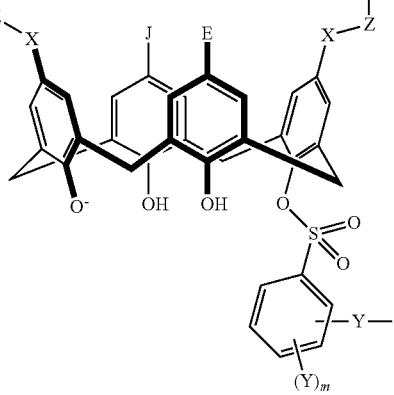
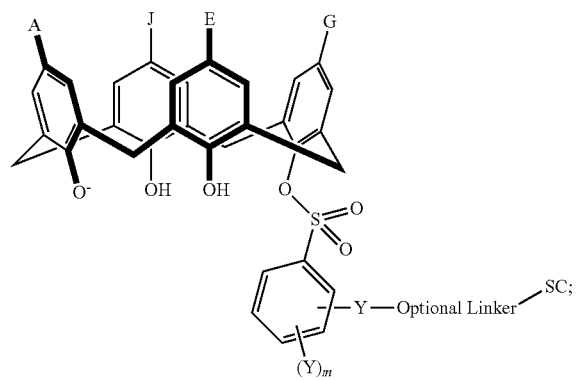
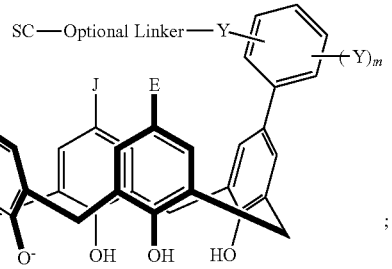
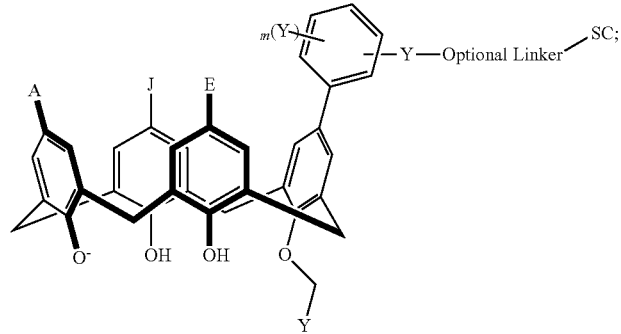
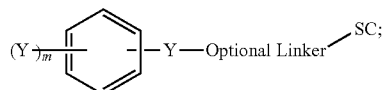
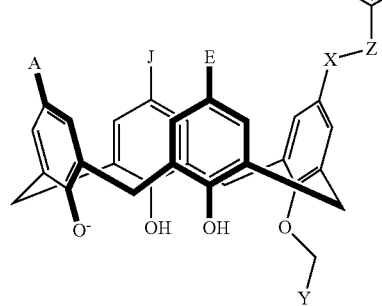

-continued

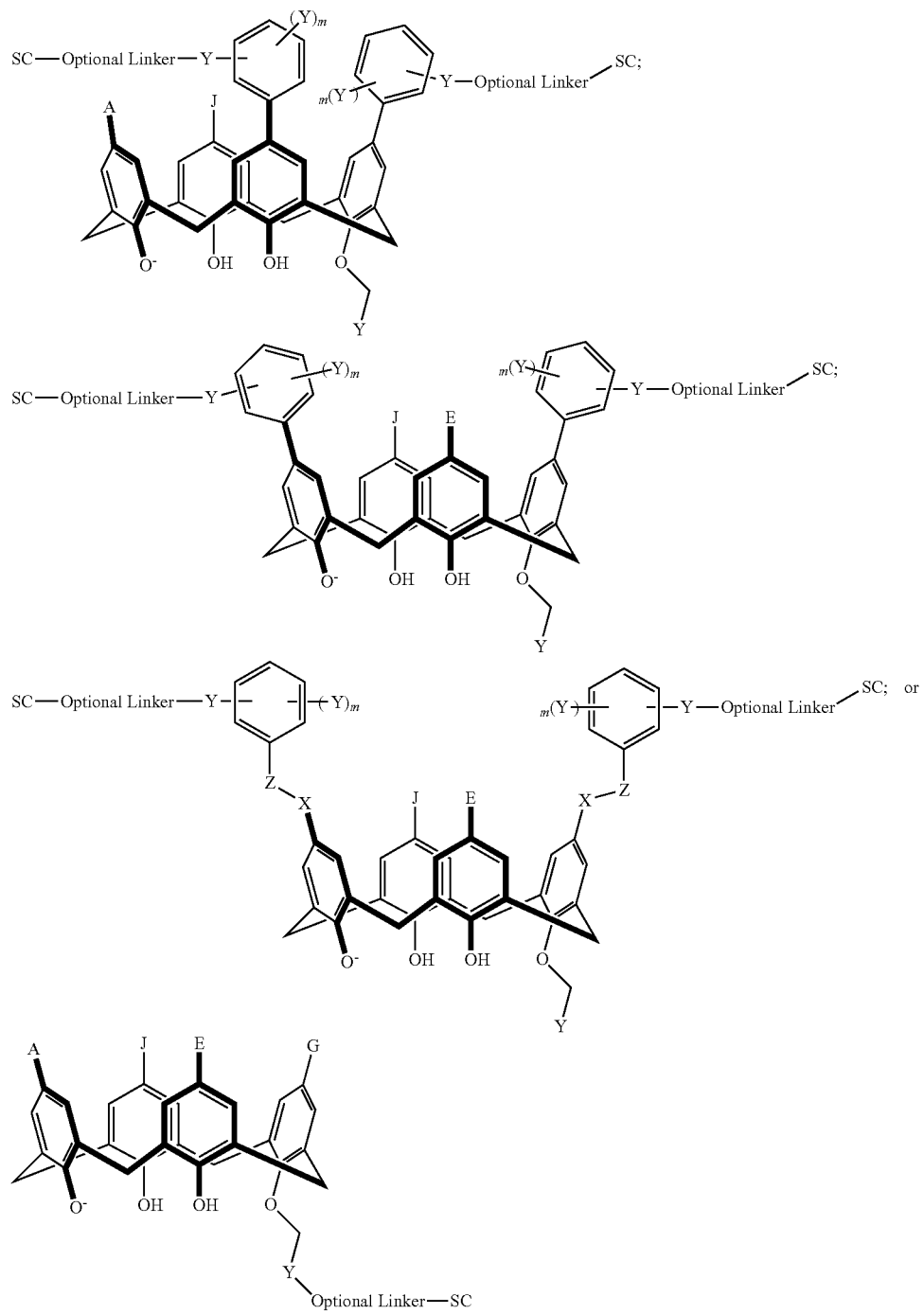

wherein:

each Y of the (Y)$_m$ group independently is —(CH$_2$)$_p$C(O)NH$_2$, —(CH$_2$)$_p$C(O)OH, —(CH$_2$)$_p$NH$_2$, or —(CH$_2$)$_p$NH$_3^+$; and each Y bound to the SC group directly, or by the optional linker, is —(CH$_2$)$_p$C(O)NH—, —(CH$_2$)$_p$C(O)O—, —(CH$_2$)$_p$NH—;

each optional linker, if present, is aliphatic, heteroaliphatic, aryl, heteroaryl, or a heteroatom-containing functional group;

each X independently is NH;

each Z independently is SO$_2$;

each p independently is an integer selected from 0 to 10;

each m is an integer selected from 0 to 4; and
each SC is the support component.
13. The conjugate of claim 1 wherein the conjugate is
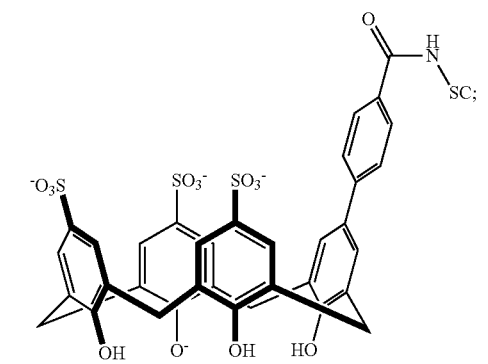
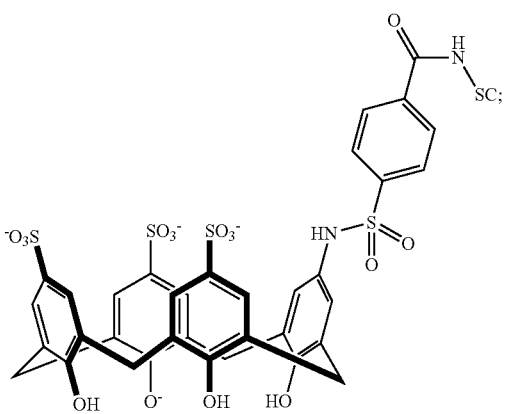
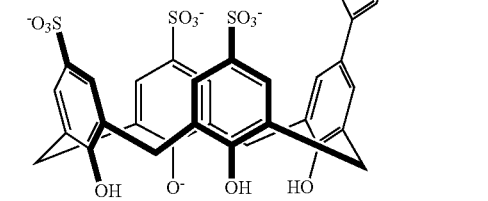
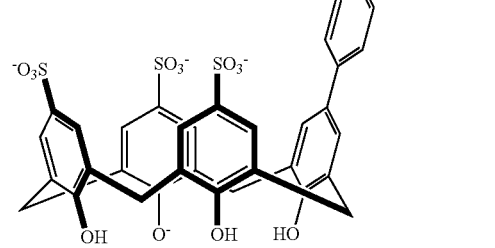
-continued
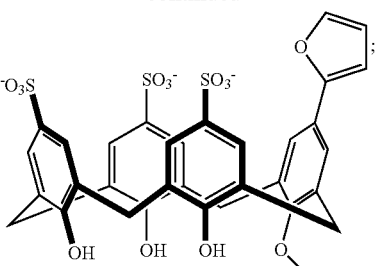
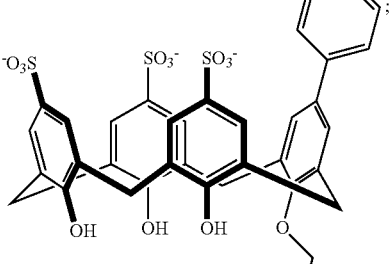
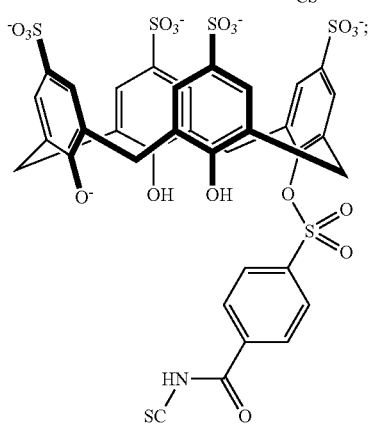
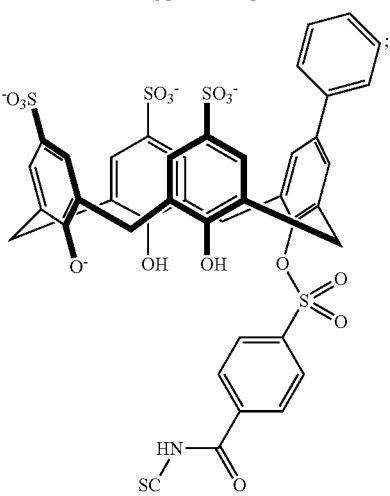

105
-continued
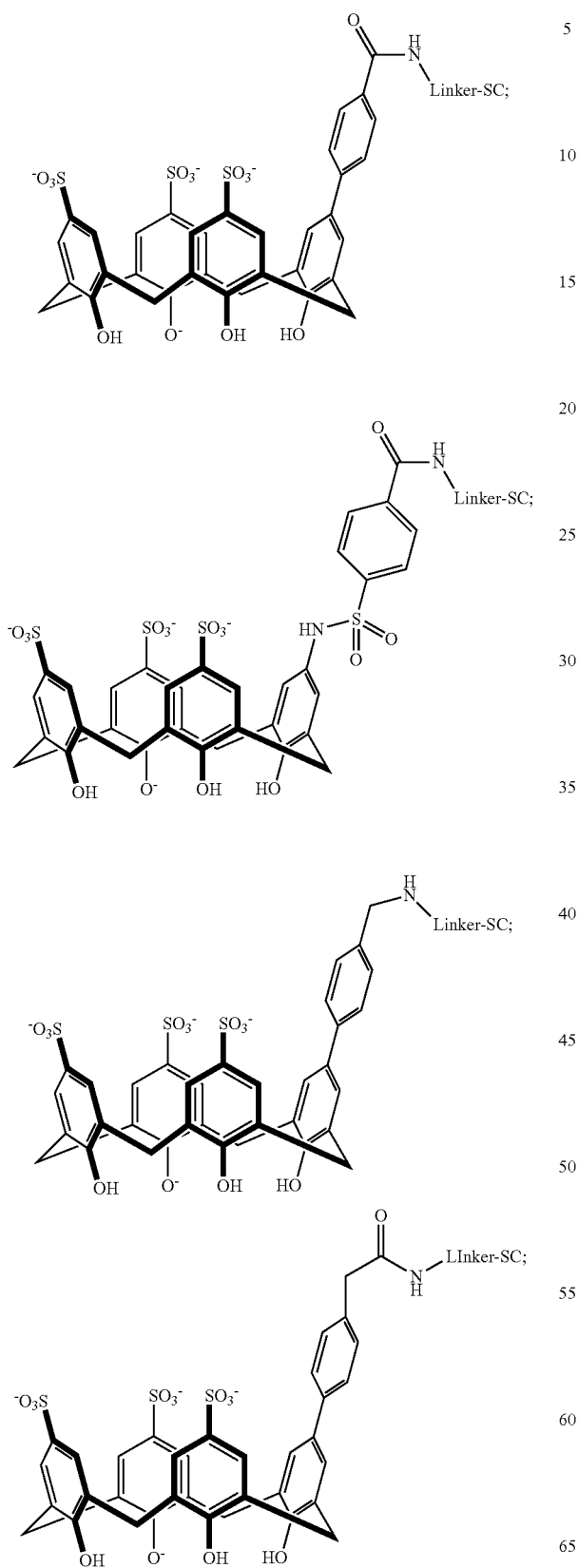
106
-continued
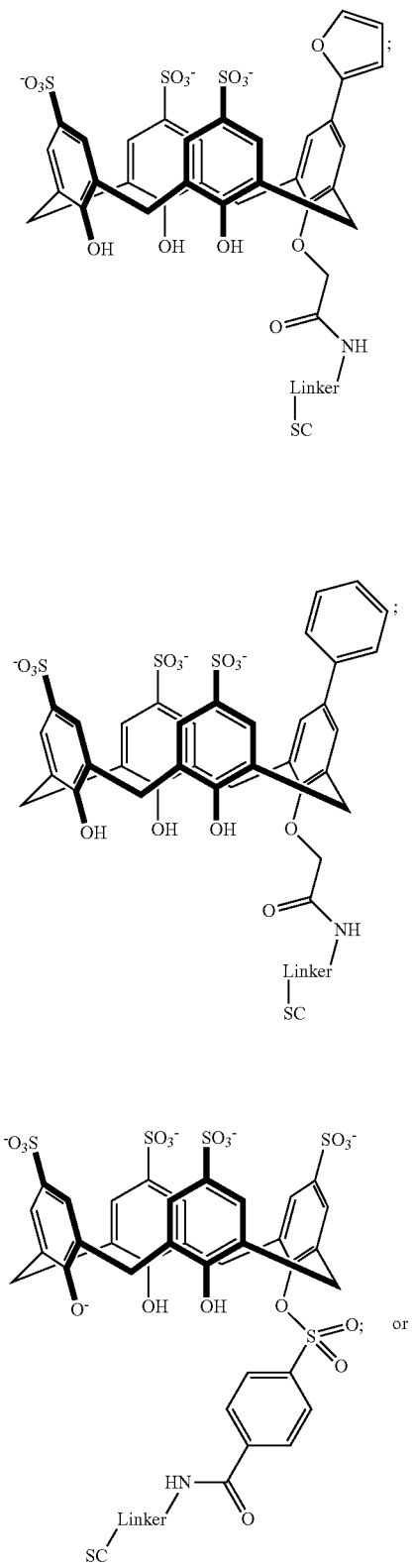

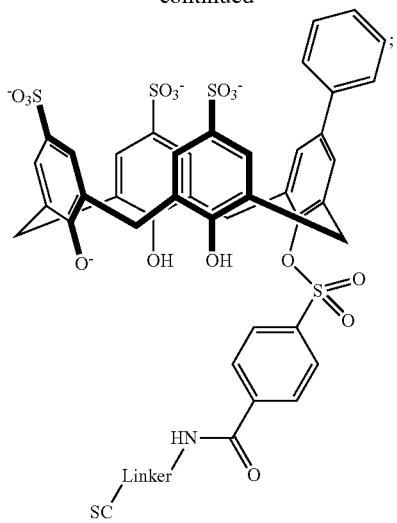

wherein:
  each linker independently is aliphatic, heteroaliphatic, aryl, heteroaryl, or a heteroatom-containing functional group; and
  each SC is the support component.

14. A chromatography column comprising one or more of the conjugates of claim 1.

15. The conjugate of claim 1, wherein one or more of L, N, and Q is —OC(O)Ph(CH$_2$)$_p$(Y)$_m$ or —OSO$_2$Ph(CH$_2$)$_p$(Y)$_m$; and any remaining L, N, or Q variables are independently —OH or —O$^-$.

16. The conjugate of claim 1, wherein G and at least one of A, E, or J is aryl, heteroaryl, —NR$^b$SO$_2$-aryl (wherein R$^b$ independently is hydrogen, aliphatic, heteroaliphatic, aryl, or heteroaryl), or —NR$^b$SO$_2$heteroaryl (wherein R$^b$ independently is hydrogen, aliphatic, heteroaliphatic, aryl, or heteroaryl); and the remaining of A, E, and J are —SO$_3^-$.

17. A method, comprising:
  introducing a fluid sample comprising one or more analytes into a solid-phase column packed with one or more conjugates according to claim 1;
  applying a first buffer of a first concentration to the solid-phase column; and
  applying a second buffer of a second concentration to elute one or more post-translationally modified analytes present in the sample.

18. The method of claim 17, wherein the first buffer is a low ionic strength phosphate buffer and the second buffer is a salt buffer selected from a chloride salt buffer, a sulfate salt buffer, or a citrate salt buffer.

19. The method of claim 17, wherein the method further comprises adjusting flow rates and concentrations of the first buffer and the second buffer through the column so as to control elution times of the analytes present in the sample and wherein the analytes elute at different times depending on whether or not they are associated with the compound of the conjugate.

20. A conjugate, wherein the conjugate is a compound having a structure satisfying Formula I that is covalently coupled to a support component by at least one of A, E, G, J, L, M, N, or Q of Formula I, either directly or through an aliphatic linker, a heteroaliphatic linker, an aryl linker, or a heteroaryl linker, wherein Formula I is

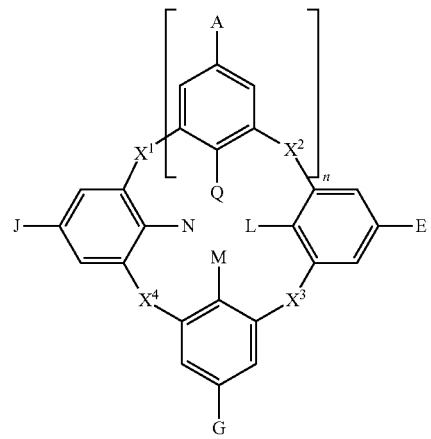

Formula I and wherein
  G is aryl, heteroaryl, -linker-aryl, —SO$_3^-$, —SO$_3$H, or -linker-heteroaryl, wherein each linker independently is a sulfonamide;
  each of A, E, and J independently is SO$_3^-$; —SO$_3$H; aryl; heteroaryl; -linker-aryl; or -linker- heteroaryl, wherein each linker independently is a sulfonamide;
  M is —OH; —O$^-$; or —OSO$_2$Ph(CH$_2$)$_p$(Y)$_m$; wherein each Y independently is alkyl, alkoxy, amide, thiol, thioether, aldehyde, carboxyl, ester, NH$_2$, or NH$_3$+, p is an integer selected from 0 to 10, and m is an integer selected from 0 to 4;
  each of L, N, and Q independently is —OH; —O$^-$; or —O(CH$_2$)$_p$Y, wherein Y is alkyl, alkoxy, amide, thiol, thioether, aldehyde, carboxyl, ester, NH$_2$, or NH$_3$+, and p is an integer selected from 0 to 10;
  each of X$^1$, X$^2$, X$^3$, and X$^4$ is CH$_2$;
  n is an integer selected from 1 to 3; and provided that
    if M is —OH or -0$^-$, then G is aryl, heteroaryl, -linker-aryl, or -linker-heteroaryl, wherein each linker independently is a sulfonamide; or
    if M is —OSO$_2$Ph(CH$_2$)$_p$(Y)$_m$, then G is aryl, heteroaryl, -linker-aryl, —SO$_3$, —SO$_3$H, or -linker-heteroaryl, wherein each linker independently is a sulfonamide.

21. The conjugate of claim 20, wherein
each of A, E, G and J independently is —SO$_3^-$ or —SO$_3$H;
M is —OSO$_2$Ph(CH$_2$)$_p$Y; where Y is alkyl, alkoxy, amide, thiol, thioether, aldehyde, carboxyl, ester, NH$_2$, or NH$_3^+$, and p is an integer selected from 0 to 10; and
the support component is covalently coupled to Y.

22. The conjugate of claim 20, wherein
G is aryl, heteroaryl, -linker-aryl, or -linker-heteroaryl, wherein each linker independently is a sulfonamide;
each of A, E, and J independently is —SO$_3^-$ or —SO$_3$H;
each of M, L, N, and Q independently is —OH; —O$^-$; or —O(CH$_2$)$_p$Y, wherein Y is alkyl, alkoxy, amide, thiol, thioether, aldehyde, carboxyl, ester, NH$_2$, or NH$_3$+, and p is an integer selected from 0 to 10; and
the support component is covalently coupled to G through a heteroaliphatic linker.

* * * * *